(12) United States Patent
Yang et al.

(10) Patent No.: US 8,450,093 B1
(45) Date of Patent: May 28, 2013

(54) ADAPTIVE ENGINEERING OF CLOSTRIDIUM FOR INCREASED BUTANOL PRODUCTION

(75) Inventors: Shang-Tian Yang, Dublin, OH (US); Jingbo Zhao, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 13/293,003

(22) Filed: Nov. 9, 2011

Related U.S. Application Data

(60) Provisional application No. 61/411,782, filed on Nov. 9, 2010, provisional application No. 61/547,607, filed on Oct. 14, 2011.

(51) Int. Cl.
| | |
|---|---|
| *C12P 7/16* | (2006.01) |
| *C12N 15/00* | (2006.01) |
| *C12N 1/20* | (2006.01) |
| *C12M 1/00* | (2006.01) |
| *C12M 3/00* | (2006.01) |

(52) U.S. Cl.
USPC .................................................. 435/160

(58) Field of Classification Search
None
See application file for complete search history.

(56) References Cited

U.S. PATENT DOCUMENTS

| 5,192,673 A * | 3/1993 | Jain et al. ............... 435/160 |
| 2005/0089979 A1* | 4/2005 | Ezeji et al. ............... 435/150 |
| 2009/0155869 A1* | 6/2009 | Buelter et al. ............. 435/160 |

OTHER PUBLICATIONS

Liu, Jiahong et al. Downstream Process Synthesis for Biochemical Production of Butanol, Ethanol, and Acetone from Grains: Generation of Optimal and Near-Optimal Flowsheets with Conventional Operating Units. Biotechnology Progress. 2004. 20. 1518-1527.*
Nolling, Jork et al. Genome Sequencing and Comparative Analysis of the Solvent-Producing Bacterium *Clostridiium acetobutylicum*. Journal of Bacteriology. 2001. 183:16 4823-4838.*
Liu et al., Downstream Process Synthesis for Biochemical Production of Butanol, Ethanol, and Acetone from Grains: U Generation of Optimal and Near-Optimal Flowsheets with Conventional Operating Units. Biotechnology Progress. 2004. 20. 1518-1527.
Nolling et al. Genome Sequencing and Comparative Analysis of the Solvent-Producing Bacterium *Clostridiium acetobutylicum*. Journal of Bacteriology. 2001. 183:16 4823-4838.

* cited by examiner

*Primary Examiner* — David J Steadman
*Assistant Examiner* — Paul Hollan
(74) *Attorney, Agent, or Firm* — Standley Law Group LLP

(57) ABSTRACT

Adaptive engineering of microorganisms to create mutants exhibiting high butanol tolerance and productivity. Mutant strains are obtained through the fermentation of parental strains in a fibrous bed bioreactor in the presence of butanol. Also provided are methods of producing butanol using mutant strains in ABE fermentation. Butanol production may be furthered by gas stripping and distillation. Also provided are mutant proteins for increasing butanol production in a microorganism.

10 Claims, 31 Drawing Sheets

```
ATCC 55025    1    MENFSDKDELIHKWDSFIGTVEKNPTLRPLTMESWKRCKNMGVNPKHIKLKTLSHNELND
                   ||||||||||||||||||||||||||||||||||||||||||||||||||||||||||||
JB 200        1    MENFSDKDELIHKWDSFIGTVEKNPTLRPLTMESWKRCKNMGVNPKHIKLKTLSHNELND

61    KISNNLHLIKIVKPYFDYLFLRVTNIPFLIALADSKAWIINISGNVNDFGEKKFRFCLGS
                   |||||||||||||||||||||||||||||||||||||||||||||||||||
             61    KISNNLHLIKIVKPYFDYLFLRVTNIPFLIALADSKAWIINISGNVNDFGEKNLDFALVL

121    NCSEKYIGNNGIGTCLTCGKPIIIYGREHFVNAYASFTCIGVPIKVNKKIVGAIDVCIPN

121    IVLKNILVIME.................................................

181    KYAHPSIFDLTISCVESIQSTLSIIDRSSIKNSPNMLSRTSKLLATAVHDLKNPLSVIR

181    ............................................................

241    GLGQLGKLTSDKAKADYFDKVIKQADELNTMVVELLSIFSPPKIKPMEISKIIKDVIEE

241    ............................................................

301    FEPQCNSKKISLNIINSNSSYANISEPLFKRAIRNLISNAIQAIDIDGSIEIKIKQENKH

301    ............................................................

361    IILSITDTAGGIPEELRDNLFEPFTEKRSGGTGLGLFMVYHTITNTHNGEMWFHTTPGNG

361    ............................................................

421    TTFFIKLPIANPTSDLDMDKYNLMM

```
ATCC 55025  1  AGCGGGTAGAGGGAATCGAACCCTCGTAACTAGCTTGGAAAGGCTAGCACTCTACCATTG
               ||||||||||||||||||||||||||||||||||||||||||||||||||||||||||||
JB 200      1  AGCGGGTAGAGGGAATCGAACCCTCGTAACTAGCTTGGAA.GGCTAGCACTCTACCATTG

61  AGTTACACCCGC
               ||||||||||||
           61  AGTTACACCCGC
```

```
ATCC 55025   1  MNTKMHNKKKRIFSIYILLILLIRLFLSTGVRIWAFGNNQYDDGMMIKNATNLIAGNWLG
                ||||||||||||||||||||||||||||||||||||||||||||||||||||||||||||
JB 200       1  MNTKMHNKKKRIFSIYILLILLIRLFLSTGVRIWAFGNNQYDDGMMIKNATNLIAGNWLG

61  SYDQYIFAKGVTFPIYLELLHKIGIPFIISNVLMCFAASLTFIIVIKKVIPNLNALAIIY
                ||||||||||||||||||||||||||||||||||||||||||||||||||||||||||||
            61  SYDQYIFAKGVTFPIYLELLHKIGIPFIISNVLMCFAASLTFIIVIKKVIPNLNALAIIY

121  TILMFNPIATASWTFQRVYRDSLYSYLIVILFSLIIGIYLNRKESFNKLLSYSIVAGFFL
                ||||||||||||||||||||||||||||||||||||||||||||||||||||||||||||
           121  TILMFNPIATASWTFQRVYRDSLYSYLIVILFSLIIGIYLNRKESFNKLLSYSIVAGFFL

181  SSVWLAREDSPWVLPFVGMALIVTLVLIFLDKNSEMKVRMKKALALTVIPIFLIVSILVV
                ||||||||||||||||||||||||||||||||||||||||||||||||||||||||||||
           181  SSVWLAREDSPWVLPFVGMALIVTLVLIFLDKNSEMKVRMKKALALTVIPIFLIVSILVV

241  STINYTRYGVAITNEYTGGYLPRLFKDLTIIQPDEWMAQVPIPKSTREKAYKVSPTFSKL
                ||||||||||||||||||||||||||||||||||||||||||||||||||||||||||||
           241  STINYTRYGVAITNEYTGGYLPRLFKDLTIIQPDEWMAQVPIPKSTREKAYKVSPTFSKL
```

FROM FIG-15A

```
301  KNTLENHAFVATTPGNASCSMLAWAVIDSVQWYGIKDAKSSQEFYKKSSEEIEAAIKSG
     ||||||||||||||||||||||||||||||||||||||||||||||||||||||||||||
301  KNTLENHAFVATTPGNASCSMLAWAVIDSVQWYGIKDAKSSQEFYKKSSEEIEAAIKSG

361  KLKTRGGYIFMFESPWDNRYVKPLLKSFIQTIKTTVHMGQYYNMEEESLVKTLQLSRKYN
     ||||||||||||||||||||||||||||||||||||||||||||||||||||||||||||
361  KLKTRGGYIFMFESPWDNRYVKPLLKSFIQTIKTTVHMGQYYNMEEESLVKTLQLSRKYN

421  NTIVPLFEKNIASIGTKEQVRKLEYITNNIAYNKEDVIPKRQTKVAISNKISLIYYELNP
     ||||||||||||||||||||||||||||||||||||||||||||||||||||||||||||
421  NTIVPLFEKNIASIGTKEQVRKLEYITNNIAYNKEDVIPKRQTKVAISNKISLIYYELNP

481  YLFLIGLNRLCVYYTALFTKYKKEKILFS...............................
              ||  ||||  | ||
481  YLFLIGLIGYVYITLRFLLSIRKKKYFLADEWLITTGIFLSYLLRLLLISYTDVCSIFMQ

541  ............................................................
541  YSMYLAPSYWLILMFTFTSIFISMRDFVKNYYYNKKASHKN
```

FIG-15B

ADAPTIVE ENGINEERING OF CLOSTRIDIUM FOR INCREASED BUTANOL PRODUCTION

CROSS-REFERENCE TO RELATED APPLICATIONS

This application claims the benefit of priority from U.S. Provisional Patent Application No. 61/547,607, filed Oct. 14, 2011, and U.S. Provisional Patent Application No. 61/411,782, filed Nov. 9, 2010, which are both hereby incorporated by reference in their entirety.

TECHNICAL FIELD

Adaptive engineering of microorganisms and methods of producing biofuels, particularly adaptive engineering of mutant strains of *Clostridium acetobutylicum* capable of high butanol production, and methods of using mutant strains of *Clostridium acetobutylicum* to produce butanol.

BACKGROUND OF THE ART

With concerns about greenhouse gas emissions and uncertainty about the supply of oil, renewable biofuels have been gaining increasing attention. Butanol has received increasing interest because it can use renewable biomass as feedstock and is environmentally friendly. Butanol can be produced by anaerobic microorganisms such as *Clostridium acetobutylicum* and *Clostridium beijerinckii* in acetone-butanol-ethanol fermentation (ABE fermentation), which was once the second largest industrial fermentation in the world. In a typical ABE fermentation, butyrate and acetate are produced first, and then the culture undergoes a metabolic shift and solvents (butanol, acetone, and ethanol) are formed. In conventional ABE fermentation, the butanol yield is low (<25% w/w), titer is low (<12 g/L) and productivity is low (<0.3 g/L·h). This is largely due to the fact that high concentrations of butanol are toxic to the bacteria that produce the solvent. Other byproducts of ABE fermentation, including acetone, ethanol, acetate and butyrate, also inhibit butanol production by the bacteria. The low reactor productivity, butanol yield, and final butanol concentration make biobutanol from ABE fermentation uneconomical for the fuel market. However, if final butanol concentration could be raised from 12 to 19 g/L, the costs of butanol recovery from the fermentation broth could be cut in half, making ABE fermentation a much more desirable source of butanol.

Since the first oil crisis in the early 1980's, there have been numerous attempts to improve butanol production by metabolically engineering bacteria to have higher butanol tolerance and yet maintain butanol productivity. The problem is that metabolic engineering is limited by available molecular or functional knowledge of bacteria.

SUMMARY OF THE INVENTIVE CONCEPT

This and other unmet advantages are provided by the methods and compositions described and shown in more detail below.

Provided herein are methods of obtaining a non-sporulating, solventogenic mutant bacterial strain that exhibits higher butanol tolerance and higher titer butanol production than its parental strain. In certain embodiments, methods or producing butanol include subjecting a non-sporulating solventogenic bacterial host strain to fermentation in a fibrous bed bioreactor (FBB) in the presence of butanol, obtaining mutant strains surviving the fermentation, identifying a mutant strain capable of higher butanol production than the host strain, isolating the mutant strain, and subjecting the mutant strain to fermentation with a substrate. In some methods of producing butanol, steps may be taken to recover the butanol using a gas stripping system. The gas stripping system may utilize a stripping gas comprised of $CO_2$ and $H_2$, and it may also comprise a condenser for condensing vapor at a predetermined temperature, which may be 0° C. In certain embodiments the method of producing butanol may include a step for purifying the gas stripping condensate by distillation.

In certain embodiments, the non-sporulating solventogenic bacterial strain is *Clostridium acetobutylicum*. In certain embodiments, the bacterial strain may be *Clostridium acetobutylicum* ATCC 55025. In certain embodiments the substrate used by a mutant strain to produce butanol may be selected from the group consisting of glucose, fructose, xylose, maltose, sucrose, galactose, or starch. In other embodiments the substrate may be selected from the group consisting of starchy biomass, lignocellulosic biomass, and sugar-containing biomass.

In certain embodiments, methods of isolating bacterial strains capable of butanol production include the steps of subjecting a bacterial strain to fermentation in the presence of butanol, and selecting a mutant surviving the fermentation based on its exhibition of a desired property. The desired property may be selected from the group consisting of increased butanol production and increased tolerance.

In certain embodiments, isolated bacterial strains characterized by increased production of butanol and identifiable by a mutant sequence are provided. In certain embodiments the mutant sequence may be one of the following: SEQ. ID No. 1, SEQ. ID No. 3, SEQ. ID No. 5, SEQ. ID No. 6, SEQ. ID No. 8, and SEQ. ID No. 10.

BRIEF DESCRIPTION OF THE DRAWINGS

A better understanding of the present invention will be obtained from a reading of the following detailed description and the accompanying drawings wherein identical reference characters refer to identical parts and in which:

FIG. 13 shows the alignment of the SEQ ID NO: 1 protein sequence of JB200 and the SEQ ID NO: 12 protein sequence of parental strain ATCC 55025;

FIGS. 15*a* and 15*b* show the alignment of the SEQ. ID NO. 3 protein sequence of JB200 and the SEQ ID NO: 13 protein sequence of parental strain ATCC 55025;

DESCRIPTION OF THE MICROORGANISM DEPOSITS MADE UNDER THE BUDAPEST TREATY

Figure 1:
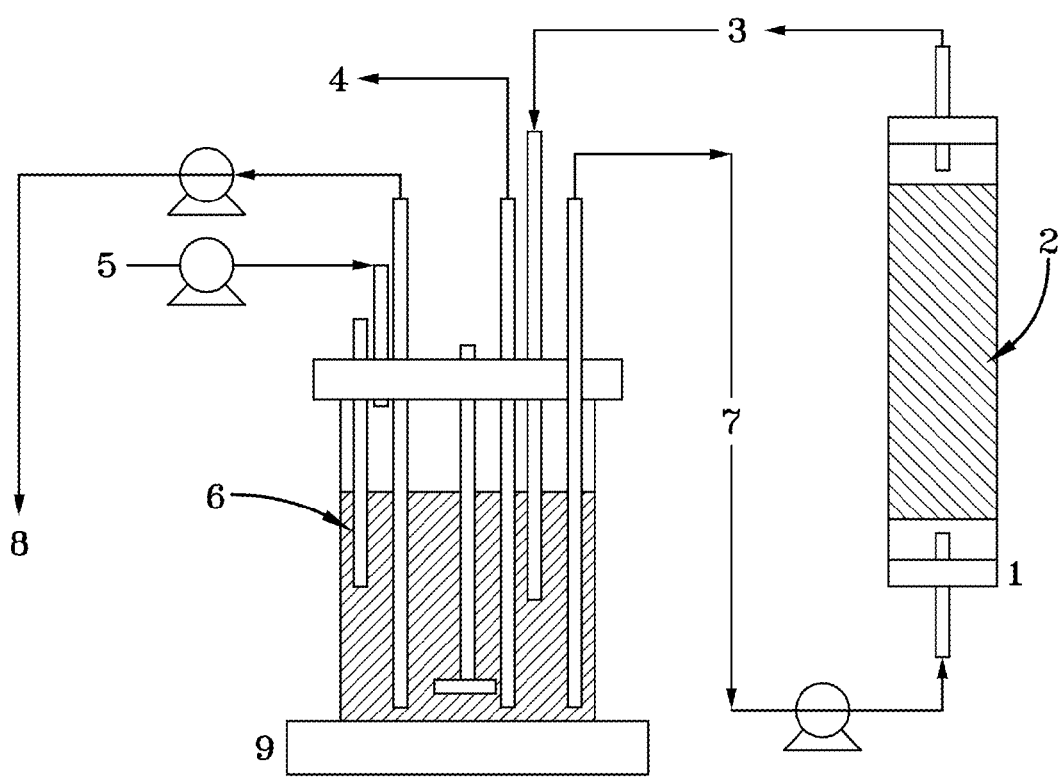
FIG. 1 is a diagram of a fibrous bed bioreactor (FBB) system.

The following biological deposits have been made under the terms of the Budapest Treaty on the International Recognition of the Deposit of Micro-organisms for the Purposes of Patent Procedure:

| Depositor Identification Reference | International Depository Designation | Date of Deposit |
|---|---|---|
| *Clostridium acetobutylicum* JB200 | ATCC_ | Received by ATCC in Manassas, Virginia on Nov. 3, 2011 |

| SEQUENCE DESCRIPTIONS | | |
|---|---|---|
| Protein/Nucleic Acid | Description | SEQ. ID Nos. |
| mCA_C3319 | Signal transduction histidine kinase protein found in JB200 | SEQ. ID No. 1 |
| mCA_C3319DNA | DNA sequence encoding for mCA_C3319 | SEQ. ID No. 2 |
| mCA_C0967 | Membrane protein found in JB200 | SEQ. ID No. 3 |
| mCA_C0967DNA | DNA sequence encoding for mCA_C0967 | SEQ. ID No. 4 |
| mCA_Ct025 | RNA coding sequence found in JB200 | SEQ. ID No. 5 |
| mCA_C0603 | ATP-dependent zinc metallopeptidase FtsH (cell division protein) in JB200 | SEQ. ID No. 6 |
| mCA_C0603DNA | DNA sequence encoding for mCA_C0603 | SEQ. ID No. 7 |
| mCA_C1684 | TYPA/BIPA type GTPase in JB200 | SEQ. ID No. 8 |
| mCA_C1684DNA | DNA sequence encoding for mCA_C1684 | SEQ. ID No. 9 |
| mCA_C3173 | 3-isopropylmalate dehydratase large subunit in JB200 | SEQ. ID No. 10 |
| mCA_C3173DNA | DNA sequence encoding for mCA_C3173 | SEQ. ID No. 11 |

DETAILED DESCRIPTION OF A PREFERRED EMBODIMENT

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

Any publications discussed above and throughout the text are provided solely for their disclosure prior to the filing date of the present application. Nothing herein is to be construed as an admission that the inventors are not entitled to antedate such disclosure by virtue of prior disclosure.

The section headings used herein are for organizational purposes only and are not to be construed as limiting the described subject matter in any way. In addition, the materials, methods, and examples are illustrative only and not intending to be limiting. The use of the singular includes the plural unless specifically stated otherwise. Also, the use of "comprise," "comprises," "comprising," "contain," "contains," "containing," "include," "includes," and "including" are not intended to be limiting. It is understood that both the foregoing general description and the following detailed description are exemplary and explanatory only and are not restrictive of the invention. The articles "a" and "an" are used herein to refer to one or to more than one (i.e., to at least one) of the grammatical object of the article.

All numbers expressing quantities of ingredients, reaction conditions, and so forth used in the specification and claims are understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

As utilized in accordance with the embodiments provided herein, the following terms, unless otherwise indicated, shall be understood to have the following meanings:

The term "native" or "wild-type" as used with a protein, enzyme, polynucleotide, gene, or cell, means a protein, enzyme, polynucleotide, gene, or cell that occurs in nature.

The term "mutant" or "mutant strain" refers to a non-wild type strain, or a strain that is genetically different from a host or parental strain. In certain embodiments of the invention, a mutant strain may exhibit greater expression of an ability relative to the wild type or parental counterpart, i.e., an increased activity mutant. In other embodiments a mutant strain may lack a trait exhibited by the wild type or parental counterpart. A mutant may be the result of adaptive engineering. For example, adaptive engineering may result in a mutant strain that has different genetic material than a wild type or parental strain. The difference in genetic material may be in response to environmental conditions the mutant was subjected to during an adaptive engineering process.

"Adaptation" is the change in the physiological and/or genetic structure of a microorganism to become better suited to its environment.

"Adaptive engineering" or "adaptive evolution engineering" refers to inducing genetic changes in a microorganism through subjecting an organism to particular environmental conditions. Adaptive engineering of an microorganism may result in a mutant microorganism that, when compared to a parental or wild-type strain, exhibits new properties, e.g., the ability to produce a new, or greater quantities of, an intracellular metabolite. In an illustrative embodiment, the adaptation of a microorganism results in a new or modified ability to produce butanol.

Adaptive engineering of a microorganism may result in the introduction of new genetic material into a host or parental microorganism. In the alternative, adaptive engineering of a microorganism may also result in the disruption, deletion, substitution, or knocking out of a gene, amino acid, polynucleotide, or nucleotide, which results in an alteration of the cellular physiology and biochemistry of the microorganism. Through the adaptive engineering process the microorganism may acquire new or improved properties (e.g., the ability to produce a new or greater quantities of an intracellular metabolite, improve the flux of a metabolite down a desired pathway, and/or reduce the production of undesirable by-products).

Bacterial Strains and Growth Conditions

Bacterial strains used in the examples are listed in Table 1 below:

| Strains or plasmids | Description | Reference or source |
| --- | --- | --- |
| Strains | | |
| Clostridium acetobutylicum | ATCC 55025 | ATCC |
| Clostridium acetobutylicum | ATCC 824 | ATCC |
| Clostridium acetobutylicum | JB200 | The examples |
| Clostridium beijerinckii | NCIMB 8052 | NCIMB |
| Clostridium beijerinckii | BA 101 | Annous, et al., 1991. |

In general, a fibrous bed bioreactor (FBB) based adaptation process is used for obtaining an improved, solventogenic, non-sporulating mutant strain of *C. acetobutylicum* that exhibits higher butanol tolerance and higher titer butanol production than parental strains. Through adaptation in the FBB, followed with screening on agar plates, a high butanol-tolerant mutant strain of *Clostridium acetobutylicum* with the ability to produce up to 21 g/L butanol in conventional free-cell fermentation and 28.2 g/L butanol in the FBB fermentation can be obtained. The parental strain and other solventogenic Clostridia usually can only produce about 12.5 g/L butanol in free cell fermentation and 16 g/L butanol in the FBB. Compared with the parental strain, the mutant strain has higher saturated fatty acids content in the cytoplasmic membrane. While the parental strain and other known solventogenic Clostridia usually stop growth (and are lysed) at 10-12 g/L butanol, the mutant strain can grow at 16 g/L butanol. The hyper-butanol producing mutant strain can be used to produce butanol from various substrates, including glucose, fructose, xylose, maltose, sucrose, galactose, starch, and starchy, lignocellulosic, and sugar-containing biomass. The mutant strain can be used to produce butanol from any other carbon source or carbohydrate. When the mutant strain is used in ABE fermentation coupled with gas stripping for continuous butanol recovery, high butanol productivity and yield can be achieved with a butanol titer of >150 g/L in the gas stripping condensate that can be easily purified by distillation with a low energy input.

The original, or "parent" strain used is *Clostridium acetobutylicum* ATCC 55025, which is an anaerobic, asporogenic solvent-producing strain and can be purchased from America Type Culture Collection in Manassas, Va. *Clostridium* growth medium (CGM) and P2 medium are used for seed growth and butanol fermentation, respectively.

CGM medium has the following contents: Glucose 50 g/L, $(NH_4)_2SO_4$ 2 g/L, $K_2HPO_4$ 1 g/L, $KH_2PO_4$ 0.5 g/L, $MgSO_4.7H_2O$ 0.1 g/L, $FeSO_4.7H_2O$ 0.015 g/L, $CaCl_2.2H_2O$ 0.015 g/L, $MnSO_4.H_2O$ 0.01 g/L, $CoCl_2.6H_2O$ 0.02 g/L, $ZnSO_4.7H_2O$ 0.002 g/L, Tryptone 2 g/L, Yeast extract 1 g/L. 1000× stock solutions of $FeSO_4.7H_2O$, $CaCl_2.2H_2O$, $MnSO_4.H_2O$, $CoCl_2.6H_2O$, and $ZnSO_4.7H_2O$ were prepared separately, stored in 4° C. refrigerator and used during medium preparation. Before autoclaving, 100 ml CGM medium in 125-ml serum bottle was purged with $N_2$ gas for 8 min. Then the serum bottle was sealed with a butyl rubber stopper and an aluminum cap and sterilized by autoclaving at 120° C., 15 psig, for 30 min.

The P2 medium (with 10% glucose) is made of four solutions: Solution 1: Glucose 100 g/L, Yeast extract 1 g/L; Solution 2: $K_2HPO_4$ 0.5 g/L, $KH_2PO_4$ 0.5 g/L, Ammonium acetate 2.2 g/L; Solution 3: Para-amino-benzoic acid 0.001 g/L, Thiamine 0.001 g/L, Biotin 0.00001 g/L; and Solution 4: $MgSO_4.7H_2O$ 0.2 g/L, $MnSO_4.H_2O$ 0.01 g/L, $FeSO_4.7H_2O$ 0.01 g/L, NaCl 0.01 g/L. 100 ml of 20× Solution 2 in 125-ml serum bottle are purged and sterilized as that of CGM medium described above.

1000× stock solution of Solution 3 and 200× stock solution of Solution 4 are prepared and sterilized by 0.2 μm membrane filter, separately. The stock solutions are stored in a 4° C. refrigerator.

To prepare 2 L of P2 medium in the fermentor, 200 g glucose and 2 g yeast extract in 1.9 L water (Solution 1) are put into a fermentor and autoclaved at 120° C., 15 psig, for 30 min. An anaerobic condition is formed by purging the solution in a fermentor with $N_2$ gas immediately after autoclave. After the solution in the fermentor was cooled to 37° C., 100 ml of 20× Solution 2 in 125-ml serum bottle, 2 ml 1000× Solution 3, and 10 ml 200× Solution 4 are added into the fermentor aseptically. The pH of the prepared P2 medium in fermentor may be about 6.5.

Besides CGM, two modified CGM media, B-CGM and BN-CGM, are also used during adaptation. In B-CGM, 2 g/L $(NH_4)_2SO_4$ is replaced by 3 ml/L butyric acid and the pH is adjusted to 6.5 with $NH_3.H_2O$ after autoclaving. In BN-CGM, more yeast extract and tryptone are used (5 g/L and 4 g/L instead of 1 g/L and 2 g/L) compared with B-CGM. All media are sterilized by autoclaving at 120° C., 15 psig, for 30 min. An anaerobic condition is formed by purging the medium in a serum bottle or fermentor with nitrogen before autoclaving or immediately after autoclaving, respectively.

Fibrous Bed Bioreactor (FBB) and Adaptation

To construct a fibrous bed bioreactor (FBB), a piece of cotton towel (approximately 27×25 cm) is spirally wound together with a stainless steel mesh and packed into a glass column fitted with a water jacket. The broth flows from bottom to top of the FBB. The working volume of the FBB is about 500 ml. A modified FBB is also constructed using fibrous disks, which are made into cakes and placed into the column without steel mesh. For the modified FBB, the broth flows from top to bottom, like a filtration process.

Adaptation is conducted in a FBB-connected fermentor system, which is formed by connecting the FBB to a 5-L stirred-tank fermentor (Marubishi MD-300, Japan). The fermentor system is illustrated in FIG. 1 wherein the reference numbers identify the following: 1: FBB; 2: towel fiber; 3: FBB out; 4: sample; 5: base; 6: pH sensor; 7: FBB in; 8: feed or drain; and 9: 5-L stirred tank fermentor. In this system, the recirculation loop is formed by circulating fermentation broth with a peristaltic pump. Mixing and pH control of the broth is realized in the fermentor by a magnetic-stirrer device and an automatic base addition. Unless otherwise noted, 2 L of medium is used in this system with the temperature controlled at 37° C., agitation at 100 rpm, and a pH held above 5.0 by the addition of $NH_3.H_2O$. To start the fermentation and adaptation process, 100 ml of exponentially-growing *Clostridium acetobutylicum* (ATCC 55025) cells cultured in a serum bottle are inoculated into the fermentor with 2 L of CGM medium. The cells are fermented in the FBB for approximately 55 h with no circulation. When the cell concentration reaches an optical density at 600 nm ($OD_{600}$) of 2.0, cell immobilization is carried out by circulating the fermentation broth through the FBB at a flow rate of 16 ml/min. After around 48 h of continuous circulation, no change of the $OD_{600}$ of the broth may be identified, which shows dynamic adsorption and desorption of cells onto and from the fibrous matrix. At this time, all broth in the system is drained and another batch of fermentation is started by pumping into the fermentor 2 L of fresh CGM medium and circulating the broth at the same flow rate. In the following examples, batch or fed-batch fermentations are conducted in this system to optimize medium composition and process conditions. During this process, cells immobilized in the FBB are used as seeds for each subsequent batch of fermentation. After the highest butanol titer is reached in every batch, broth is not drained immediately, but is continuously circulated through FBB for a period of time, typically 3 to 5 days, allowing the cells to be intermittently challenged with butanol produced by themselves. Samples are taken at regular intervals for the analysis of cell, glucose and product concentrations.

Screening Methods

After 1350 h of fermentation and adaptation, cell samples are taken from the FBB-connected fermentor and spread onto B-CGM agar plates after dilution in an anaerobic chamber. The agar plates are incubated at 37° C. for 3 days. Some of the colonies that form on these plates are selected and inoculated into 2-ml centrifuge tubes with 1 ml CGM medium, respectively. After incubation at 37° C. for 16 h, 0.25 ml cultures from these seed tubes are used to inoculate 5 ml P2 (8% glucose) medium in 50-ml centrifuge tubes with screw caps, respectively. After 96 h of static fermentation at 37° C. in anaerobic chamber, broth samples are taken for the analysis of glucose and product concentrations.

Free Cell and Immobilized Cell Fermentation in Fermentor

A 5-L stirred-tank fermentor (Marubishi MD-300) with 2 L P2 (10% glucose) medium is used to conduct free cell fermentation. Seed culture is prepared by inoculating 0.1 ml of glycerol stock of specific strain into 100 ml CGM medium in serum bottle and incubated at 37° C. for about 18 h. Then, the 100 ml seed culture is inoculated into the fermentor to start a batch of fermentation, during which temperature is controlled at 37° C., agitation is at 100 rpm, and pH is kept above 5.0 by adding $NH_3.H_2O$. Immobilized cell fermentation is the same as free cell fermentation except that a newly-packed FBB is connected to the fermentor to form a recirculation loop like that used in adaptation. Seed preparation and inoculation are the same as that of free cell fermentation. Upon inoculation, the peristaltic pump is started to circulate the broth at a flow rate of 16 ml/min. During fermentation, samples are taken at regular intervals for the analysis of cell, glucose, and product concentrations.

Butanol Tolerance Analysis

Butanol tolerances of different strains are investigated and compared according to the maximal specific growth rates achieved under the challenge of different concentrations of butanol. Seed cultures are prepared the same way as those used for fermentor fermentation. Then, seeds of different strains are inoculated into 10 ml of CGM medium in serum tubes supplemented with different concentrations of butanol. The tubes are incubated at 37° C. and optical densities ($OD_{600}$) are measured every 2 h. Growth curves may be drawn according to the $OD_{600}$ data. Maximal specific growth rates ($h^{-1}$) of different strains under different butanol concentrations may be calculated based on the growth curves.

Cell Membrane Fatty Acid Assay

During free cell fermentation in fermentor, samples are removed at early exponential phase and late stationary phase.

For ATCC 55025, exponential phase occurs at approximately 5 h, $OD_{600}$ 1.0; and late stationary phase occurs at approximately 50 h, $OD_{600}$ 4.0. For JB200, exponential phase occurs at approximately 10 h, $OD_{600}$ 1.0; and late stationary phase occurs at approximately 70 h, $OD_{600}$ 10.0. Cells are harvested and stored at −20° C. Cell membrane fatty acid analysis is done by methylation of fatty acid and subsequent gas chromatography analysis at a professional company, Microbial ID, Inc. (Newark, Del.). Fatty acid methyl esters are prepared from whole cells rather than the cell membrane since no statistical difference was observed in early reports with *C. acetobutylicum* ATCC 842. The composition of individual fatty acids was identified and reported as a percentage of total fatty acids. The variability of values for fatty acid composition is less than 5%.

2-D Gel Electrophoresis and Proteome Analysis

During fermentation of ATCC 55025 in the fermentor, fermentation broth in exponential phase (5 h, $OD_{600}$ about 1.0, referred to as the "AE" sample) and stationary phase (50 h, $OD_{600}$ about 4.0, referred to as the "AS" sample) are taken and cell pellets are collected by centrifugation at 4000×g for 10 min at 4° C. Similarly, cell pellets of the mutant under consideration are collected from the fermentation broth in exponential phase (10 h, $OD_{600}$ about 1.0, referred to as the "BE" sample) and stationary phase (70 h, $OD_{600}$ about 10.0, referred to as the "BS" sample). All cell pellet samples (AE, AS, BE, and BS) are stored in a freezer at −80° C. until use.

To prepare protein extracts for two-dimensional electrophoresis (2-DE), a portion of each cell pellet sample (AE, AS, BE, and BS) is lysed in 500 μl of osmotic lysis buffer containing 10× nuclease stock, phosphatase inhibitor stocks (I and II), protease inhibitor stock, and 100 mg of washed glass beads (Sigma G9268, mesh size 425-6000 microns). The samples are vortexed for 5 minutes, frozen, and vortexed again for 5 minutes. 300 μl of SDS boiling buffer minus β-mercaptoethanol (BME) is added, and samples are heated in a boiling water bath for five minutes before protein concentration determinations are performed using the BCA Assay (Pierce Chemical Co., Rockford, Ill.). Samples are then lyophilized and re-dissolved to 4 mg/ml in a 1:1 ratio with diluted SDS boiling buffer/urea sample buffer. 50 μl of these protein extracts (200 μg) are used for isoelectric focusing (IEF).

Two-dimensional electrophoresis is performed according to the carrier ampholine method of IEF by Kendrick Labs, Inc. (Madison, Wis.). IEF is carried out in a glass tube having an inner diameter of 2.3 mm, using a 2% pH 4-8 mix of ampholines (GE Healthcare, Piscataway, N.J. and Serva, Heidelberg, Germany) for 9600 volt-hrs. One μg of an IEF internal standard, tropomyosin, is added to the sample. This protein migrates as a doublet with lower polypeptide spot of MW 33,000 and pI 5.2. The enclosed tube gel pH gradient plot for this set of ampholines is determined with a surface pH electrode. After equilibration for 10 min in Buffer 'O' (10% glycerol, 50 mM dithiothreitol, 2.3% SDS and 0.0625 M tris, pH 6.8), each tube gel is sealed to the top of a stacking gel that overlays a 10% acrylamide slab gel (0.75 mm thick, 15 cm×13 cm). SDS slab gel electrophoresis is carried out for about 4 hrs at 15 mA/gel. Coomassie brilliant blue R250 (Sigma-Aldrich, St. Louis, Mo.) staining is used to visualize protein spots on gel. Comparative image analysis was performed with Progenesis SameSpots software (Nonlinear Dynamics, Newcastle upon Tyne, United Kingdom) by aligning and analyzing gels from the AE, BE, AS, and BS cell samples. Proteins displaying significantly up- or down-regulation in these gels are considered and selected for identification.

Gels are digested with sequencing-grade trypsin from Promega (Madison Wis.) using the Multiscreen Solvinert Filter Plates from Millipore (Bedford, Mass.). Protein spots are trimmed as close as possible to minimize background polyacrylamide material. Gel pieces are then washed in Nanopure® water for 5 minutes. The wash step may be repeated twice before gel pieces are washed twice with 1:1 v/v methanol/50 mM ammonium bicarbonate for ten minutes per piece. The gel pieces are dehydrated with 1:1 v/v acetonitrile/50 mM ammonium bicarobonate. The gel pieces are rehydrated and incubated with dithiothreitol (DTT) solution (25 mM in 100 mM ammonium bicarbonate) for 30 minute prior to the addition of 55 mM iodoacetamide in 100 mM ammonium bicarbonate solution. Iodoacetamide is incubated with the gel pieces in the dark for 30 min before it is removed. The gel pieces are washed again with two cycles of water and then dehydrated with 1:1 v/v acetonitrile/50 mM ammonium bicarobonate. The protease is driven into the gel pieces by rehydrating them in 12 ng/ml trypsin in 0.01% ProteaseMAX Surfactant (Promega, Madison, Wis.) for 5 minutes. The gel pieces are then overlaid with 40 ml of 0.01% ProteaseMAX surfactant/50 mM ABC and gently mixed on a shaker for 1 hour. The digestion is stopped with the addition of 0.5% trifluoroacetic acid (TFA).

Capillary-liquid chromatography-nanospray tandem mass spectrometry (Nano-LC/MS/MS) is performed on a Thermo Finnigan LTQ mass spectrometer equipped with a nanospray source operated in positive ion mode. The LC system is an UltiMate™ 3000 system from Dionex (Sunnyvale, Calif.). The solvent A is water containing 50 mM acetic acid and the solvent B is acetonitrile. 5 μl of each sample is first injected onto the μ-Precolumn Cartridge (Dionex, Sunnyvale, Calif.), and washed with 50 mM acetic acid. The injector port is switched to inject and the peptides are eluted off of the trap onto the column. A 5 cm×75 μm ID ProteoPep II C18 column (New Objective, Inc. Woburn, Mass.) packed directly in the nanospray tip is used for chromatographic separations. Peptides are eluted directly off the column into the LTQ system using a gradient of 2-80% B over 45 minutes, with a flow rate of 300 nl/min. The total run time is 65 minutes. The MS/MS is acquired according to standard conditions established in the lab. Briefly, a nanospray source operated with a spray voltage of 3 KV and a capillary temperature of 200° C. is used. The scan sequence of the mass spectrometer is based on the TopTen™ method; the analysis is programmed for a full scan recorded between 350-2000 Da, and a MS/MS scan to generate product ion spectra to determine amino acid sequence in consecutive instrument scans of the ten most abundant peaks in the spectrum. The CID fragmentation energy is set to 35%. Dynamic exclusion is enabled with a repeat count of 2 within 10 seconds, a mass list size of 200, and an exclusion duration 350 seconds. The low mass width is 0.5 and the high mass width is 1.5.

Sequence information from the MS/MS data is processed by converting the .raw files into a merged file (.mgf) using an in-house program, RAW2MZXML_n_MGF_batch (merge.pl, a Perl script), although other programs may be used. The resulting .mgf files are searched using Mascot Daemon by Matrix Science version 2.2.2 (Boston, Mass.) and the database is searched against the full SwissProt database version 57.5 (471472 sequences; 167326533 residues) or NCBI database version 20091013 (9873339 sequences; 3367482728 residues). The mass accuracy of the precursor ions are set to 2.0 Da if the data is acquired on an ion trap mass analyzer and the fragment mass accuracy is set to 0.5 Da. Modifications (variables) are methionine oxidation and carbamidomethyl cysteine. Two missed cleavages for the enzyme may be permitted. A decoy database is searched to determine the false discovery rate (FDR) and peptides may be filtered according to the FDR and proteins identify required bold red peptides. Protein identifications are checked manually and proteins with a Mascot score of 50 or higher with a minimum of two unique peptides from one protein having a −b or −y ion sequence tag of five residues or better are accepted.

Analytical Methods

Cell density is analyzed by measuring the optical density of the cell suspension after appropriate dilution at a wavelength of 600 nm ($OD_{600}$) with a spectrophotometer (Shimadzu, Model UV-1601, Columbia, Md.).

After removing of the bacterial cells by centrifuging at 13,000×g for 5 min, the clear fermentation broth is subjected to analysis of residual glucose and product concentrations. Glucose concentration is also measured using YSI model 2700 Select Biochemistry Analyzer (Yellow Springs, Ohio). Acetone, butanol and ethanol are determined using a gas chromatograph system (Shimadzu, Model GC-2014) equipped with a flame ionization detector and GC Solution Software. The column used is a fused silica capillary column (30 m×0.25 mm) (Stabilwax-DA, Restek, Bellefonte, Pa.). Nitrogen is used as the carrier gas with a flow rate of 12.5 ml/min. Both the injector and detector temperatures are set at 200° C. The oven temperature is programmed from 80° C. to 150° C. at a rate of 30° C./min after an initial holding time of 3 min, and then held at 150° C. for 3.7 min.

Genomic Sequencing

To further investigate the molecular basis for the acquired traits of the mutant, the complete genomes of the parent and mutant strains are sequenced via the Illumina Hiseq2000 (San Diego, Calif.) and then comparative genomic analysis, including SNP and InDel analysis, is conducted using the *Clostridium acetobutylicum* ATCC 824 genome sequence as a reference. In order to ensure the accuracy of follow-up analysis, several steps may be performed to filter the raw data. The steps may include: (1) removing reads with a certain proportion of Ns' bases or low complexity reads (10% as default, parameter setting at 7 bp); (2) removing reads with a certain proportion of low quality (≦Q20) bases. (40 bases as default, parameter setting at 40 bp); (3) removing adapter contamination (15 bp overlap between adapter and reads as default, parameter setting at 15 bp); (4) removing the last 15 bp of read1 with low quality; and (5) removing duplication contamination in a large size library if there is much duplication. As to reads with high heterozygosis or low sequence quality, the following steps may be taken (1) removing reads with significant poly-A structure (2) removing reads where k-mer frequency is 1. The short reads are then assembled into genomic sequences using SOAPdenovo (http://soap.genomics.org.cn/.Version: 1.05), or another assembler.

Gas Stripping

In order to increase fermentation productivity and facilitate the purification of butanol recovered from cultures, a gas stripping recovery process consisting of a stirred-tank reactor (fermentor) and a condenser is used. The stripping gas consists of $CO_2$ and hydrogen that are produced in the ABE fermentation and is bubbled through the reactor and circulated through the condenser with a peristaltic pump. The butanol-rich vapor is condensed by cooling at a temperature around 0° C. in the condenser and the condensate is collected in a flask immersed in a cold bath. Under favorable conditions and when the butanol concentration in the broth is higher than 6 g/L, the collected condensate undergoes phase separation, resulting in an upper organic phase containing ~65% (w/v) butanol and a lower aqueous phase containing ~8% (w/v) butanol. The lower aqueous phase may be fed to a second stage of gas stripping for further concentration. The butanol in the upper organic phase may be further purified to >99.9% by distillation.

EXAMPLES

The following examples are included to demonstrate preferred embodiments of the invention. It should be appreciated by those skilled in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Adaptive Engineering of *C. Acetobutylicum* Mutant Strain JB200

Figure 2:
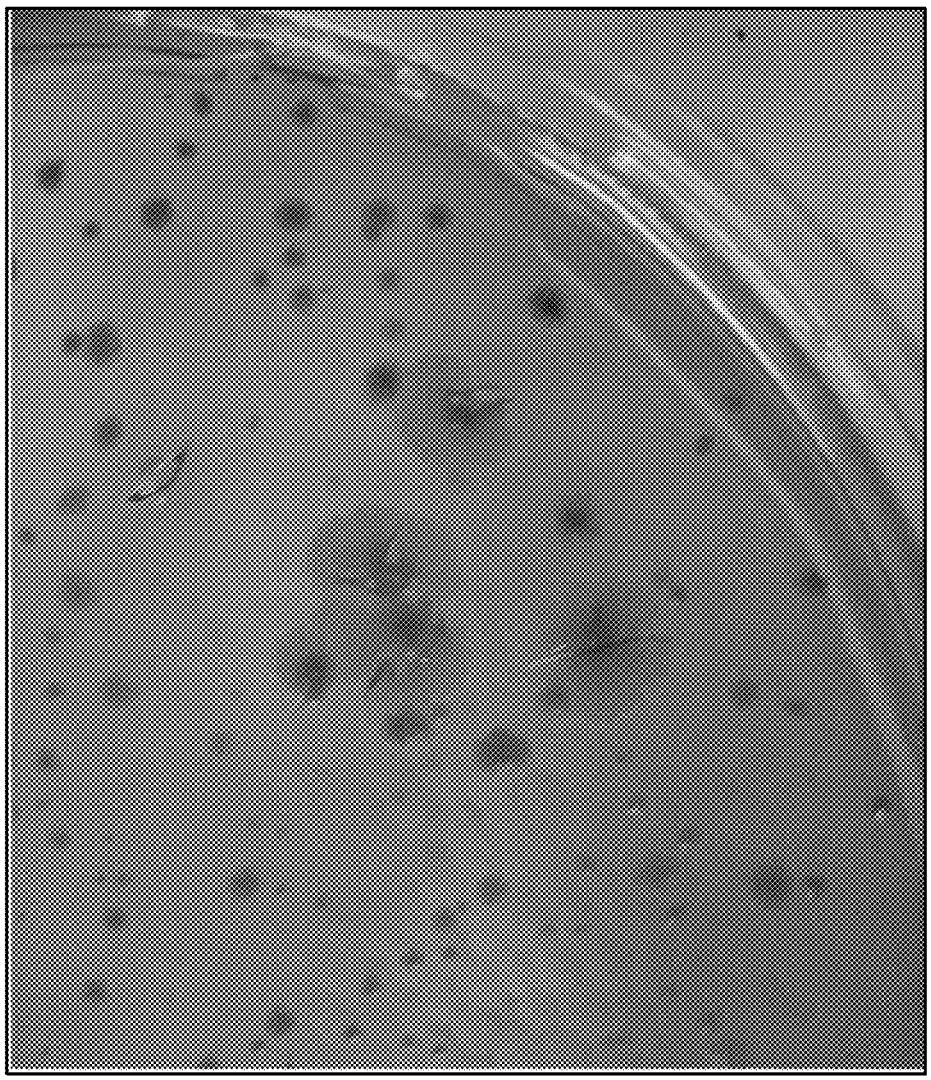
FIG. 2 is a picture of cell colonies on an agar plate.
Figure 3:
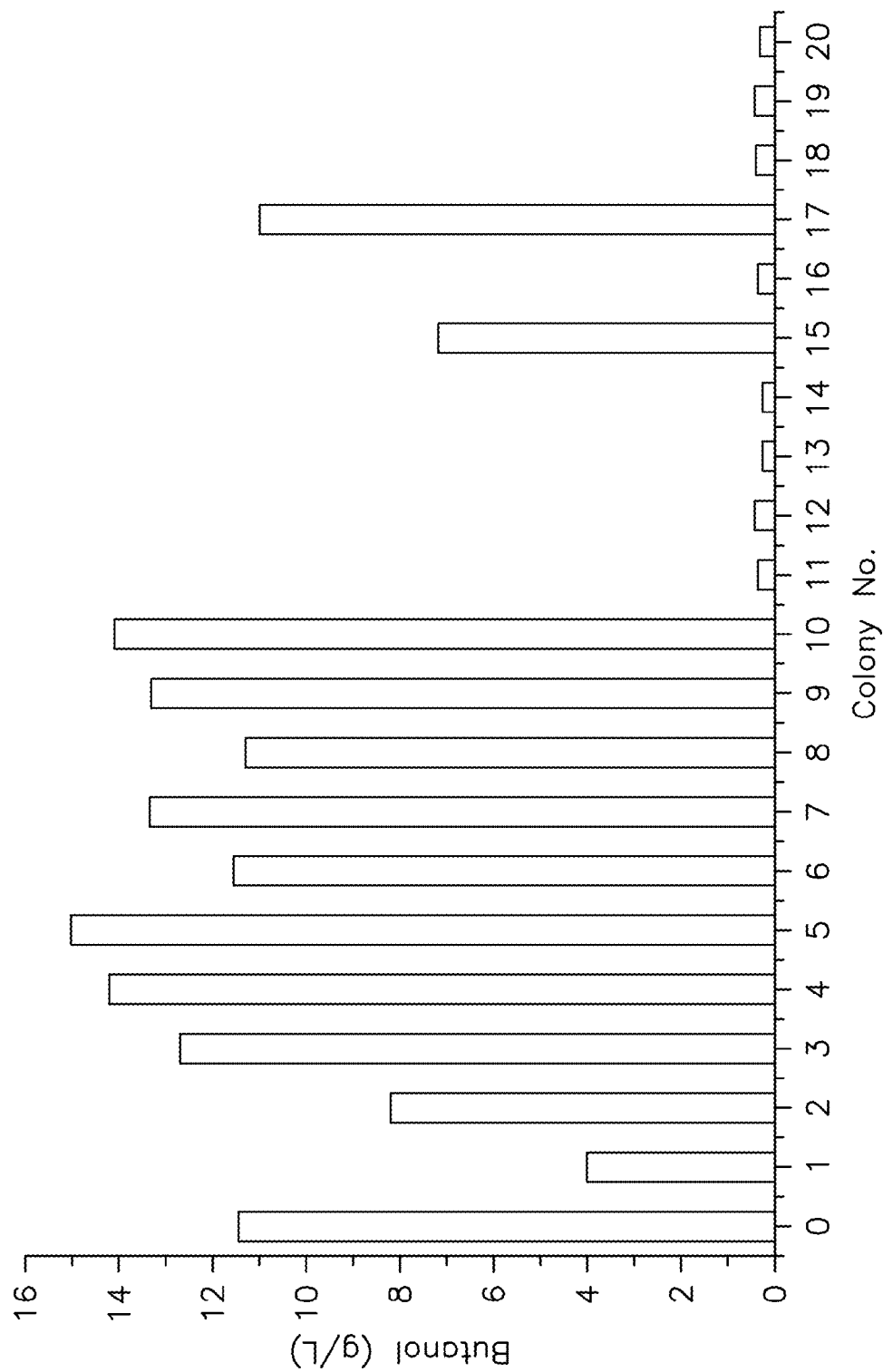
FIG. 3 is a chart of the comparative butanol production of *C. acetobutylicum* ATCC 55025 and 20 cell colonies after FBB adaptation.

*C. acetobutylicum* (ATCC 55025) cells were immobilized and cultured in a FBB system for over 40 days. The cells of this parental strain were periodically exposed to a high butanol concentration, in order to drive the adaptation towards a higher butanol tolerance. During this period, butyric acid and neutral red were also applied to strengthen acid assimilation and push the electron and carbon flow towards butanol. Cells taken from the fermentor were cultured on CGM agar plates for screening and isolation of hyper-butanol producers. After culturing for several days, cells formed colonies of various sizes on the agar plates. Referring to FIG. 2, a picture of the cell colonies is shown. Colonies of different sizes were randomly selected and tested for their butanol production abilities in batch fermentations carried out in 50-ml centrifuge tubes containing P2 (8% glucose) medium. FIG. 3 shows the comparative butanol production abilities of 20 different colonies resulting from the FBB adaptation (1-10, larger colonies, 11-20, smaller colonies) as well as the butanol production capability of parental strain ATCC 55025 (without FBB adaptation). In general, the culture tubes inoculated with cells from large colonies produced more butanol, while culture tubes inoculated with cells from small colonies did not produce much butanol. The results suggested that a heterogeneous population existed in the FBB and the adaptation process generated butanol-tolerant strains but not all of them could produce (more) butanol. Among the larger colonies, cells from one colony, designated as JB200, produced the highest amount of butanol (15 g/L). In the same experiment, the control culture tubes inoculated with the parental strain (without FBB adaptation) produced only 11.3 g/L.

To further investigate the performance of JB200 strain, JB200 and its parental strain were cultured in the P2 medium (10-12% glucose) in a stirred-tank bioreactor (free cell fermentation) and the FBB with the pH controlled at 5.0 or higher. The results are summarized in Table 2 below.

TABLE 2

Comparison of Fermentation Kinetics of Parental Strain
(ATCC 55025) and Mutant Strain JB200

| Strain and system | Butanol | | | Total solvent | | |
|---|---|---|---|---|---|---|
| | Titer (g/L) | Yield (g/g) | Productivity (g/L · h) | Titer (g/L) | Yield (g/g) | Productivity (g/L · h) |
| Free-cell fermentation in stirred-tank bioreactor | | | | | | |
| Parental strain (ATCC 55025) | 12.5 | 0.20 | 0.23 | 22.6 | 0.36 | 0.42 |
| Mutant strain JB200 | 21.0 | 0.24 | 0.26 | 36.0 | 0.42 | 0.45 |
| Immobilized-cell fermentation in fibrous bed bioreactor | | | | | | |
| Parental strain | 15.2 | 0.20 | 0.28 | 27.5 | 0.36 | 0.51 |
| Mutant strain JB200 | 24.1 | 0.26 | 0.25 | 40.3 | 0.43 | 0.42 |
| JB200 (high cell density) | 28.2 | 0.24 | 0.24 | 50.7 | 0.40 | 0.40 |

Figure 4:
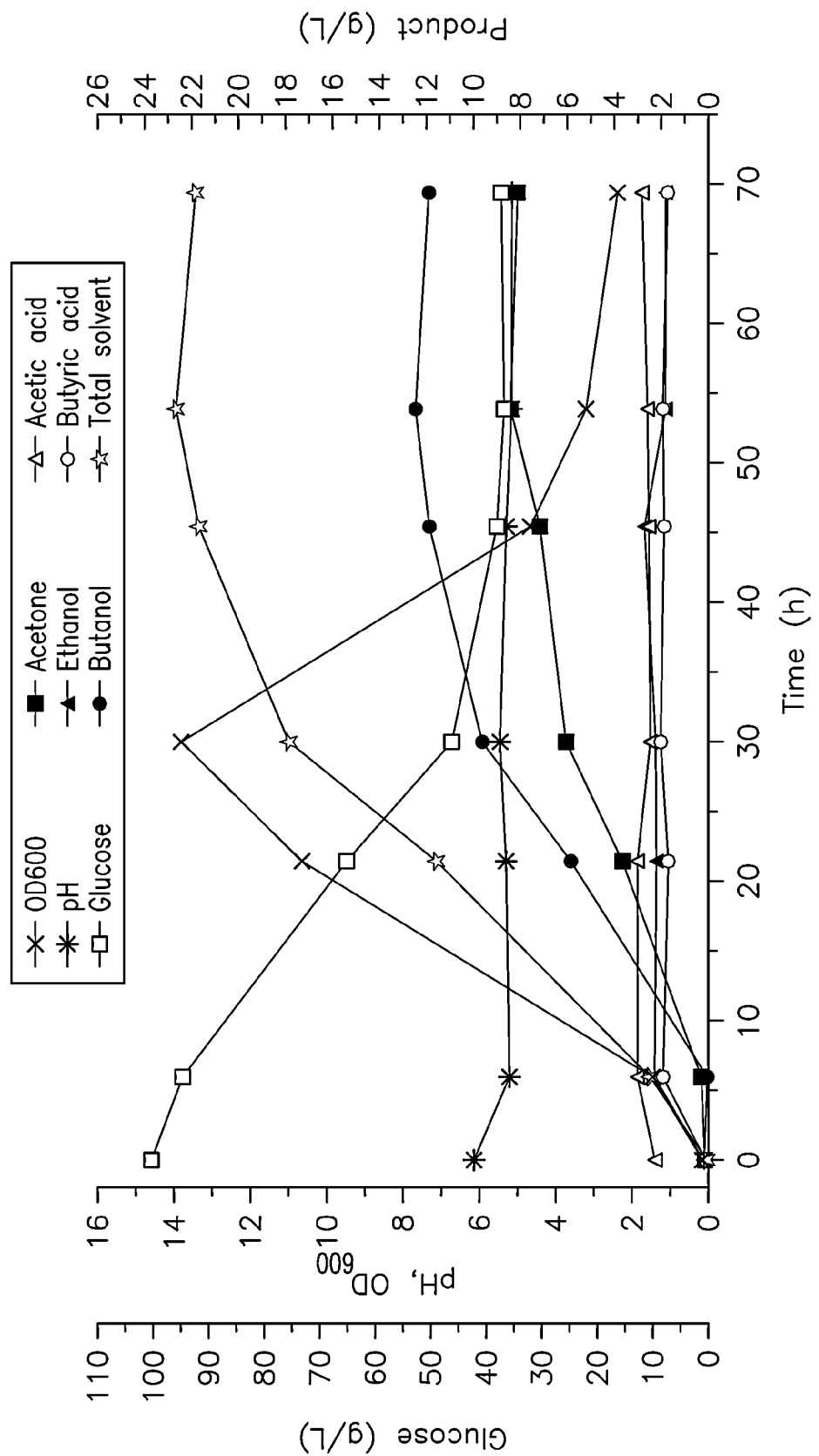
FIG. 4 is a chart showing fermentation kinetics of *C. acetobutylicum* ATCC 55025 in free-cell fermentation in a stirred tank fermentor.
Figure 5:
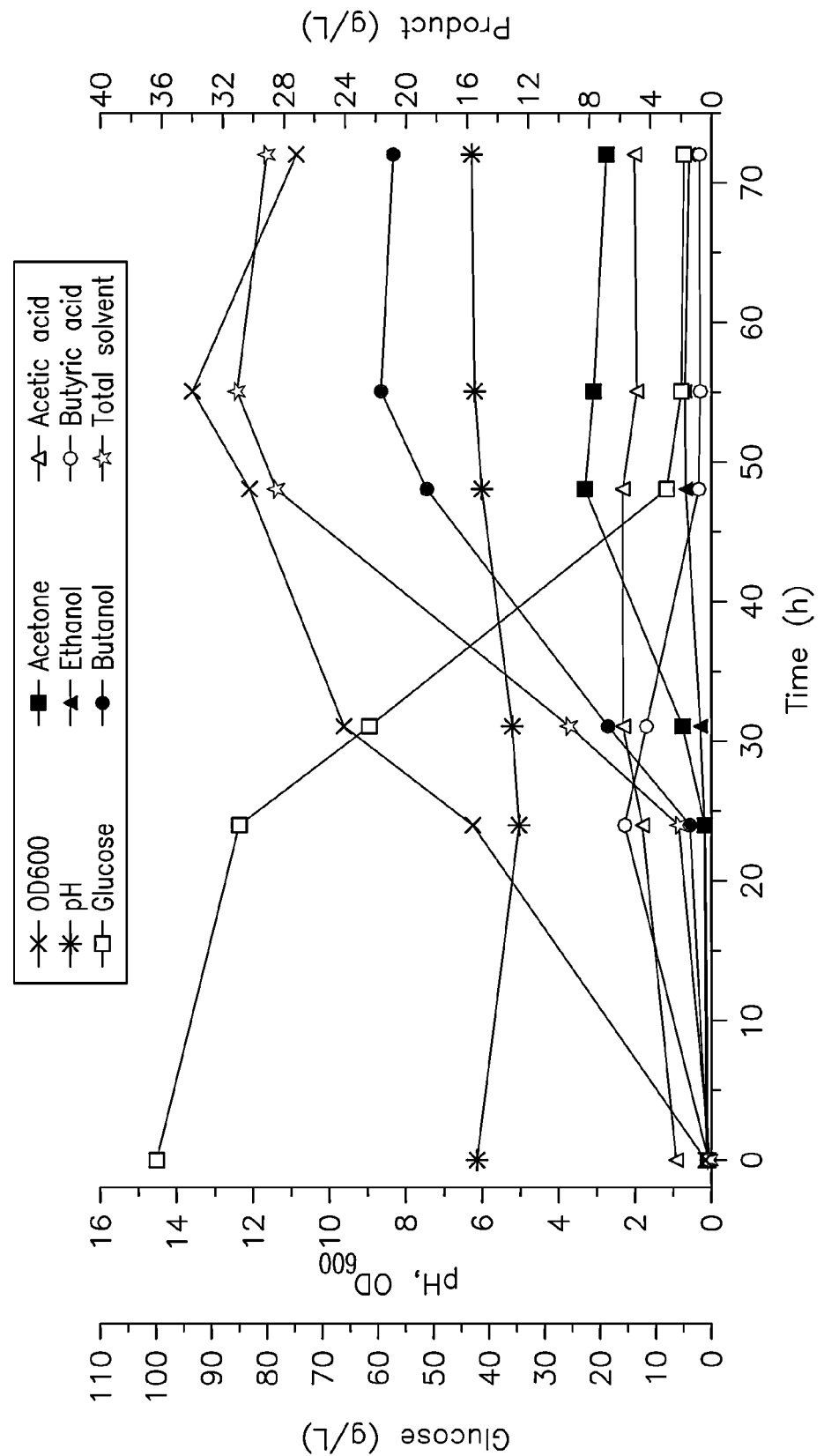
FIG. 5 is a chart showing fermentation kinetics of the JB200 mutant strain in free-cell fermentation in a stirred tank fermentor.

In free cell fermentations with JB200, butanol and total solvent titers as high as 21.7 g/L and 31.0 g/L were achieved, which were 74% and 37% higher than those of the fermentation with the parental strain. At the same time, significant increases in butanol yield and productivity were also observed. FIGS. 4 and 5 show the batch fermentation kinetics of the parental strain and JB200, respectively, in conventional free-cell fermentation in a stirred tank fermentor.

As can be seen in FIG. 5, JB200 showed slower cell death or lyses with an extended stationary phase, which allowed the fermentation to continue to produce more butanol. In contrast, the parental strain suffered from rapid cell lyses (death) as indicated by the rapid $OD_{600}$ decrease once the butanol concentration reached 10 g/L (see FIG. 4). The parental strain produced a viscous fermentation broth with a lot of foaming, presumably caused by dead cells and cell debris, toward the late exponential phase. In contrast, the fermentation broth remained fluidic (non-viscous) in the fermentation with JB200. These observations indicated the robustness of the mutant strain JB200 under various stresses in the stationary phase.

Figure 6:
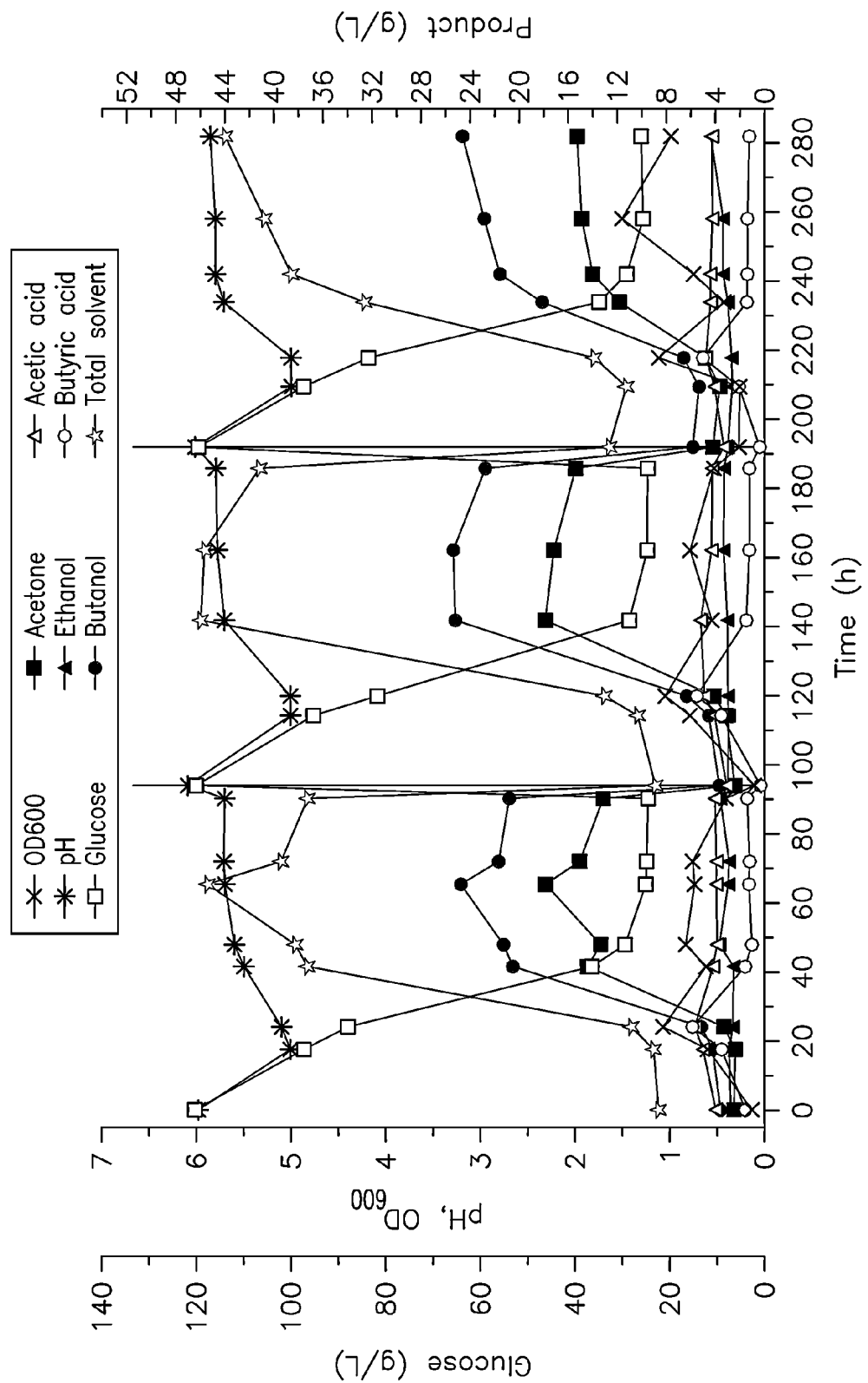
FIG. 6 is a chart showing the kinetics of three consecutive batch fermentations with JB200 in the FBB.

Similar improvements in the final butanol titer and yield were also observed in the FBB fermentation with JB200 (see Table 2). The highest butanol titer of ~28.2 g/L was obtained in the fermentation with a higher cell density with two FBB's. However, the butanol productivity suffered slightly in order to reach the high butanol titer by extending the fermentation period. As shown in FIG. 6, the culture showed consistent fermentation kinetics in three consecutive batches each reaching a final butanol concentration of ~25 g/L in 50-80 h. The stable performance of the mutant strain JB200 in FBB fermentations is advantageous for butanol production.

Figure 7:
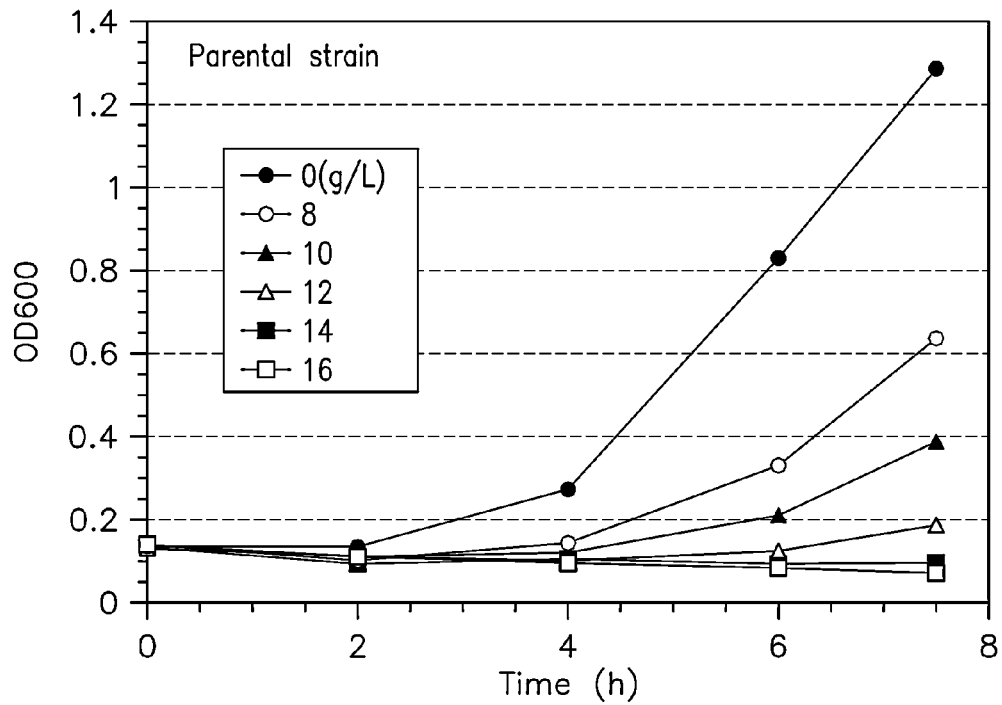
FIG. 7 is a chart showing the inhibition effect of butanol on cell growth of *C. acetobutylicum* ATCC 55025.
Figure 8:
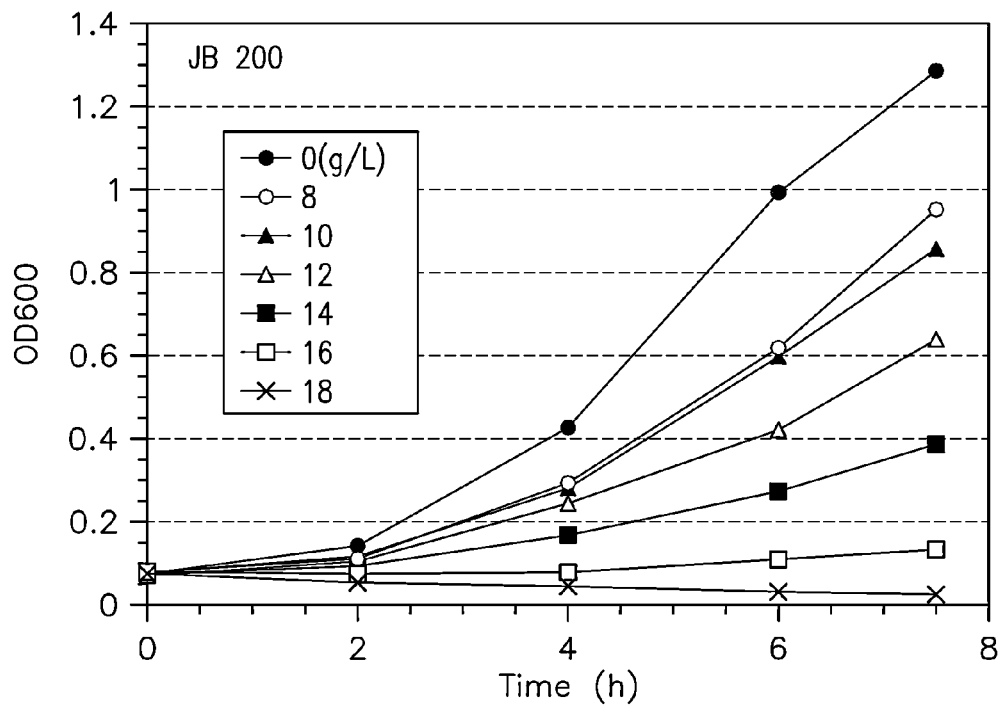
FIG. 8 is a chart showing the inhibition effect of butanol on cell growth of JB200.
Figure 9:
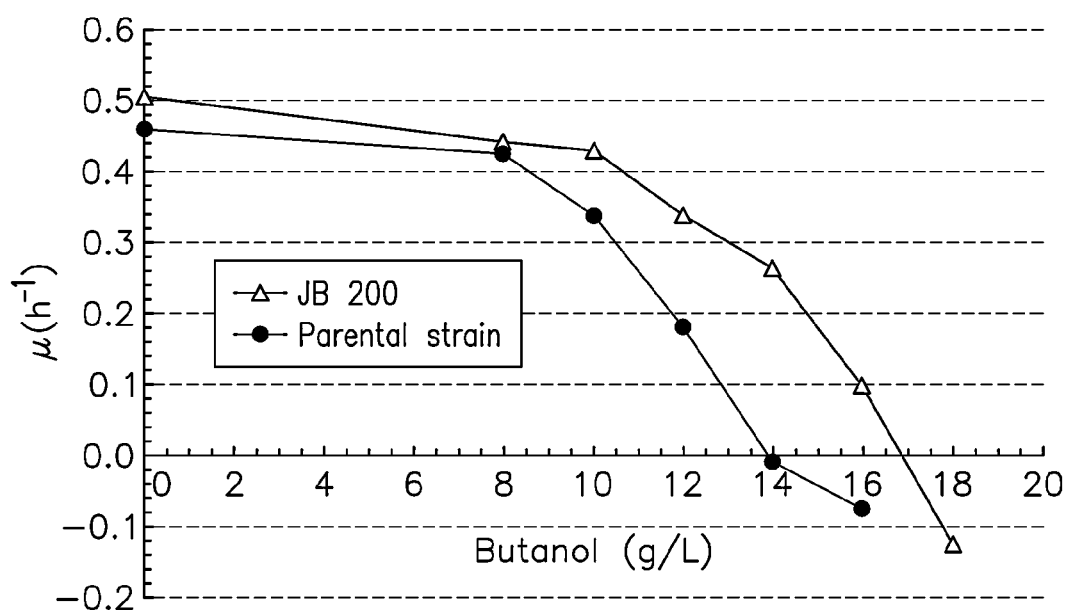
FIG. 9 is a chart showing the effect of butanol on the specific growth rate of JB200 and *C. acetobutylicum* ATCC 55025.
Figure 10A:
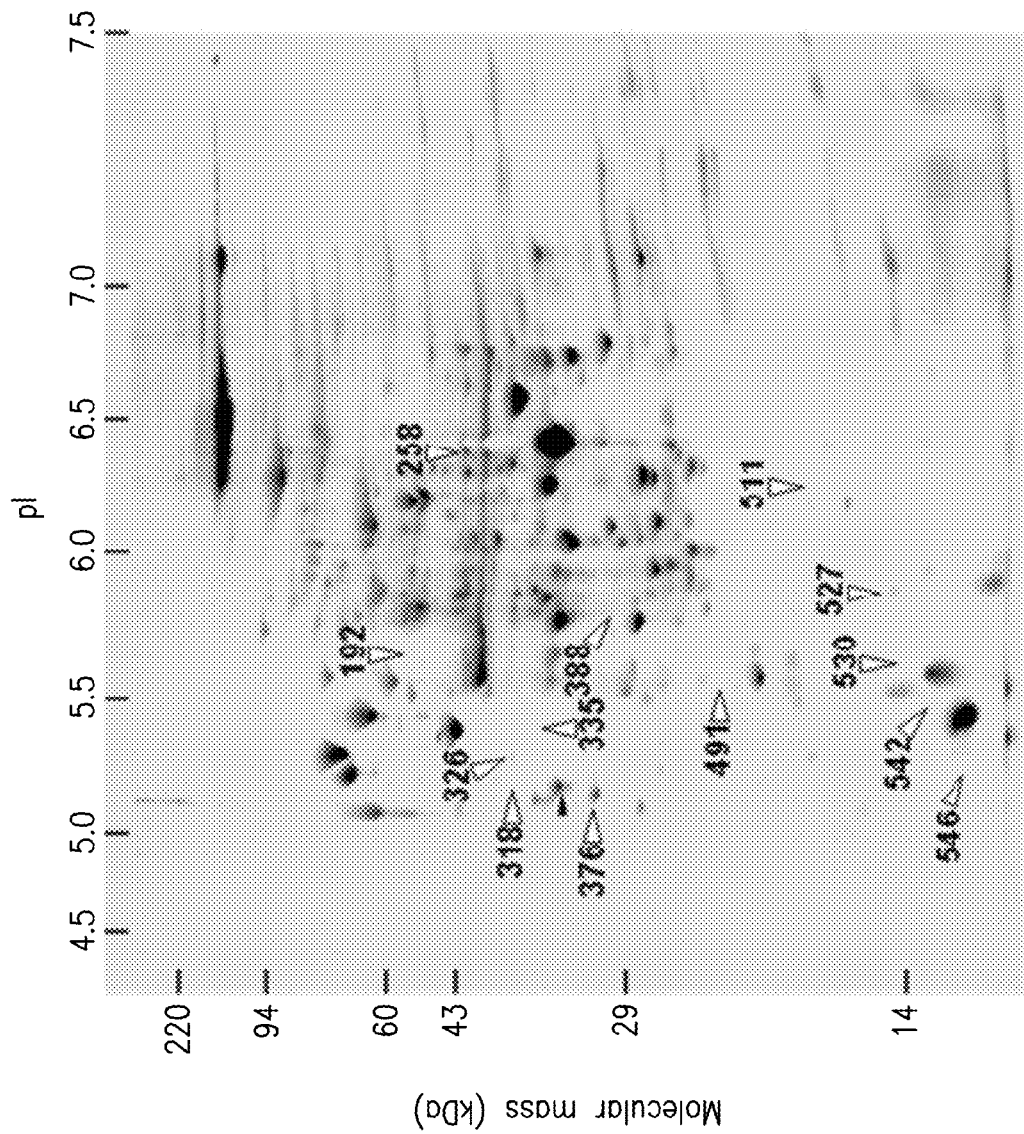
FIGS. 10*a*, 10*b*, 10*c*, and 10*d* display images of 2-D gel electrophoresis identifying protein spots.
Figure 10B:
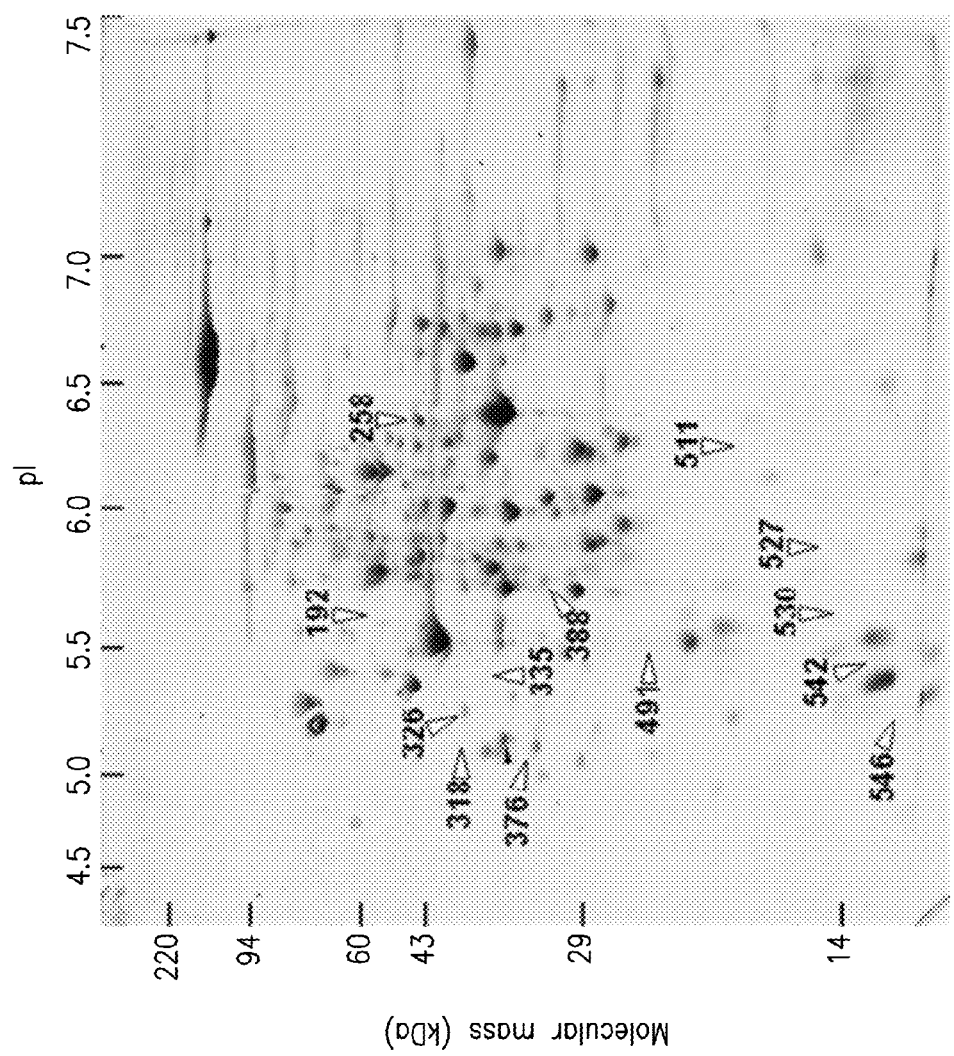
Figure 10C:
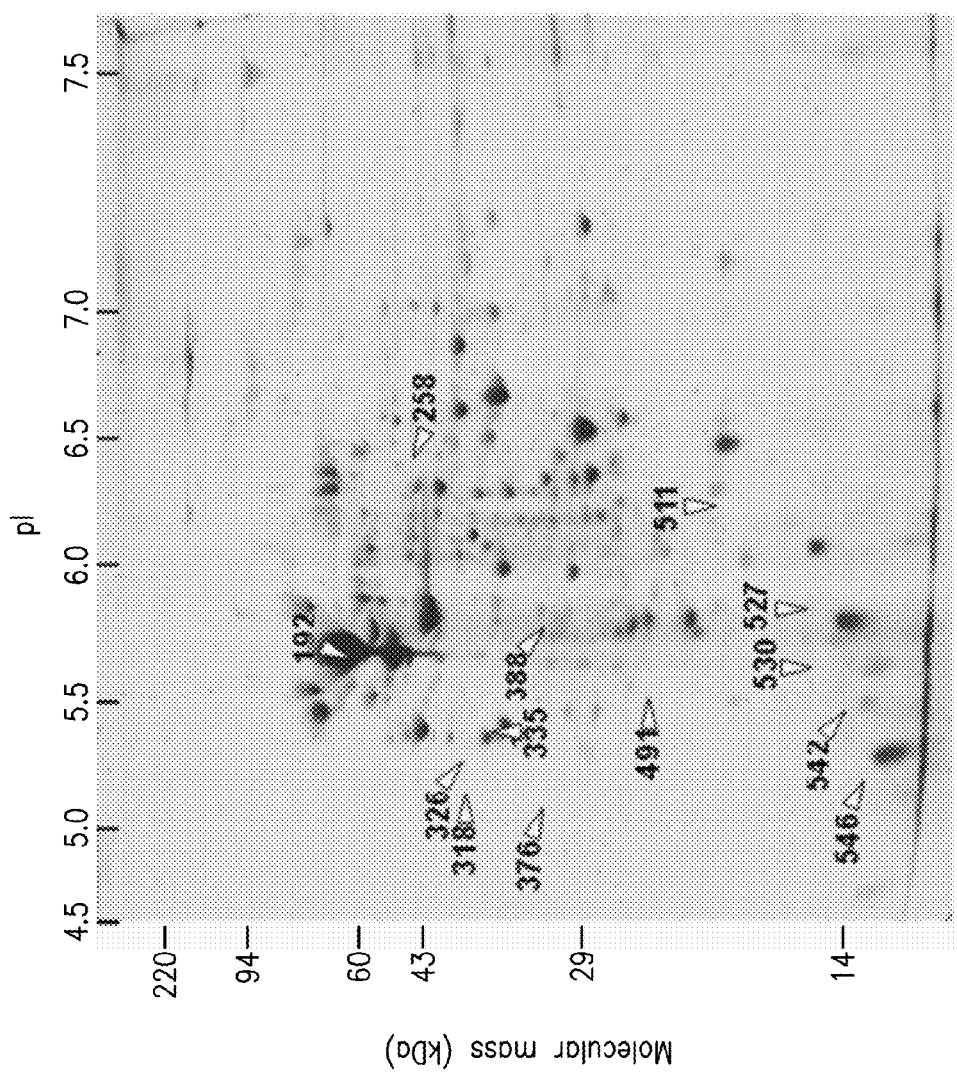
Figure 10D:
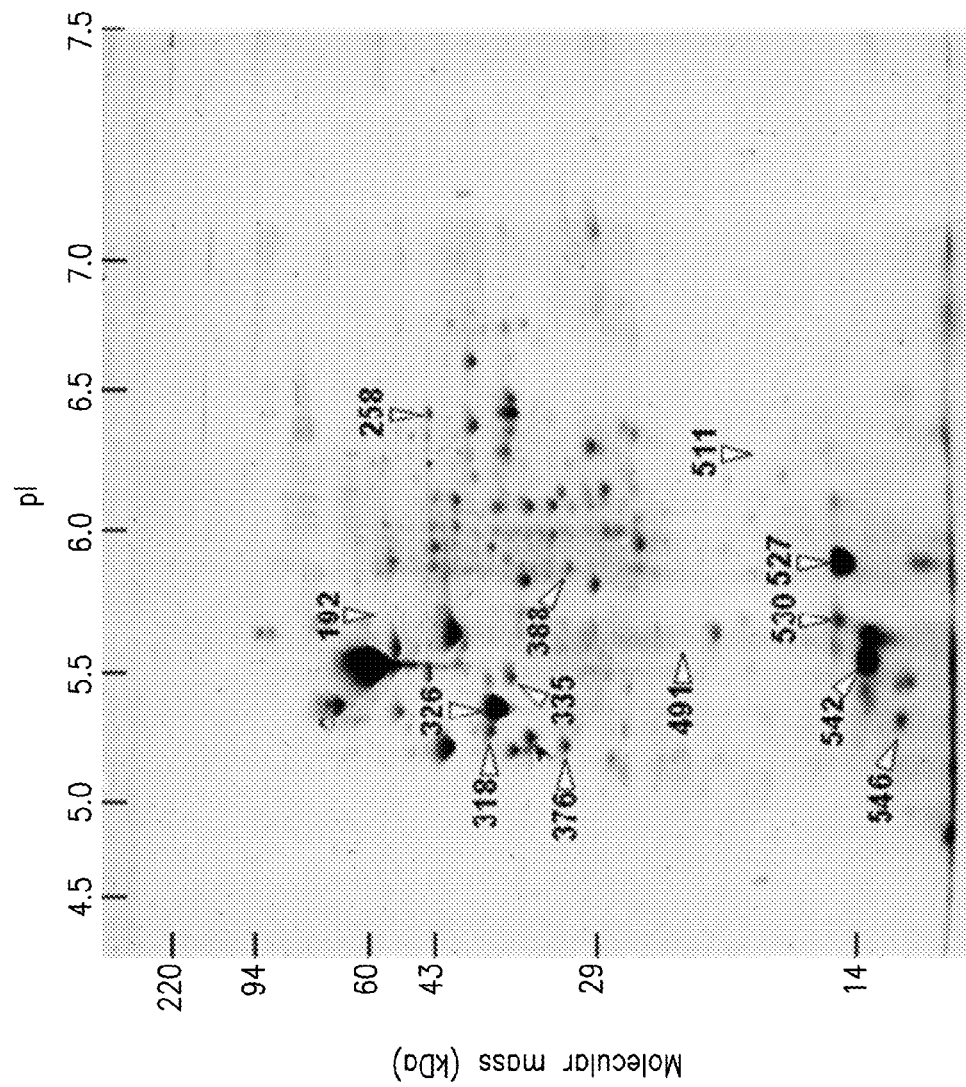

Butanol tolerances of JB200 and its parental strain were evaluated by studying the effect of butanol on cell growth in CGM media containing various amounts of butanol. Referring to FIGS. 7 and 8, inhibition effect of butanol on cell growth in the serum bottle cultures is shown for the parental strain (ATCC 55025) (FIG. 7) and JB200 (FIG. 8), respectively. Referring to FIG. 9, the effect of butanol on the specific growth rate ($\mu$) of JB200 and the parental strain is shown. Compared with the parental strain, JB200 had higher specific growth rates at all butanol concentrations studied. Also, whereas cell growth of the parental strain stopped when the butanol concentration was higher than 12 g/L, JB200 still grew at 16 g/L butanol. Butanol inhibition tests on three other solventogenic *Clostridia* strains (ATCC 824, NCIMB 8052, BA 101) showed that none of them could grow in the presence of 12 g/L butanol. JB200 has a higher butanol tolerance than its parental strain and the other solventogenic *Clostridia* strains tested. The higher butanol tolerance of JB200 can be partially attributed to its comparatively higher saturated long-chain fatty acids content in the cell membrane. Table 3 below charts the fatty acid contents in the cell membranes of the parental strain and mutant JB200 during both the early exponential phase and late stationary phase.

TABLE 3

Fatty acid contents in cell membranes of parental strain (ATCC 55025) and mutant (JB200) during the early exponential phase and late stationary phase.

| | Parental strain (ATCC 55025) | | Mutant strain (JB200) | |
|---|---|---|---|---|
| Fatty acid compositions (%) | Exponential phase | Stationary phase | Exponential phase | Stationary phase |
| Saturated fatty acids & derivatives | 65.52 | 72.21 | 64.98 | 78.41 |
| 10:0 and 12:0 | 0 | 0.55 | 0 | 0.56 |
| 14:0 and 14:0 DMA | 6.74 | 3.1 | 4.75 | 3.35 |
| 16:0, 16:0 DMA and 16:0 aldehyde | 55.11 | 58.98 | 55.28 | 61.53 |
| 18:0, 18:0 DMA and 18:0 aldehyde | 3.67 | 9.58 | 4.95 | 12.97 |
| Unsaturated fatty acids & derivatives | 33.14 | 27.14 | 33.83 | 21.08 |
| 13:1 and 14:1 DMA | 0.72 | 0.34 | 0.37 | 0.42 |
| 16:1 and 16:1 DMA | 7.57 | 3.11 | 5.81 | 2.22 |

TABLE 3-continued

Fatty acid contents in cell membranes of parental strain (ATCC 55025) and mutant (JB200) during the early exponential phase and late stationary phase.

| Fatty acid compositions (%) | Parental strain (ATCC 55025) | | Mutant strain (JB200) | |
|---|---|---|---|---|
| | Exponential phase | Stationary phase | Exponential phase | Stationary phase |
| 17:2, 17:0 cyc and 17:0 cyc DMA | 3.89 | 2.49 | 2.56 | 1.12 |
| 18:1 and 18:1 DMA | 4.65 | 2.32 | 5.87 | 2.17 |
| 19:0 cyc and 19:0 cyc DMA | 16.21 | 18.88 | 19.22 | 15.15 |
| Unsaturated FA/Saturated FA | 0.51 | 0.38 | 0.52 | 0.27 |

DMA: dimethyl acetal;
cyc: cyclopropane

The membrane fatty acid contents in cells from both the early exponential phase and late stationary phase were analyzed with gas chromatography. In general, more saturated fatty acids and derivatives were found in cells in the late stationary phase. Although both the parental strain and JB200 had similar fatty acid contents in the exponential phase, for cells in the stationary phase JB200 had significantly higher amounts of saturated fatty acids, especially the longer ones (16:0 and 18:0), which contributed to cell's ability to maintain its membrane rigidity and integrity. The ratio of unsaturated to saturated fatty acids (and derivatives) was much lower in JB200 (0.27) than in the parental strain (0.38). This ratio is a common measure of membrane rigidity (stability), with a lower ratio indicating higher membrane rigidity (stability).

Comparative Protein Analysis

To investigate the molecular basis for the acquired traits of the mutant, the proteomic profiles of the mutant JB200 and its parental strain during early exponential phase and late stationary phase were analyzed using 2-D gel electrophoresis. Proteins with dramatic difference in their expression levels were identified and classified based on their potential roles.

Figure 11:
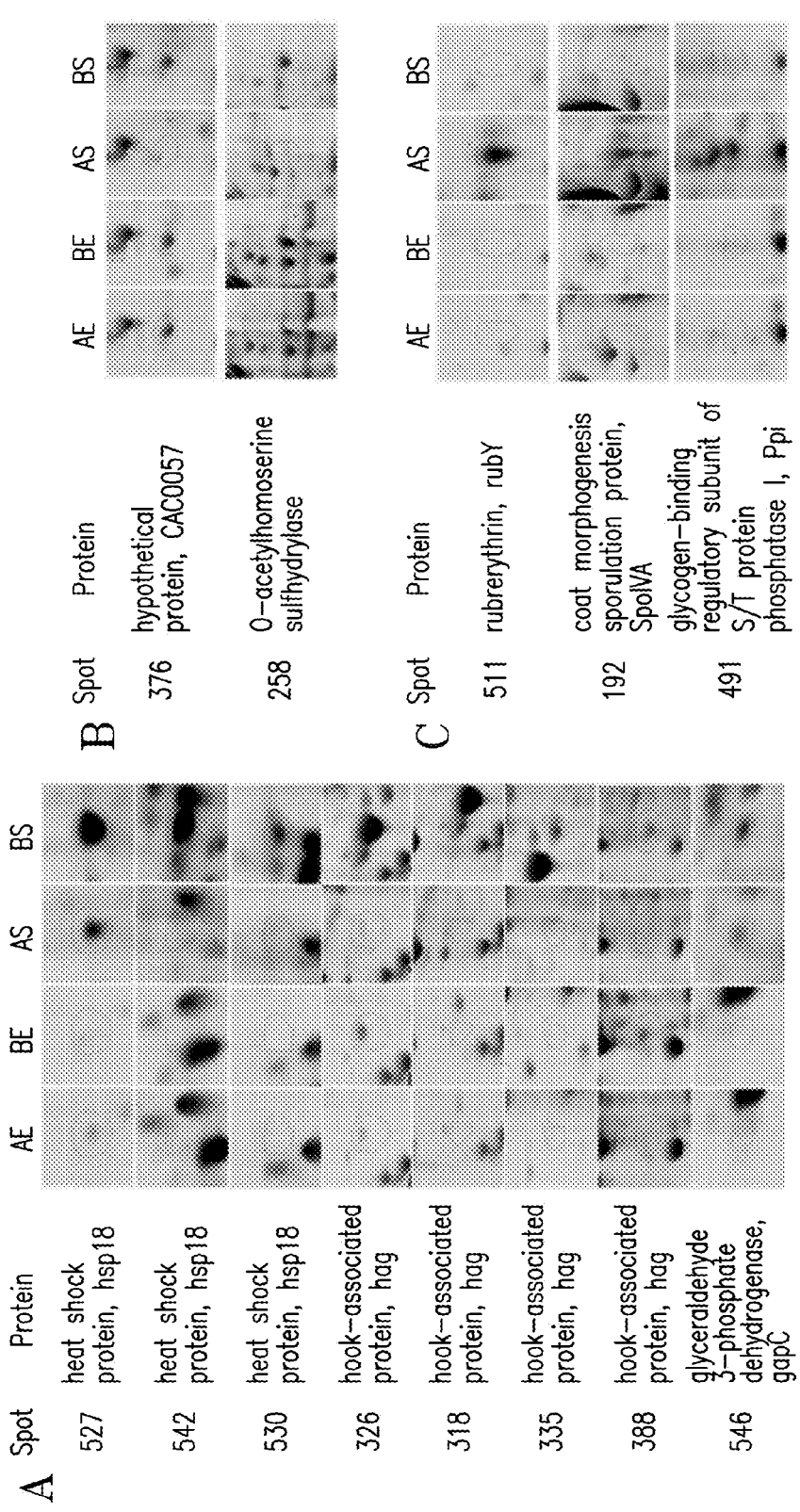
FIG. 11 displays expanded regions of protein spots identified in FIG. 10.

Referring to FIG. 10, images of the 2-DE of the parental strain and mutant JB200 during butanol fermentation are shown. Panels A and C show the parental strain in exponential and stationary phase, respectively (AE and AS sample). Panels B and D show the JB200 mutant in exponential and stationary phase, respectively (BE and BS sample). The pI range and the approximate molecular mass determined by the protein markers are shown. Some spots with obvious difference in the expression levels are indicated by arrows and their spot ID numbers. These protein spots were identified by LC-MS/MS. Referring to FIG. 11, expanded regions of the identified protein spots are shown. These proteins were classified into three groups: Panel A: proteins highly overexpressed in JB200 mutant stationary phase cells; Panel B: proteins down-regulated in wild-type but not in JB-200 mutant cells upon entering into stationary phase; and Panel C: proteins overexpressed in wild-type but not in JB200 mutant cells upon entering into stationary phase. Table 4 below also sets forth the characteristics of the identified proteins.

TABLE 4

Proteins with different expression levels for wild-type and mutant cells in exponential and stationary phases during ABE fermentation.

| Protein identified | Spot | Sequence coverage (%) | MW calc (kDa) | MW app (kDa) | pI calc | pI app |
|---|---|---|---|---|---|---|
| Highly overexpressed proteins in JB200 mutant stationary phase cells | | | | | | |
| Heat shock protein, hsp18 (CAC3714) | 527 | 84 | 17.7 | 15 | 5.27 | 5.81 |
| | 542 | 80 | 17.7 | 13 | 5.27 | 5.50 |
| | 530 | 64 | 17.7 | 15 | 5.27 | 5.62 |
| Hook-associated protein, flagellin family, hag (CAC2203) | 326 | 48 | 29.5 | 37 | 5.78 | 5.32 |
| | 318 | 39 | 29.5 | 38 | 5.78 | 5.25 |
| | 335 | 44 | 29.5 | 36 | 5.78 | 5.47 |
| | 388 | 51 | 29.5 | 31 | 5.78 | 5.80 |
| Glyceraldehyde 3-phosphate dehydrogenase, gapC (CAC0709) | 546 | 29 | 36.0 | 12 | 5.93 | 5.30 |
| Protein expression down-regulated in wild-type but not in JB200 in stationary phase | | | | | | |
| Hypothetical protein (CAC0057) | 376 | 56 | 31.2 | 31 | 4.67 | 5.20 |
| 0-acetylhomoserine sulfhydrylase (CAC2783) | 258 | 49 | 46.3 | 45 | 5.91 | 6.40 |
| Proteins overexpressed in IO-type but not in JB200 in stationary phase | | | | | | |
| Rubrerythrin, rubY (CAC2575) | 511 | 51 | 22.4 | 19 | 6.36 | 6.19 |
| Coat morphogenesis sporulation protein, SpoIVA (CAC1713) | 192 | 44 | 56.3 | 58 | 5.14 | 5.60 |

TABLE 4-continued

Proteins with different expression levels for wild-type and mutant cells in exponential and stationary phases during ABE fermentation.

| Protein identified | Spot | Sequence coverage (%) | MW calc (kDa) | MW app (kDa) | pI calc | pI app |
|---|---|---|---|---|---|---|
| Glycogen-binding regulatory subunit of S/T protein phosphatase I, Ppi (CAP0129) | 491 | 54 | 28.1 | 24 | 6.08 | 5.56 | pI: Isoelectric point;
calc: calculated value based on the amino acid sequence;
app: apparent value based on the spot location on the 2D gel.

Eight proteins with the highest expression in stationary-phase JB200 cells were identified. Three spots were small heat shock protein (hsp18) and four were hook-associated protein (hag). The last one is glyceraldehyde 3-phosphate dehydrogenase (gapC).

During the transition from exponential phase to stationary phase, up-regulated expression of hsp18 in both parent and mutant cells occurred. Abundant expression of a hood-associated protein (hag) in the mutant during solventogenesis also occurred. The expression levels of O-acetylhomoserine sulf-hydrylase and hypothetical protein CAC0057 were dramatically reduced in wild-type cells, while remaining unchanged or slightly increased in mutant cells, during the transition from exponential to stationary phase.

Three proteins (rubrerythrin, SpoIVA and Ppi (CAP0129)) were highly expressed in the wild-type cells during the stationary phase but were not expressed in mutant cells. The different expression levels of these proteins suggested that wild-type cells entered sporulation and thus stopped producing butanol in the late stationary phase, whereas mutant cells remained in the active, vegetative state.

Figure 12:
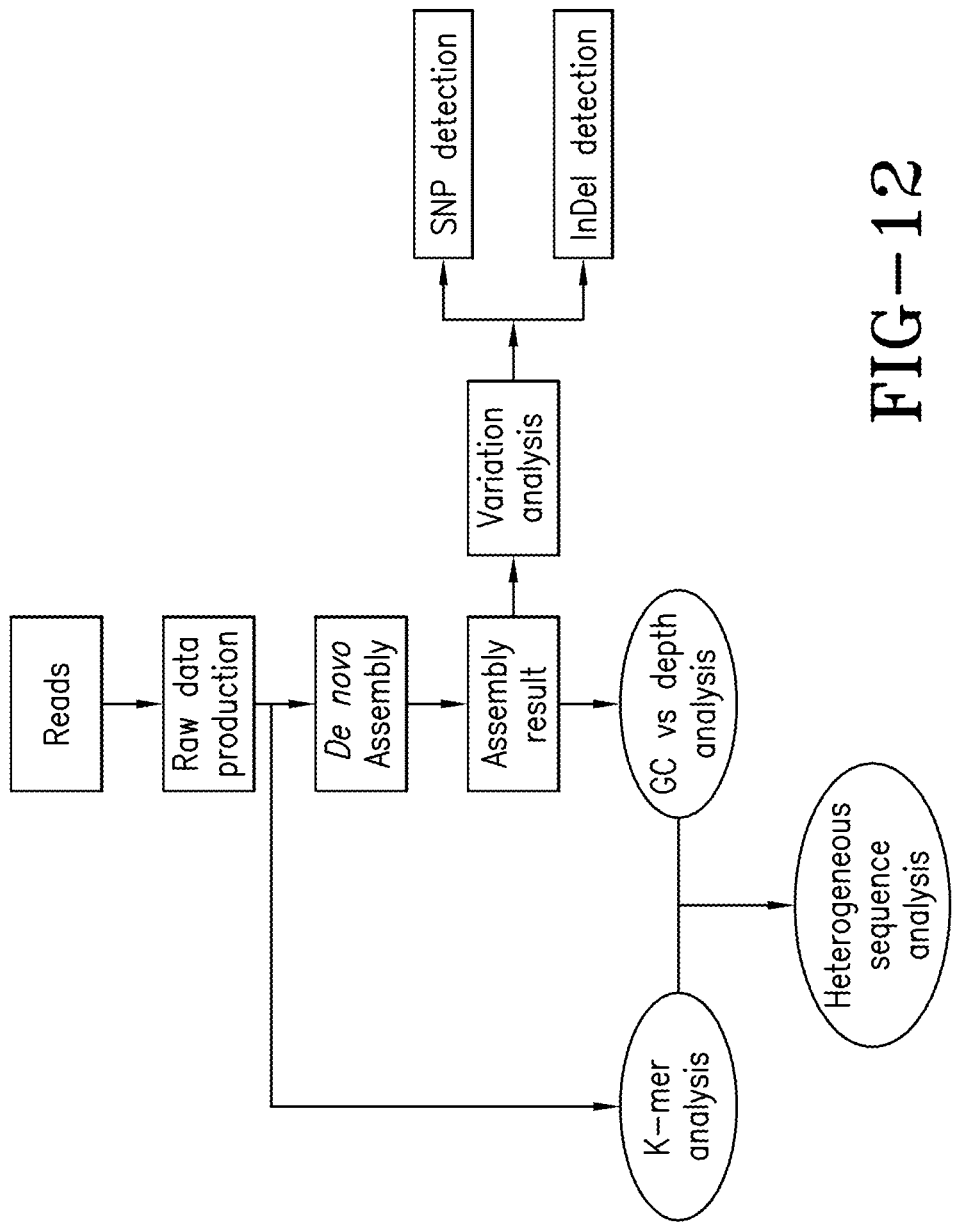
FIG. 12 shows a chart of the pipeline of genome sequencing and bioinformatics analysis used.

Comparative genomic analysis, including SNP and InDel analysis, was conducted using *Clostridium acetobutylicum* ATCC 824 genome sequence as a reference. FIG. 12 shows the pipeline of genome sequencing and bioinformatics analysis used. High-throughput Illumina sequencing technology was used to conduct paired-end sequencing for DNA samples. A 350 bp library with expected data of 480M was constructed. Thirty-three scaffolds composed of 67 contigs were assembled for the chromosome DNA of ATCC 55025 and 1 scaffold composed of 2 contigs was assembled for the plasmid DNA. For JB200, 33 scaffolds composed of 52 contigs were assembled for the chromosome DNA and 1 scaffold composed of 2 contigs was assembled for the plasmid DNA. The assembly results of ATCC 55025 and JB200 samples are summarized in Tables 5 and 6 below:

TABLE 5

Assembly results of ATCC 55025 sample

| | Chromosome | | Plasmid | |
|---|---|---|---|---|
| | Scaffold | Contig | Scaffold | Contig |
| Total number | 33 | 67 | 1 | 2 |
| Total length (bp) | 3,885,382 | 3,881,299 | 191,822 | 191,748 |
| N50 (bp) | 377,130 | 298,955 | 191,822 | 147,604 |
| N90 (bp) | 54,626 | 46,429 | 191,822 | 44,144 |
| Max length (bp) | 873,694 | 647,070 | 191,822 | 147,604 |
| Min length (bp) | 654 | 7 | 191,822 | 44,144 |
| Sequence GC (%) | 30.68 | 30.68 | 30.91 | 30.91 |

TABLE 6

Assembly results of JB200 sample

| | Chromosome | | Plasmid | |
|---|---|---|---|---|
| | Scaffold | Contig | Scaffold | Contig |
| Total number | 33 | 52 | 1 | 2 |
| Total length (bp) | 3,884,742 | 3,882,721 | 191,853 | 191,766 |
| N50 (bp) | 463,412 | 231,331 | 191,853 | 115,350 |
| N90 (bp) | 59,342 | 59,342 | 191,853 | 76,416 |
| Max length (bp) | 947,159 | 709,718 | 191,853 | 115,350 |
| Min length (bp) | 685 | 62 | 191,853 | 76,416 |
| Sequence GC (%) | 30.68 | 30.68 | 30.92 | 30.92 |

In order to determine the genus of the mutant JB200 and its parent strain, the assembled genome sequences of ATCC 55025 and JB200 were used to blast genomes of different *Clostridium* species by SOAPcoverage. The results are shown in Table 7 below:

TABLE 7

Results of SOAPcoverage with different genomes.

| | SOAPcoverage | | | | | |
|---|---|---|---|---|---|---|
| | *C. acetobutylicum* | | | | *C. beijerinckii* | |
| | Chromosome | | Plasmid | | | |
| Sample ID | Cover/Genome (bp/bp) | Rate (%) | Cover/Genome (bp/bp) | Rate (%) | Cover/Genome (bp/bp) | Rate (%) |
| ATCC 55025 | 3,940,428/ 3,940,880 | 99.99 | 191,939/ 192,000 | 99.97 | 27,987/ 6,000,632 | 0.47 |
| JB200 | 3,940,520/ 3,940,880 | 99.99 | 191,940/ 192,000 | 99.97 | 67,004/ 6,000,632 | 1.12 |

The blast results in Table 7 show that these two strains belong to *Clostridium acetobutylicum* species, but not *Clostridium beijerinckii* as classified by the ATCC. Both strains have a megaplasmid, as that in *C. acetobutylicum* ATCC 824. Sequencing reads of these strains cover almost all chromosome (99.99%) and plasmid (99.97%) sequences, indicating that these two strains are highly similar to *C. acetobutylicum* ATCC 824. Based on the blast results, the genome sequence of *C. acetobutylicum* ATCC 824 was used as reference for variation analysis. 143 SNPs were detected in the sample of ATCC 55025. 138 SNPs are in chromosome and 5 are in plasmid, as shown in Table 8 below:

TABLE 8

SNP annotation of ATCC 55025 sample

| Sample name | Region | Mutation type | Number |
|---|---|---|---|
| ATCC 55025 chromosome | CDS | Stop codon non-synonymous | 4 |
| | | Nonsense | 1 |
| | | Synonymous in coding region | 21 |
| | | Nonsynonymous in coding region | 91 |
| | Intergenic | — | 21 |
| | Total | — | 138 |
| ATCC 55025 plasmid | CDS | Nonsynonymous in coding region | 5 |
| | Total | — | 5 |

As shown in Table 8, 117 SNPs fall into coding regions and 21 into intergenic regions in chromosome, while all SNPs in plasmid fall into coding regions. For JB200, 147 SNPs were detected, among which 142 in chromosome and 5 in plasmid, as shown in Table 9 below.

TABLE 9

SNP annotation of JB200 sample

| Sample name | Region | Mutation type | Number |
|---|---|---|---|
| JB200 chromosome | CDS | Stop codon non-synonymous | 4 |
| | | Nonsense | 1 |
| | | Synonymous in coding region | 22 |
| | | Nonsynonymous in coding region | 94 |
| | Intergenic | — | 21 |
| | Total | — | 142 |
| JB200 plasmid | CDS | Nonsynonymous in coding region | 5 |
| | Total | — | 5 |

As shown in Table 9, 121 SNPs fall into coding regions and 21 into intergenic regions in chromosome, and also all SNPs in plasmid fall into coding regions. As shown in Table 10 below, 17 and 20 InDels were found in ATCC 55025 and JB200 mutant chromosome, respectively. For both strains, no InDels were found in plasmid. Among these InDels, 4 insertions and 13 deletions exist in ATCC 55025, and 4 insertions and 16 deletions in JB200.

TABLE 10

InDel annotation of ATCC 55025 and JB200 samples

| Sample name | Region | Mutation type | Number |
|---|---|---|---|
| ATCC 55025 chromosome | In CDS | Deletion | 6 |
| | | Insertion | 2 |
| | Intergenic | Deletion | 7 |
| | | Insertion | 2 |
| | Total | — | 17 |
| JB200 chromosome | In CDS | Deletion | 8 |
| | | Insertion | 2 |
| | Intergenic | Deletion | 8 |
| | | Insertion | 2 |
| | Total | — | 20 |

Compared with the parent strain ATCC 55025, the comparative genomic analysis revealed 7 point mutations in the JB200 mutant. Three were adenine-thymine (A-T) base pair deletions, and four were single base pair substitutions, resulting in three single amino acid substitutions in three different proteins and one synonymous mutation in the HD superfamily hydrolase. The three adenine-thymine base pair deletions in JB200 are shown below in Table 11.

TABLE 11

Extra InDels in JB200 mutant

| InDel type | InDel base | Mutation region | Reference protein name | Distance from protein |
|---|---|---|---|---|
| Deletion | A | In CDS | Signal transduction histidine kinase, CA_C3319 | |
| Deletion | A | In CDS | Membrane protein, CA_C0967 | |
| Deletion | A | Intergenic | Cell-wall hydrolase domain-containing protein, CA_C2663 | 373 bp |

Figures 14, 16, 17:
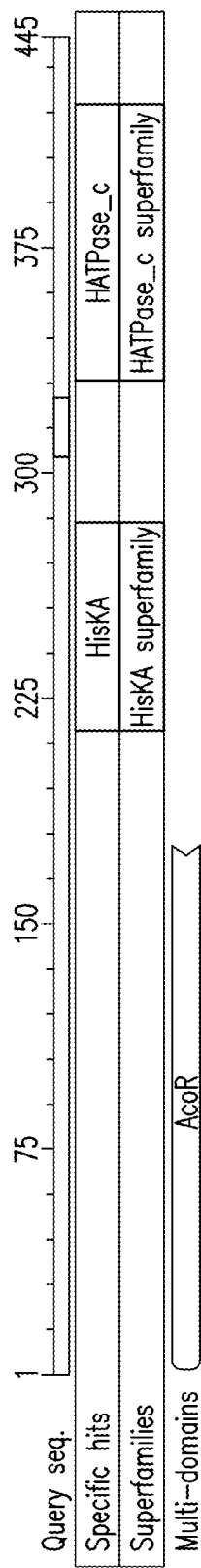
FIG. 14 illustrates the conserved domains of the protein SEQ ID NO: 1 of the JB200 mutant.
FIG. 16 illustrates the conserved domains of the protein SEQ ID NO: 3 of the JB200 mutant.
FIG. 17 shows the alignment of the SEQ ID NO: 5 DNA sequence of JB200 and SEQ ID NO: 14 DNA sequence of parental strain ATCC 55025.

Among the three adenine-thymine base pair deletions, the most dramatic one that occurred is in the gene coding a signal transduction histidine kinase (CA_C3319) (SEQ. ID No. 12), which results in a large portion (70%) of C-terminal truncation of this histidine kinase, as shown in FIG. 13. The protein in JB200 corresponding to CA_C3319 in ATCC 55025 is referred to as mCA_C3319 (SEQ. ID No. 1). The DNA sequence encoding for mCA_C3319 is referred to as mCA_C3319DNA (SEQ. ID No. 2). In FIG. 13 the upper line identifies the protein sequence of the parental strain and the bottom line identifies the protein sequence of JB200. The last 19 amino acids at the C-terminal of the mutant protein mCA_C3319 are different from that in the wild type. Referring to FIG. 14, there are three conserved domains on the signal transduction histidine kinase of JB200 (mCA_C3319), including HATPase_c, HisKA, and AcoR.

The second adenine-thymine base pair deletion results in the C-terminal mutation and extension of a membrane protein with unknown function, CA_C0967 (SEQ. ID No. 13). The protein in JB200 corresponding to CA_C0967 in ATCC 55025 is referred to as mCA_C0967 (SEQ. ID No. 3). The DNA sequence encoding for mCA_C0967 is referred to as mCA_C0967DNA (SEQ. ID No. 4). FIG. 15 shows the alignment of the mCA_C0967 protein sequence of JB200 and the CA_C0967 protein sequence of parental strain ATCC 55025. As shown in FIG. 16, there is only one conserved domain (Branch_AA_trans super family) detected on the mCA_C0967 membrane protein.

The third adenine-thymine base pair deletion occurs at 373 bp away from a cell-wall hydrolase domain-containing protein, CA_C2663, in a RNA coding sequence annotated as tRNA-Xxx, CA_Ct025 (SEQ. ID No. 14). The sequence in JB200 corresponding to CA_Ct025 in ATCC 55025 is referred to as mCA_Ct025 (SEQ. ID No. 5). FIG. 17 shows the alignment of the mCA_Ct025 protein sequence of JB200 and CA_Ct025 protein sequence of parental strain ATCC 55025.

The four single base pair substitutions in the JB200 mutant are shown in Table 12 below.

TABLE 12

Extra SNPs in JB200 mutant

| Reference base | Assembly base | Mutation type | Reference amino acid | Mutation amino acid | Reference protein name |
|---|---|---|---|---|---|
| C | T | Non synonymous | Ala | Val | ATP-dependent zinc metallopeptidase FtsH (cell division protein), CA_C0603 |
| C | T | Non synonymous | Aal | Val | TYPA/BIPA type GTPase, CA_C1684 |
| G | A | Synonymous | Gly | Gly | HD superfamily hydrolase, CA_C0853 |
| C | T | Non synonymous | Ala | Thr | 3-isopropylmalate dehydratase large subunit, CA_C3173 |

Figure 18:
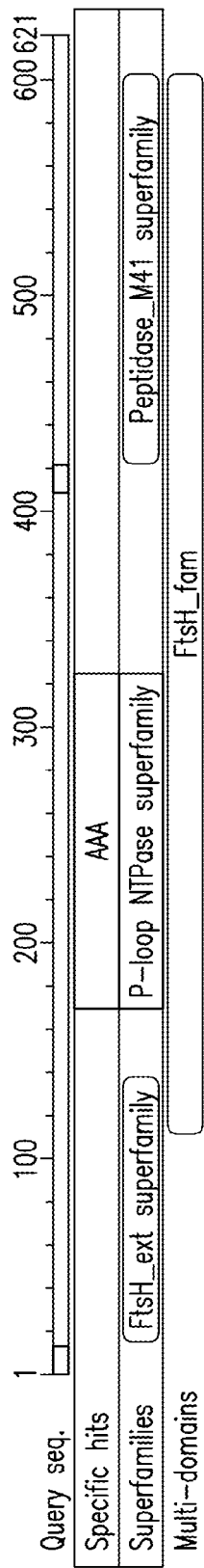
FIG. 18 illustrates the conserved domains of the protein SEQ ID NO 6: of the JB200 mutant.

Among the three proteins with single amino acid substitution, the ATP-dependent zinc metallopeptidase FtsH (cell division protein, CA—C0603) is a membrane-bound ATP-dependent protease universally conserved in prokaryotes. The protein in JB200 corresponding to CA—C0603 is referred to as mCA—C0603 (SEQ. ID No. 6). The DNA sequence encoding for mCA—C0603 is referred to as mCA_C0603DNA (SEQ. ID No. 7). FIG. 18 illustrates the conserved domains of this protein, which is a membrane-bound ATP-dependent protease. In mCA—C0603 of the JB200 mutant, the substitution of alanine by valine occurs at the 308th residue, which locates in the highly conserved domain of the AAA+ (ATPases Associated with a wide variety of cellular Activities) superfamily. The AAA+ represents an ancient group of ATPases belonging to the ASCE (for additional strand, catalytic E) division of the P-loop NTPase fold. The ASCE division also includes ABC, RecA-like, VirD4-like, PilT-like, and SF1/2 helicases. Members of the AAA+ ATPases function as molecular chaperons, ATPase subunits of proteases, helicases, or nucleic-acid stimulated ATPases.

Figure 19:
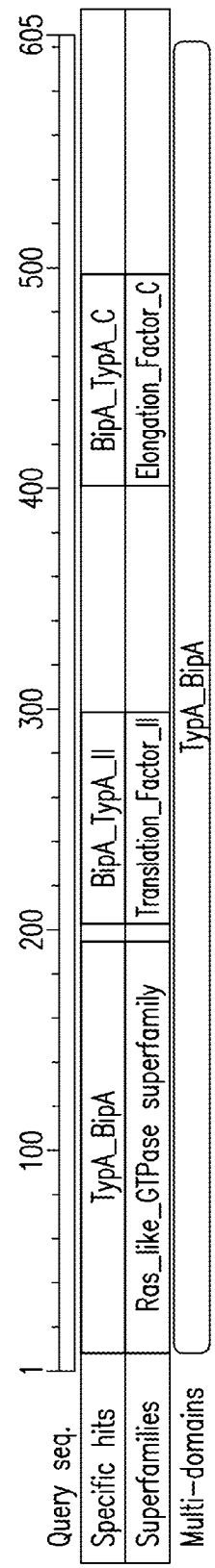
FIG. 19 illustrates the conserved domains of the protein SEQ ID NO: 8 of the JB200 mutant.

Another protein with single amino acid substitution is the TYPA/BIPA type GTPase (CA_C1684). In JB200 the corresponding protein is referred to as mCA_C1684 (SEQ. ID No. 8). The DNA sequence encoding for mCA_C1684 is referred to as mCA_C1684DNA (SEQ. ID No. 9). The protiGTPases are a large family of hydrolase enzymes that can bind and hydrolyze guanosine triphosphate (GTP). In mCA_C1684, a substitution of alanine by valine occurs at the 171st residue, which locates in the highly conserved domain of the TypA (tyrosine phosphorylated protein A)/BipA subfamily, as shown in FIG. 19.

Figure 20:
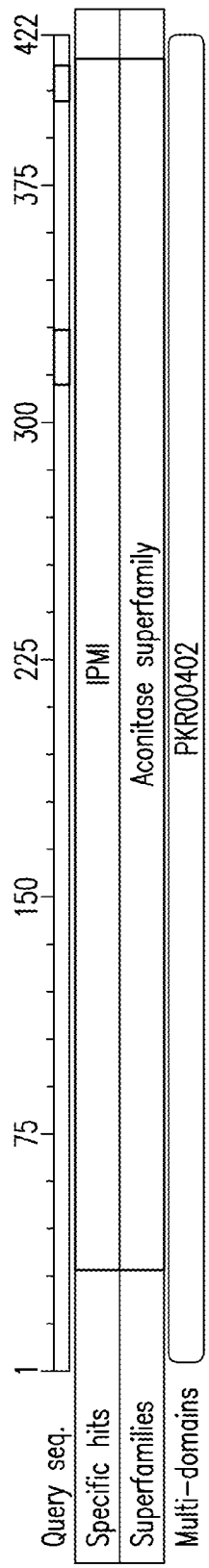
FIG. 20 illustrates the conserved domains of the protein SEQ ID NO: 10 of the JB200 mutant.

The third protein with single amino acid substitution is the 3-isopropylmalate dehydratase large subunit (CA_C3173). In JB200, the corresponding protein is referred to as mCA_C3173 (SEQ. ID No. 10). The DNA sequence encoding for mCA_C3173 is referred to as mCA_C3173DNA (SEQ. ID No. 11). In mCA_C3173, the substitution of alanine by threonine occurs at the 314th residue, which locates in the highly conserved domain of IPMI, as shown in FIG. 20. 3-isopropylmalate dehydratase catalyzes the isomerization between 2-isopropylmalate and 3-isopropyl malate.

Example 2

Figure 21A:
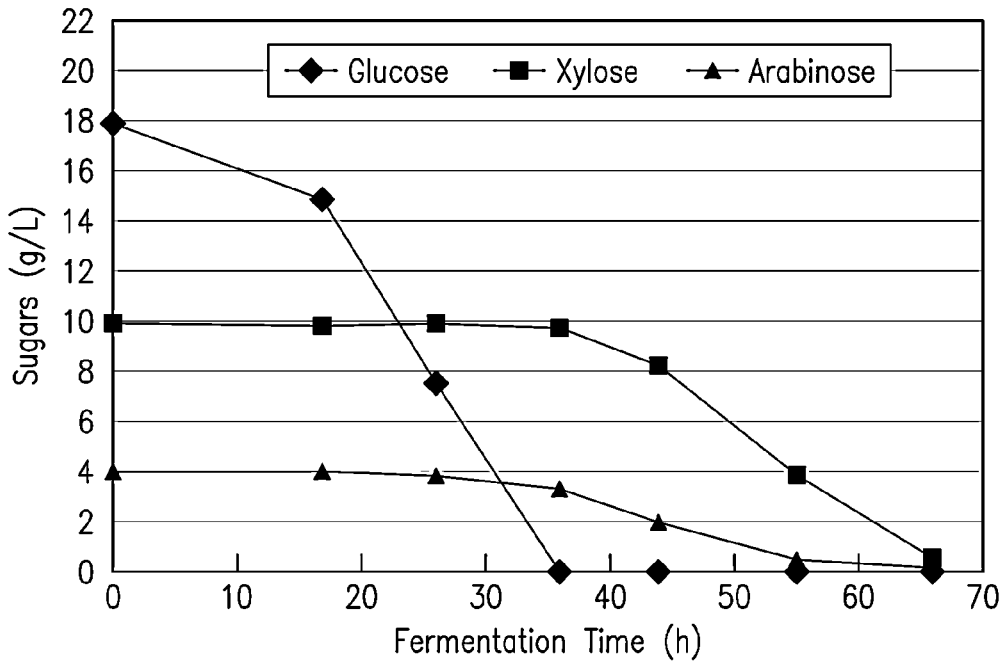
FIGS. 21*a* and *b* display charts of ABE fermentation with corn fiber hydrolysate (CFH) containing glucose, xylose, and arabinose by JB200.
Figure 21B:
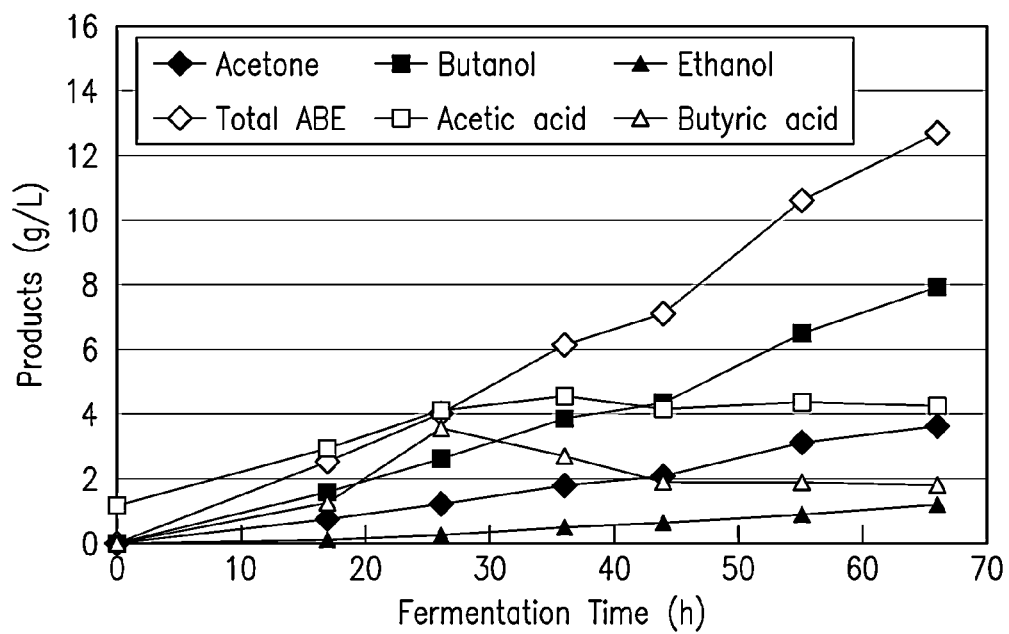

Butanol Production by *Clostridium acetobutylicum* JB200 in Fibrous Bed Bioreactor with Gas Stripping The ABE fermentation capabilities of JB200 were analyzed. First, the fermentation kinetics in glucose, xylose, and glucose/xylose medium were studied to evaluate the hexose and pentose sugar utilization by the mutant cells. Corn fiber hydrolysate (CFH) containing 71.6 g/L total sugar (39.4 g/L glucose, 23.3 g/L xylose and 8.9 g/L arabinose) was obtained after dilute acid and enzyme hydrolysis. CFH severely inhibited acetone-butanol-ethanol (ABE) production (1.9 g/L) by JB200 due to the inhibitors generated during the severe pretreatment process. Boiling and activated carbon were investigated as a detoxification method for CFH in this study. Referring to FIG. 21, ABE fermentation by JB200 with detoxified CFH is shown. Panel A: consumption of sugars during fermentation; Panel B: ABE production during fermentation. Using detoxified CFH, 8.8 g/L ABE was produced with 38.3 g/L reducing sugar left at the end of fermentation. 12.7 g/L ABE was produced when the detoxified CFH was further diluted and all the reducing sugars were depleted within 65 h. These results suggested that boiling and activated carbon was effective in removing inhibitors from CFH, and further diluting the CFH reduced the inhibition to a negligible level. The hydrolysates can be effectively converted to butanol by the JB200 cells immobilized in the FBB.

Figure 22:
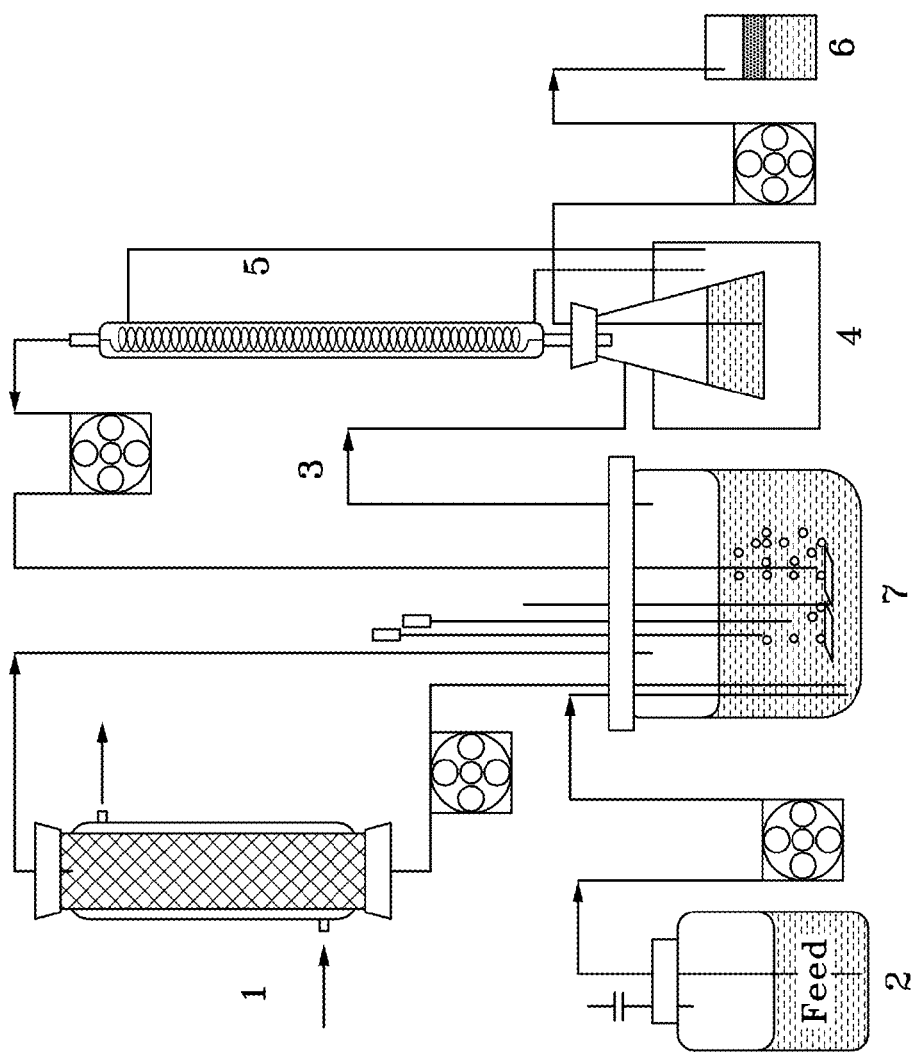
FIG. 22 illustrates an integrated fermentation process with gas stripping for butanol recovery.
Figure 23:
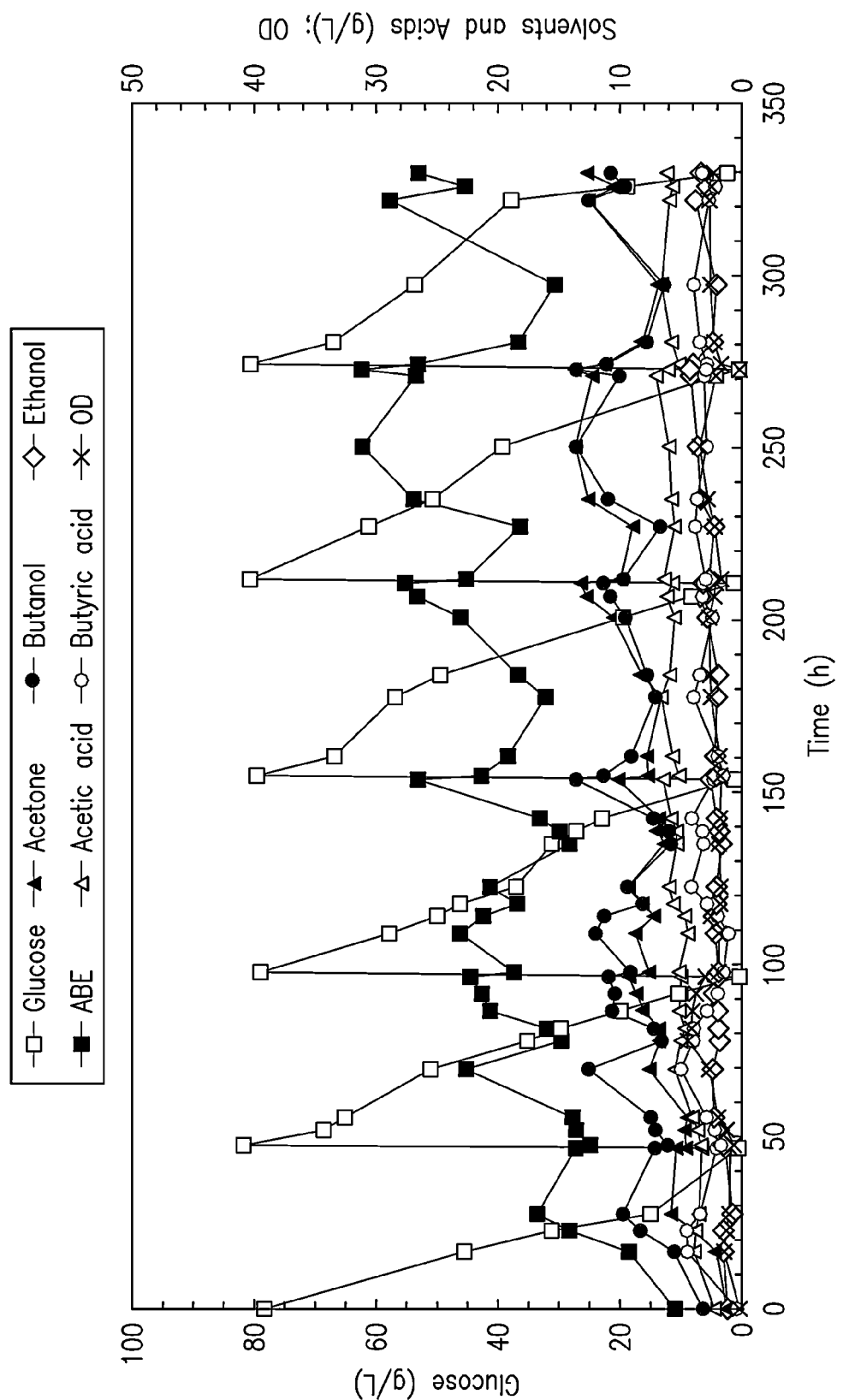
FIG. 23 is a chart displaying fermentation kinetics of the JB200 mutant during repeated batch fermentation with online gas stripping.
Figure 24:
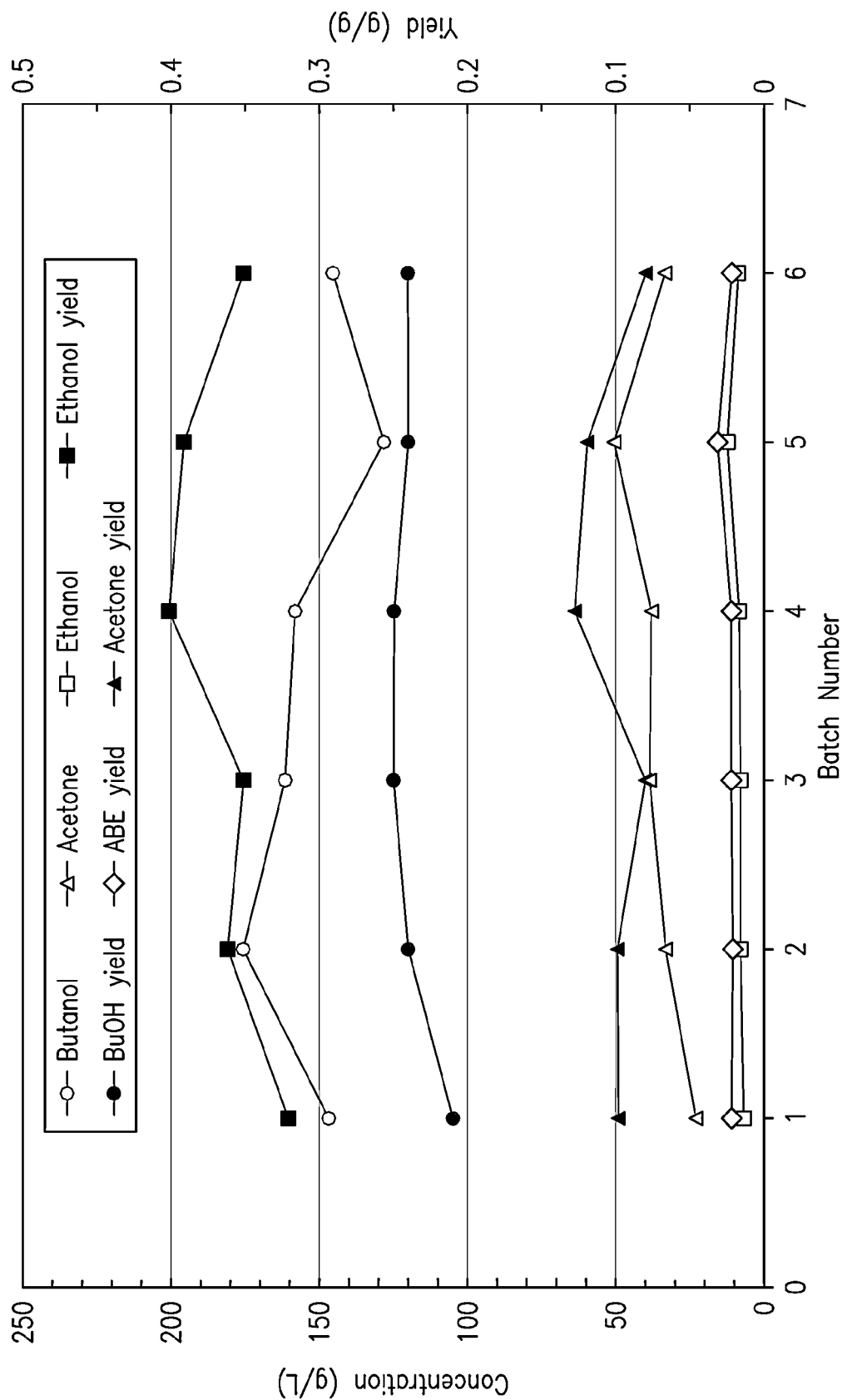
FIG. 24 is a chart displaying fermentation kinetics of the JB200 mutant during repeated batch fermentation with online gas stripping.

Referring to FIG. 22, an integrated fermentation process with gas stripping for continuous butanol recovery in a laboratory set-up is illustrated. The reference numbers in FIG. 22 represent the following: 1: FBB; 2: Feed; 3: $CO_2/H_2$; 4: Cold water; 5: Condenser; 6: Product; 7: stirred tank fermentor. $CO_2/H_2$ was used as the stripping gas. With glucose in the P2 medium and JB200 immobilized in the FBB, the fermentation was operated for 6 consecutive batches in about 350 h. FIGS. 23 and 24 illustrate the kinetics of the repeated batch fermentation. FIG. 23 charts glucose and product concentration profiles in the fermentation broth, and FIG. 24 charts the concentrations of butanol, acetone and ethanol obtained in the condensate and the product yields from the process in each batch. The process was stable with a butanol yield of ~0.25 g/g and total solvents (ABE) yield of ~0.35 g/g. This demonstrates the feasibility of using $CO_2/H_2$ as the stripping gas to continuously recover and concentrate butanol from a less than 1% (w/v) fermentation broth to more than 65% (w/v) butanol solution (after condensation and phase separation) that can be readily purified to more than 99% by simple distillation.

Figure 25:
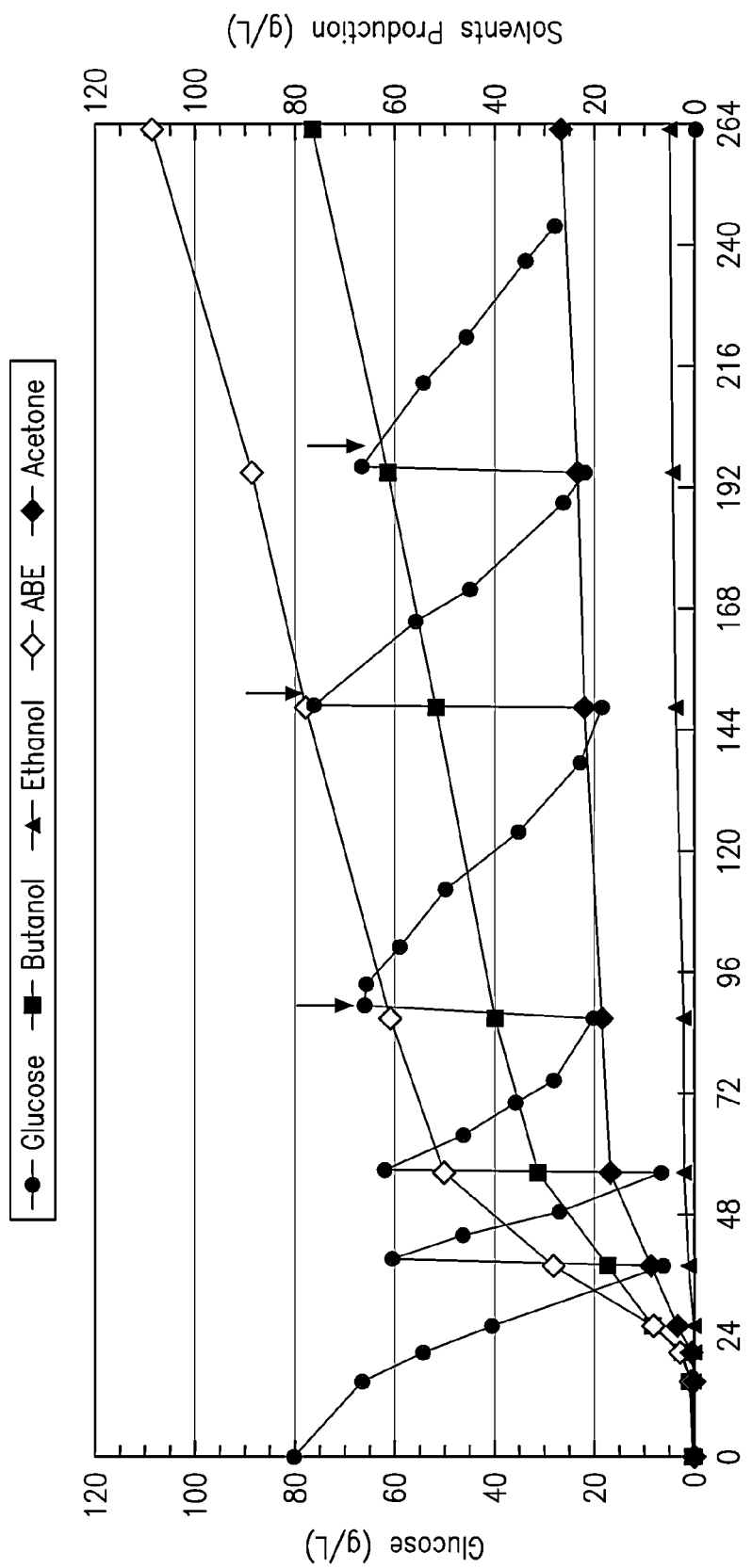
FIG. 25 is a chart displaying fermentation kinetics of fed-batch fermentation of the JB200 mutant with online gas stripping.
Figure 26:
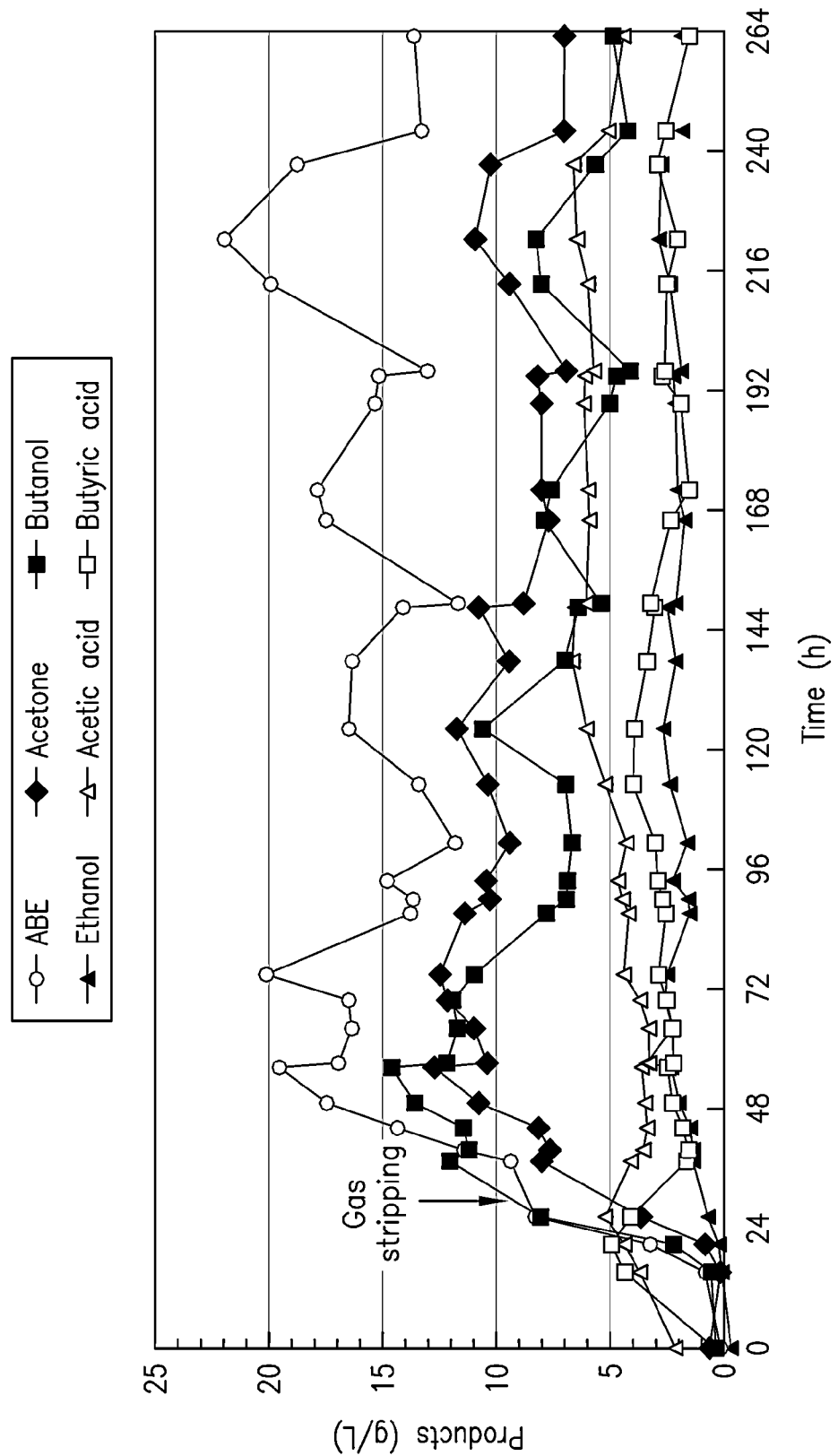
FIG. 26 is a chart displaying fermentation kinetics of fed-batch fermentation of the JB200 mutant with online gas stripping.
Figure 27:
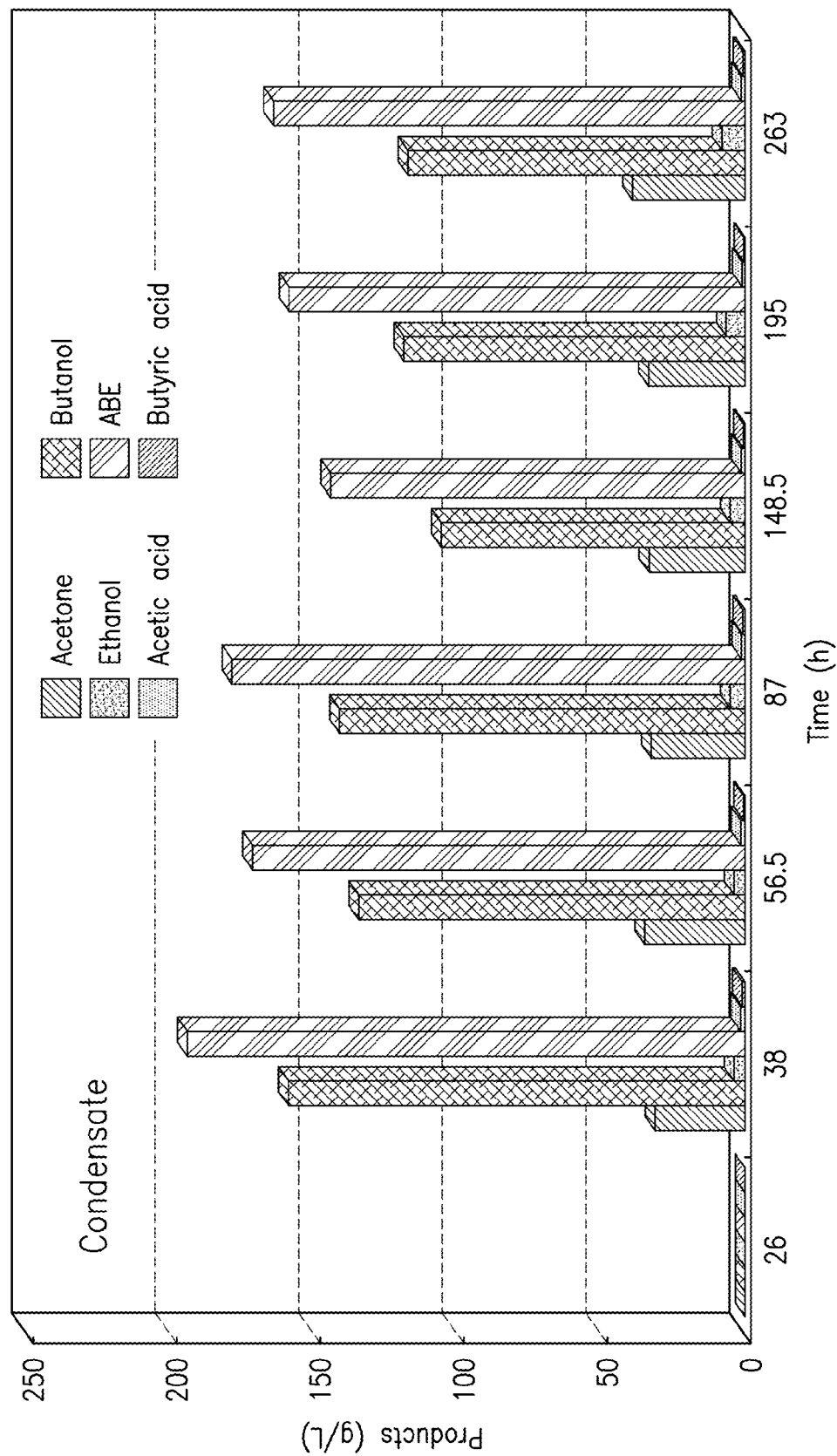
FIG. 27 is a chart displaying fermentation kinetics of fed-batch fermentation of the JB200 mutant with online gas stripping.

The enzymatic hydrolysate of cassava bagasse (CBH) was used as a feedstock for ABE fermentation with JB200 in a fibrous bed bioreactor. About 33.9 g/L ABE were produced from CBH and glucose in batch fermentation. Concentrated CBH containing 584.4 g/L glucose was used in fed-batch fermentation with gas stripping for continuous butanol recovery. FIGS. 25, 26, and 27 illustrated the kinetics of fed-batch fermentation with gas stripping using concentrated CBH as the substrate. FIG. 25 charts glucose concentration and cumulated solvents production profiles, FIG. 26 charts the product concentration profiles in the fermentation broth, and FIG. 27 charts the product concentrations in the condensate collected after each feeding cycle. In this study, continuous gas stripping was turned on at 26 h when the butanol concentration in the fermentation broth had reached ~8 g/L. Condensate of 32 ml, 82 ml, 110 ml, 124 ml, 98 ml, and 131 ml were collected at 38 h, 56.5 h, 87 h, 148.5 h, 195 h and 263 h, respectively. Concentrated CBH was added when the glucose concentration in the fermentation broth was about to deplete or lower than 20 g/L. Additional nutrients (yeast extract) were added for the last three feeding cycles as indicated by the arrows. With periodical nutrient supplementation, stable production of n-butanol from glucose in the CBH was maintained in the fed-batch fermentation over 263 h with an average sugar consumption rate of 1.28 g/L·h and butanol productivity of 0.32±0.03 g/L·h. A total of 108.5 g/L ABE (butanol: 76.4 g/L, acetone: 27.0 g/L, ethanol: 5.1 g/L) was produced, with an overall yield of 0.32±0.03 g/g glucose for ABE and 0.23±0.01 g/g glucose for butanol. The gas stripping process generated a product containing 10% to 16% (w/v) of butanol, ~4% (w/v) of acetone, a small amount of ethanol (<0.8%) and almost no acids, resulting in a highly concentrated butanol solution of ~64% (w/v) after phase separation.

Figure 28:
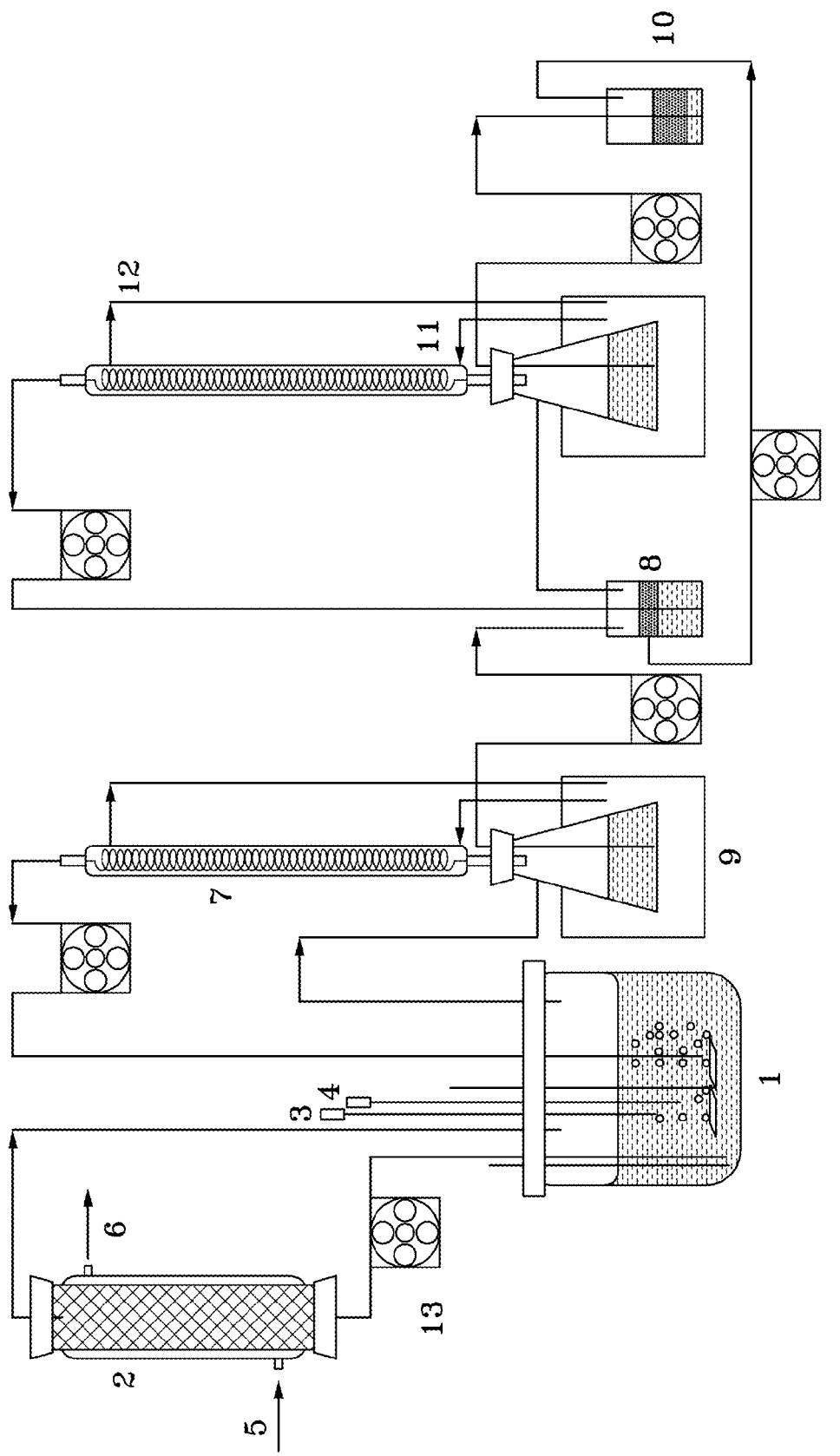
FIG. 28 is a diagram of a two-stage gas stripping recovery process.

Referring to FIG. 28, a two-stage gas stripping recovery process is shown, wherein the components are: 1, stirred tank fermentor; 2, fibrous bed bioreactor; 3, pH controlling unit; 4, temperature controlling unit; 5, thermostat water inlet; 6, thermostat water outlet; 7, condenser; 8, first-stage condensate storage tank; 9, cooling system; 10, second-stage condensate storage tank; 11, thermostat cooling water inlet; 12, thermostat cooling water outlet; and 13, peristaltic pump. A two-stage gas stripping recovery process as shown in FIG. 28 was used for online butanol recovery from ABE fermentation by the JB200 immobilized in the fibrous bed bioreactor operated under repeated batch mode. In the successive batch fermentations with online gas stripping, total glucose utilization was 474.9 g/L and ABE production and productivity were 172.1 g/L and 0.53 g/L·h, respectively. In contrast, conventional batch fermentation without online gas stripping consumed 81.0 g/L glucose with ABE production and productivity of 25.5 g/L and 0.48 g/L·h, respectively. Overall, online gas stripping increased ABE productivity and yield 10.4% and 12.5%, respectively. Butanol, acetone and ethanol concentrations were 150.5, 36.9 and 8.6 g/L, respectively, in the condensate from the first-stage gas stripping and reached 434.2 g/L, 107.9 g/L and 19.2 g/L in the final product from the two-stage gas stripping. Acetic and butyric acids were not found in the condensate from the two-stage gas stripping process. The high butanol concentration obtained in the two-stage gas stripping process makes it highly energy efficient in recovering and purifying butanol from dilute ABE fermentation broth.

Figure 29:
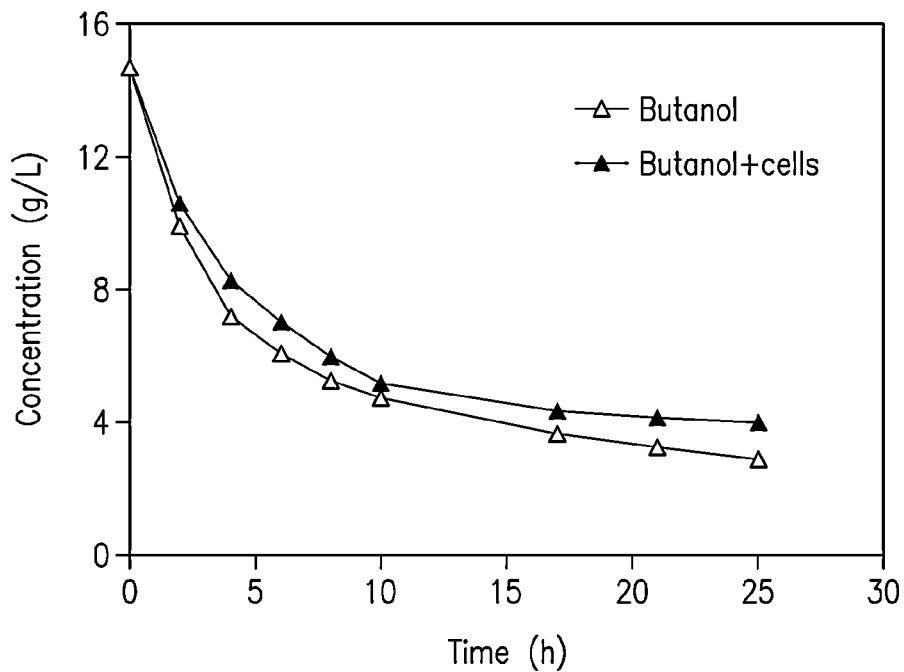
FIG. 29 is a chart displaying kinetics of gas stripping of butanol from dilute fermentation broth of JB200 mutant.
Figure 30:
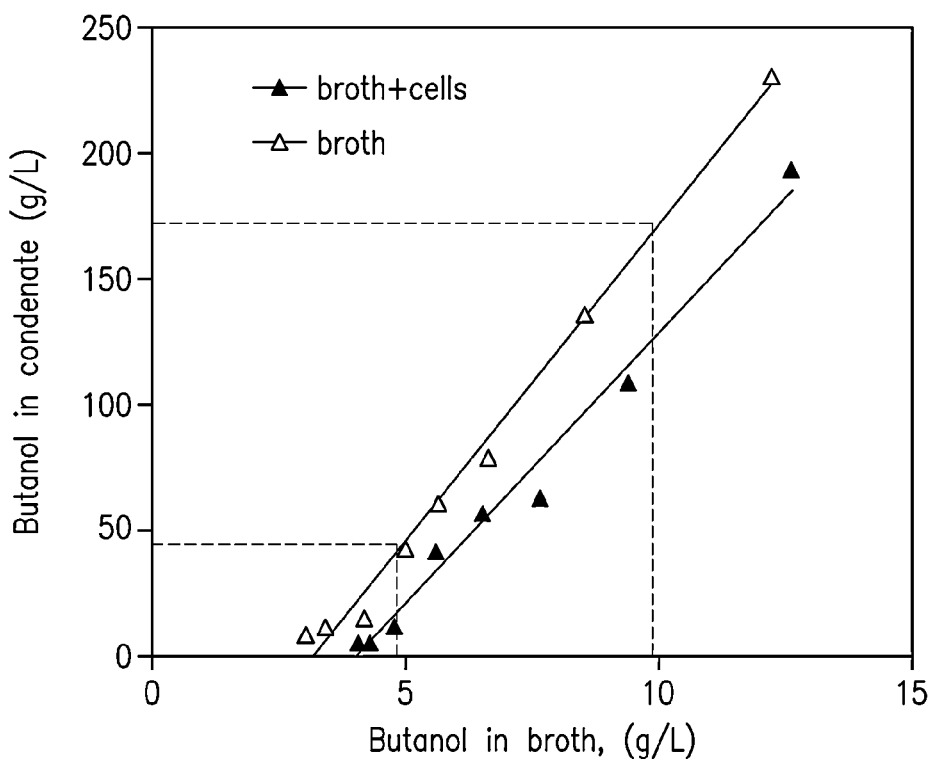
FIG. 30 is a chart displaying kinetics of gas stripping of butanol from dilute fermentation broth of JB200 mutant.

To further evaluate the feasibility and identify kinetic variables of gas stripping for butanol recovery, a gas stripping system consisting of a stirred-tank reactor (fermentor) and a condenser was used. Both ABE fermentation broth with JB200 cells and model solution without cells were used to evaluate possible effects of cells on gas stripping. In both tests the fermentation broth initially contained ~1.3% (w/v) butanol. The concentrations of butanol in the reactor (feed solution) and the condensate were monitored and the results are shown in FIGS. 29 and 30. As can be seen in FIG. 29, the butanol concentration in the feed solution continuously decreased with time, indicating its removal by gas stripping. However, the decrease of butanol concentration in the fermentation broth with cells was slightly slower than that of the model solution without cells. Gas stripping was effective in recovering most of the butanol from the solution when the feed butanol concentration was greater than 4 g/L. The selectivity (butanol over water) was also high, in the range of 10~20. The recovered butanol in the condensate was highly concentrated by a factor of 9 to 17, depending on the feed butanol concentration. As can be seen in FIG. 30, gas stripping can effectively concentrate butanol from a dilute solution of less than 10 g/L to more than 120 g/L in the condensate, which gave a highly concentrated butanol solution of >65% (w/v) after spontaneous phase separation.

Previous studies on ABE fermentation with gas stripping only produced about 25~85 g/L of butanol in the condensate, which is not sufficient to have phase separation and thus requires high energy for further separation and purification. Using JB200 allows for fermentation to operate at a high butanol concentration, achieving over 150 g/L butanol in the condensate, which resulted in an upper phase with over 65% (w/v) solvent (mainly butanol and some acetone and ethanol) that can be purified with a low energy input. Also, although conventional gas stripping does not provide the high efficiency to remove solvents completely from the fermentation broth, this is overcome by recycling the fermentation broth in the repeated batch or fed-batch process as demonstrated above.

Example 3

Figure 31:
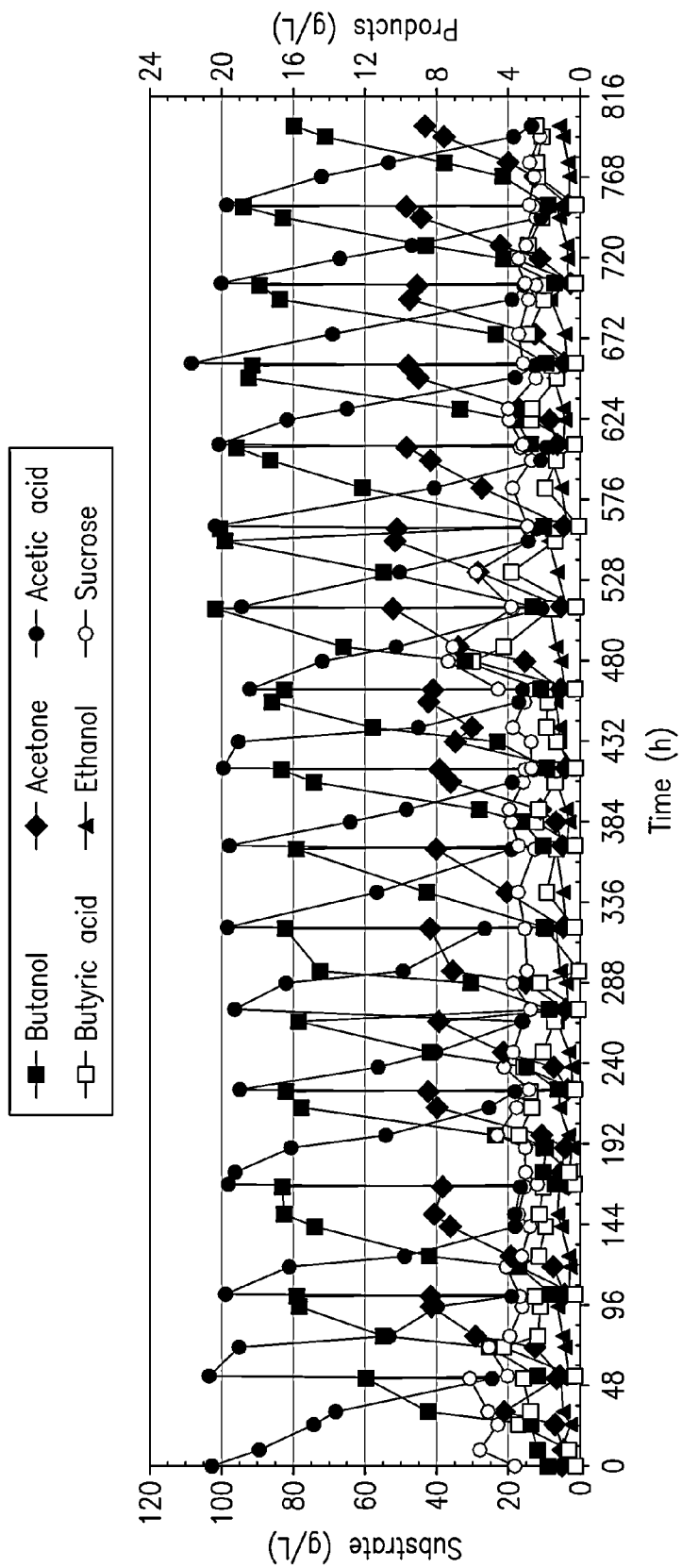
FIG. 31 is a chart of the kinetics of a repeated batch fermentation of the JB200 mutant.
Figure 32:
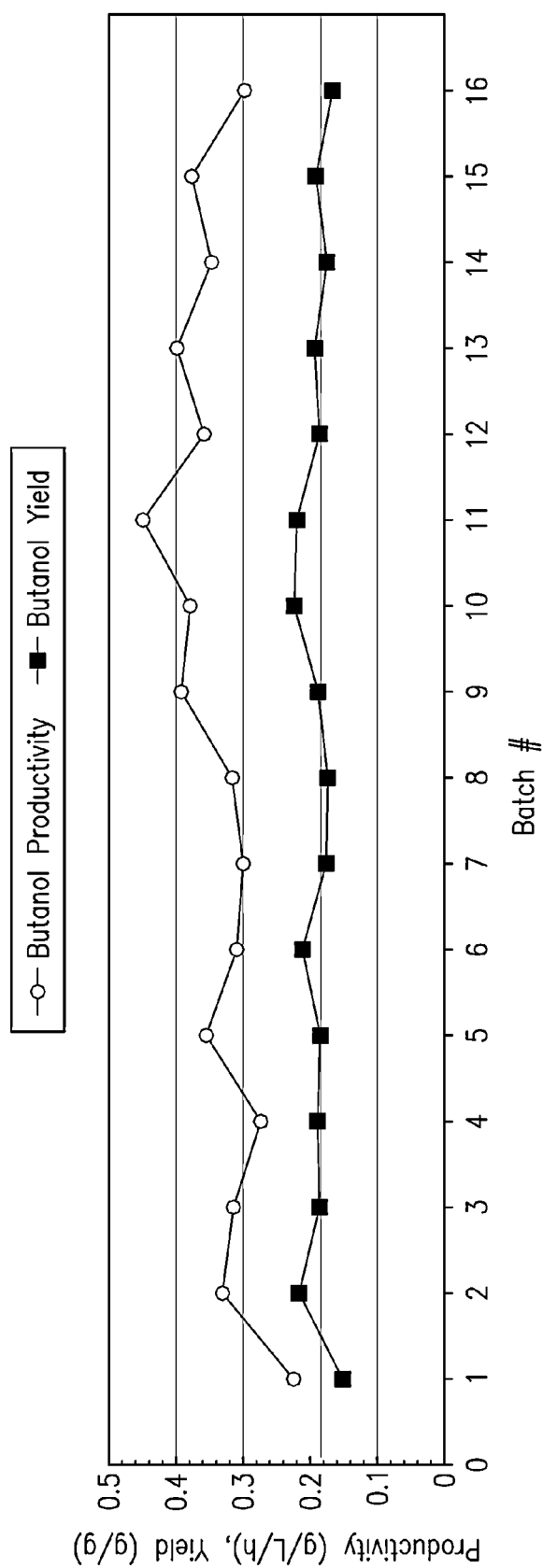
FIG. 32 is a chart of the kinetics of a repeated batch fermentation of the JB200 mutant.

Butanol Production by *Clostridium acetobutylicum* JB200 in Repeated Batch Fermentations To test the long-term stability of JB200 for butanol production, the fermentation was carried out with the FBB operated in a repeated-batch mode for 16 consecutive batches, each for about 2 days, with sucrose as the substrate in P2 medium. In the repeated batch fermentation, the fermentation broth in the reactor system was removed and replaced with a fresh medium about every 2 days, and the cells immobilized in the FBB were used in the consecutive batches without adding new seeding culture. FIG. 31 is a chart of the concentration profiles of substrate (sucrose) and products (butanol, acetone, ethanol, butyric acid, and acetic acid) for the 16 consecutive batches in the repeated batch fermentation over a period of ~33 days. FIG. 32 is a chart of butanol yield and productivity in each of the 16 repeated batches. As can be seen in FIGS. 31 and 32, the fermentation performance was stable and gave consistent butanol production with small fluctuations. The results confirmed that JB200 is genetically stable and can be used in long-term ABE fermentation.

Figure 33:
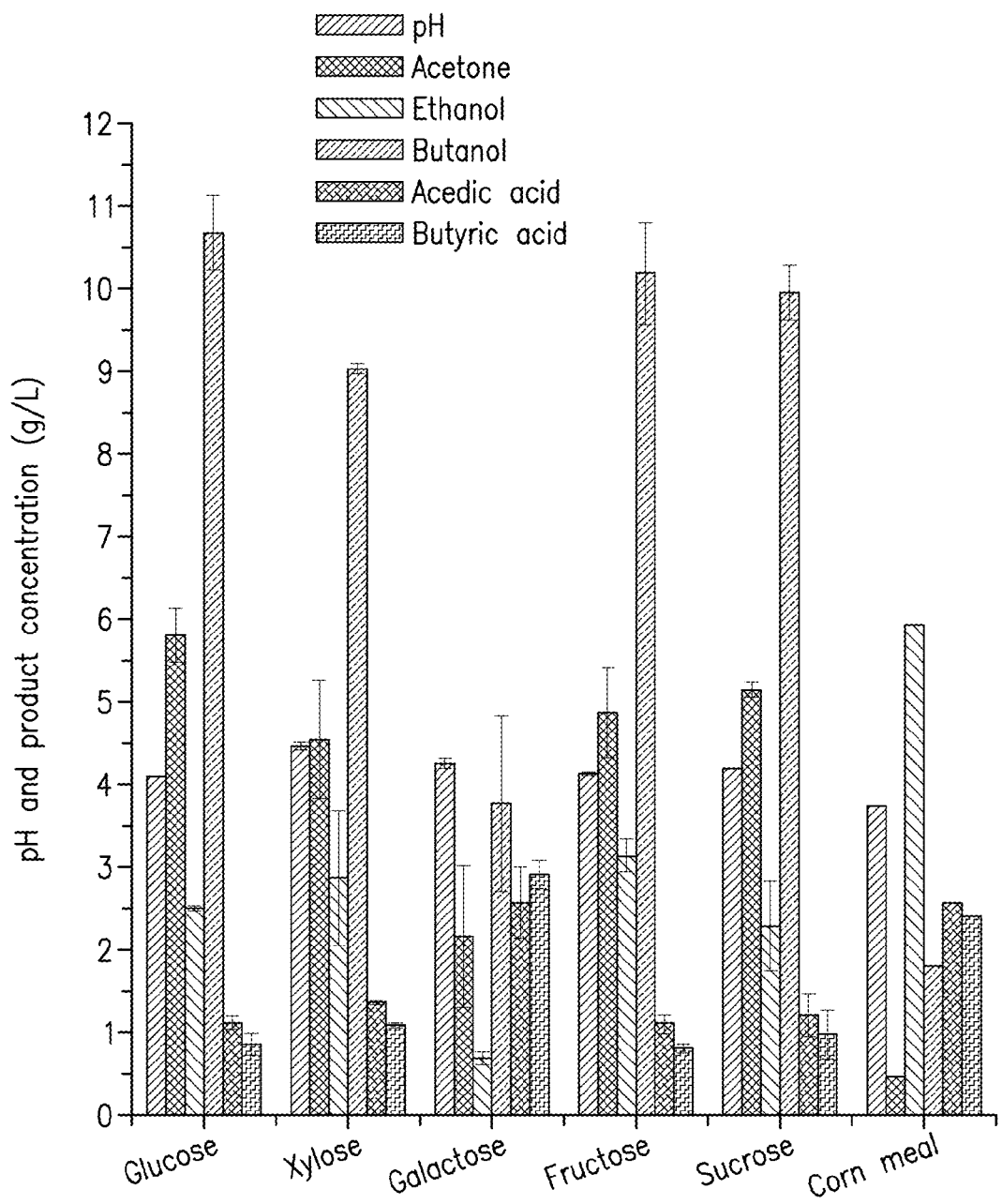
FIG. 33 is a chart of the comparative products of ABE fermentation by JB200 mutants in test tubes using various carbon sources.

It is clear that *C. acetobutylicum* JB200 can produce n-butanol at a high concentration from various carbon sources. Besides glucose, xylose, and sucrose as illustrated in previous examples, JB200 also can use other carbon sources, including fructose, galactose, and starch for butanol production. FIG. 33 illustrates the fermentation results of JB200 grown on various carbon sources in test tubes. In general, glucose, fructose, sucrose and xylose gave comparable butanol production as indicated by the final butanol concentration in the test tubes after about 72 hours incubation. Galactose and corn meal, which contains starch, also can be used by JB200 for n-butanol production. Industrial feedstocks and biomass containing these carbohydrates thus can be used as the substrate for butanol production by JB200.

Other Embodiments

The foregoing description and Examples detail certain specific embodiments of the invention and describe the best mode contemplated by the inventors. It will be appreciated, however, that no matter how detailed the foregoing may appear, the invention can be practiced in many ways and the invention should be construed in accordance with the appended claims and any equivalents thereof. It should be recognized that one of ordinary skill in the art would know how to genetically engineer mutant strains having one or more of the genetic characteristics described in the examples above.

SEQUENCE LISTING

```
<160> NUMBER OF SEQ ID NOS: 14

<210> SEQ ID NO 1
<211> LENGTH: 131
<212> TYPE: PRT
<213> ORGANISM: Clostridium acetobutylicum JB200

<400> SEQUENCE: 1

Met Glu Asn Phe Ser Asp Lys Asp Glu Leu Ile His Lys Trp Asp Ser
1               5                   10                  15

Phe Ile Gly Thr Val Glu Lys Asn Pro Thr Leu Arg Pro Leu Thr Met
            20                  25                  30

Glu Ser Trp Lys Arg Cys Lys Asn Met Gly Val Asn Pro Lys His Ile
        35                  40                  45

Lys Leu Lys Thr Leu Ser His Asn Glu Leu Asn Asp Lys Ile Ser Asn
    50                  55                  60

Asn Leu His Leu Ile Lys Ile Val Lys Pro Tyr Phe Asp Tyr Leu Phe
65                  70                  75                  80

Leu Arg Val Thr Asn Ile Pro Phe Leu Ile Ala Leu Ala Asp Ser Lys
                85                  90                  95

Ala Trp Ile Ile Asn Ile Ser Gly Asn Val Asn Asp Phe Gly Glu Lys
            100                 105                 110

Asn Leu Asp Phe Ala Leu Val Leu Ile Val Leu Lys Asn Ile Leu Val
        115                 120                 125

Ile Met Glu
    130

<210> SEQ ID NO 2
<211> LENGTH: 396
<212> TYPE: DNA
<213> ORGANISM: Clostridium acetobutylicum JB200

<400> SEQUENCE: 2
gtggaaaact tttcagataa agatgaatta atacacaaat gggatagctt tattggtact      60
gtagaaaaaa atcctacact cagaccatta actatggaat catggaaaag gtgcaaaaat     120
atgggcgtca atcctaaaca tattaaatta aaaactcttt ctcataatga gctaaatgat     180
aaaatttcaa acaatcttca tttaataaaa attgtaaaac cttatttttga ttatttattc    240 ttacgtgtta ctaacatacc attttttaatt gccttagcag atagcaaagc ttggattatt   300
aacatcagcg gtaatgtaaa tgatttcgga gaaaaaaatt tagatttttgc cttggttcta    360 attgttctga aaatatatt ggtaataatg gaatag                                396

<210> SEQ ID NO 3
<211> LENGTH: 581
<212> TYPE: PRT
<213> ORGANISM: Clostridium acetobutylicum JB200

<400> SEQUENCE: 3
```

```
Met Asn Thr Lys Met His Asn Lys Lys Arg Ile Phe Ser Ile Tyr
1               5                   10                  15

Ile Leu Leu Ile Leu Leu Ile Arg Leu Phe Leu Ser Thr Gly Val Arg
            20                  25                  30

Ile Trp Ala Phe Gly Asn Asn Gln Tyr Asp Asp Gly Met Met Ile Lys
            35                  40                  45

Asn Ala Thr Asn Leu Ile Ala Gly Asn Trp Leu Gly Ser Tyr Asp Gln
50                  55                  60

Tyr Ile Phe Ala Lys Gly Val Thr Phe Pro Ile Tyr Leu Glu Leu Leu
65                  70                  75                  80

His Lys Ile Gly Ile Pro Phe Ile Ile Ser Asn Val Leu Met Cys Phe
                85                  90                  95

Ala Ala Ser Leu Thr Phe Ile Ile Val Ile Lys Val Ile Pro Asn
            100                 105                 110

Leu Asn Ala Leu Ala Ile Ile Tyr Thr Ile Leu Met Phe Asn Pro Ile
            115                 120                 125

Ala Thr Ala Ser Trp Thr Phe Gln Arg Val Tyr Arg Asp Ser Leu Tyr
130                 135                 140

Ser Tyr Leu Ile Val Ile Leu Phe Ser Leu Ile Ile Gly Ile Tyr Leu
145                 150                 155                 160

Asn Arg Lys Glu Ser Phe Asn Lys Leu Leu Ser Tyr Ser Ile Val Ala
            165                 170                 175

Gly Phe Phe Leu Ser Ser Val Trp Leu Ala Arg Glu Asp Ser Pro Trp
            180                 185                 190

Val Leu Pro Phe Val Gly Met Ala Leu Ile Val Thr Leu Val Leu Ile
            195                 200                 205

Phe Leu Asp Lys Asn Ser Glu Met Lys Val Arg Met Lys Lys Ala Leu
            210                 215                 220

Ala Leu Thr Val Ile Pro Ile Phe Leu Ile Val Ser Ile Leu Val Val
225                 230                 235                 240

Ser Thr Ile Asn Tyr Thr Arg Tyr Gly Val Ala Ile Thr Asn Glu Tyr
                245                 250                 255

Thr Gly Gly Tyr Leu Pro Arg Leu Phe Lys Asp Leu Thr Ile Ile Gln
            260                 265                 270

Pro Asp Glu Trp Met Ala Gln Val Pro Ile Pro Lys Ser Thr Arg Glu
            275                 280                 285

Lys Ala Tyr Lys Val Ser Pro Thr Phe Ser Lys Leu Lys Asn Thr Leu
            290                 295                 300

Glu Asn His Ala Phe Val Ala Thr Thr Pro Gly Gly Asn Ala Ser Cys
305                 310                 315                 320

Ser Met Leu Ala Trp Ala Val Ile Asp Ser Val Gln Trp Tyr Gly Ile
            325                 330                 335

Lys Asp Ala Lys Ser Ser Gln Glu Phe Tyr Lys Lys Ser Ser Glu Glu
            340                 345                 350

Ile Glu Ala Ala Ile Lys Ser Gly Lys Leu Lys Thr Arg Gly Gly Tyr
            355                 360                 365

Ile Phe Met Phe Glu Ser Pro Trp Asp Asn Arg Tyr Val Lys Pro Leu
            370                 375                 380

Leu Lys Ser Phe Ile Gln Thr Ile Lys Thr Thr Val His Met Gly Gln
385                 390                 395                 400

Tyr Tyr Asn Met Glu Glu Glu Ser Leu Val Lys Thr Leu Gln Leu Ser
                405                 410                 415

Arg Lys Tyr Asn Asn Thr Ile Val Pro Leu Phe Glu Lys Asn Ile Ala
```

```
                  420                 425                 430
Ser Ile Gly Thr Lys Glu Gln Val Arg Lys Leu Glu Tyr Ile Thr Asn
            435                 440                 445

Asn Ile Ala Tyr Asn Lys Glu Asp Val Ile Pro Lys Arg Gln Thr Lys
        450                 455                 460

Val Ala Ile Ser Asn Lys Ile Ser Leu Ile Tyr Tyr Glu Leu Asn Pro
465                 470                 475                 480

Tyr Leu Phe Leu Ile Gly Leu Ile Gly Tyr Val Tyr Ile Thr Leu Arg
                485                 490                 495

Phe Leu Leu Ser Ile Arg Lys Lys Lys Tyr Phe Leu Ala Asp Glu Trp
            500                 505                 510

Leu Ile Thr Thr Gly Ile Phe Leu Ser Tyr Leu Leu Arg Leu Leu Leu
        515                 520                 525

Ile Ser Tyr Thr Asp Val Cys Ser Ile Phe Met Gln Tyr Ser Met Tyr
    530                 535                 540

Leu Ala Pro Ser Tyr Trp Leu Ile Leu Met Phe Thr Phe Thr Ser Ile
545                 550                 555                 560

Phe Ile Ser Met Arg Asp Phe Val Lys Asn Tyr Tyr Asn Lys Lys
                565                 570                 575

Ala Ser His Lys Asn
            580

<210> SEQ ID NO 4
<211> LENGTH: 1746
<212> TYPE: DNA
<213> ORGANISM: Clostridium acetobutylicum JB200

<400> SEQUENCE: 4
atgaatacaa aaatgcataa taagaaaaaa aggattttct ctatatatat tctactgatt       60
ttattaataa ggttattctt atcaacaggg gtaagaattt gggcatttgg aaataatcaa      120
tatgatgatg aatgatgat aaaaaatgct actaatctaa ttgcaggaaa ttggcttgga      180
agttatgatc aatacatatt tgcaaaaggt gtaacattcc ctatttattt agaattatta      240
cataagatag gtattccatt tattatttca atgttttaa tgtgtttcgc ggcttcgtta      300
acatttataa ttgttataaa aaaggtaata ccaaatttaa atgcgcttgc tataatttat      360
actattttaa tgttcaatcc gatagctact gcttcttgga cttttcaaag ggtatacaga      420
gattctttat acagttattt aattgtaatt ttatttttctt tgattatagg aatatatttg      480
aataggaaag agtcttttaa taagttatta agctacagta tagttgcagg attttttctta      540 tcatccgttt ggcttgcgag agaggattcg ccatgggtct taccgtttgt tggtatggca      600
ttaattgtaa cactagtact tatatttttg gataaaaatt cagaaatgaa ggttagaatg      660
aaaaaagctt tggcgttaac agtcattcct atttttctta gtaagtat attagtagtt      720 tccacaataa attatacacg ttatggtgta gctataacta atgagtatac aggggggctat      780 ttgcctaggc tatttaaaga tttaactata atacaaccag atgaatggat ggctcaggtt      840
cctataccaa agtcaacgag agaaaaagct tataagtat cgcctacttt ttccaagcta      900
aaaaatacat tagaaaatca tgcatttgta gctactacac caggaggaaa tgcatcttgc      960
tcaatgttgg cttgggctgt cattgacagt gttcagtggt acggaattaa agatgcaaaa     1020
tcaagccaag agttttacaa gaaatcttca gaagaaatag aagctgcaat aaagtcggga     1080
aaattaaaaa caaggggcgg atatattttt atgtttgaat ctcctttggga ataatagatat     1140 gttaagccgc tgcttaaatc atttattcag accattaaaa ctactgttca tatgggacaa     1200
```

```
tattataata tggaggaaga aagtcttgtt aagacacttc aattaagtag gaaatataac    1260
aatacaattg tacctttgtt tgaaaaaaac atagcgagta ttggaacaaa agaacaagta    1320
agaaagttag aatatataac aaataatatt gcttataata agaggatgt tatacctaaa     1380 agacaaacaa aggtagctat aagcaataaa attagtttaa tttattatga attgaatccg    1440
tatttgtttt taattggtct aataggttat gtgtatatta cactgcgctt tttactaagt    1500
ataagaaaga aaaatactt tttagctgat gagtggctaa ttacaactgg gatattttta    1560
agctatttgc ttcgattgct cttaatatct tatactgatg tttgttctat atttatgcag    1620
tactccatgt acttagctcc tagttattgg ttgatactta tgtttacttt tactagtata    1680
tttatttcca tgagagattt tgttaagaac tactattata ataaaaagc aagccataaa     1740 aattaa                                                                1746

<210> SEQ ID NO 5
<211> LENGTH: 71
<212> TYPE: DNA
<213> ORGANISM: Clostridium acetobutylicum JB200

<400> SEQUENCE: 5
agcgggtaga gggaatcgaa ccctcgtaac tagcttggaa ggctagcact ctaccattga    60
gttacacccg c                                                          71

<210> SEQ ID NO 6
<211> LENGTH: 621
<212> TYPE: PRT
<213> ORGANISM: Clostridium acetobutylicum JB200

<400> SEQUENCE: 6

Met Phe Asp Asn Lys Asp Phe Lys Asp Asn Lys Tyr Lys Tyr Ala Ile
1               5                   10                  15

Phe Tyr Thr Leu Gly Ala Ile Ile Phe Val Leu Leu Val Asn Tyr Ala
                20                  25                  30

Ala Ser Ser Ile Arg Thr Glu Glu Ile Thr Tyr Asn Lys Phe Leu Asp
            35                  40                  45

Leu Leu Asn Ala Lys Lys Val Ser Gln Val Asn Ile Ser Asp Glu Lys
        50                  55                  60

Ile Met Ile Val Pro Lys Glu Asn Ala Gly Phe His Lys Lys Ile Leu
65                  70                  75                  80

Tyr Thr Gly Arg Ile Glu Asp Pro Asp Leu Lys Thr Glu Leu Lys Lys
                85                  90                  95

Ser Gly Ala Glu Ile Lys Pro Glu Ile Lys Asn Asp Asp Pro Ile Lys
                100                 105                 110

Asn Phe Leu Ile Thr Trp Ile Leu Pro Ile Ile Leu Leu Ala Phe Phe
            115                 120                 125

Gly Lys Ile Leu Phe Gly Lys Leu Asp Lys Lys Phe Gly Asn Gly Val
        130                 135                 140

Met Ser Phe Gly Lys Asn Asn Ala Lys Leu Tyr Ala Glu Ser Glu Thr
145                 150                 155                 160

Gly Lys Thr Phe Glu Asp Val Ala Gly Gln Glu Ala Lys Glu Ser
                165                 170                 175

Leu Val Glu Ile Val Asp Phe Leu His Asn Pro Asn Tyr Ala Glu
                180                 185                 190

Ile Gly Ala Lys Leu Pro Lys Gly Ala Leu Leu Val Gly Pro Pro Gly
            195                 200                 205

Thr Gly Lys Thr Leu Leu Ala Lys Ala Val Ala Gly Glu Ala Lys Val
```

```
            210                 215                 220
Pro Phe Ser Met Ser Gly Ser Asp Phe Val Glu Met Phe Val Gly
225                 230                 235                 240

Met Gly Ala Ala Arg Val Arg Asp Leu Phe Glu Gln Ala Gln Glu Lys
            245                 250                 255

Ala Pro Cys Ile Ile Phe Ile Asp Glu Ile Asp Ala Ile Gly Lys Ser
            260                 265                 270

Arg Glu Asn Thr Leu Gly Gly Ser Asn Asp Glu Arg Glu Gln Thr Leu
            275                 280                 285

Asn Gln Leu Leu Ala Glu Met Asp Gly Phe Asp Ser Ser Lys Gly Val
            290                 295                 300

Val Ile Leu Val Ala Thr Asn Arg Pro Glu Ile Leu Asp Lys Ala Leu
305                 310                 315                 320

Leu Arg Pro Gly Arg Phe Asp Arg Arg Val Ile Val Asp Arg Pro Asp
            325                 330                 335

Leu Lys Gly Arg Glu Ala Ile Leu Lys Val His Ala Lys Asp Val Lys
            340                 345                 350

Met Ser Glu Asp Ile Ser Leu Glu Glu Ile Ala Lys Ala Thr Ser Gly
            355                 360                 365

Ala Val Gly Ala Asp Leu Ala Asn Ile Val Asn Glu Ala Ala Leu Leu
            370                 375                 380

Ala Val Lys Asn Gly Arg Asn Lys Val Tyr Gln Glu Asp Leu Asp Lys
385                 390                 395                 400

Ala Val Glu Phe Ile Ile Ala Gly Lys Glu Lys Asp Lys Ile Leu
            405                 410                 415

Ser Asp Lys Asp Lys Lys Thr Val Ala Tyr His Glu Val Gly His Ala
            420                 425                 430

Leu Val Ala Ala Leu Leu Lys His Thr Asn Pro Val His Lys Ile Thr
            435                 440                 445

Ile Val Pro Thr Thr Met Gly Ala Leu Gly Tyr Thr Met Gln Leu Pro
            450                 455                 460

Glu Glu Glu Lys Tyr Leu Val Thr Lys Asp Glu Met Met Asp Glu Ile
465                 470                 475                 480

Ser Val Leu Leu Gly Gly Arg Ser Ser Glu Glu Val Val Phe Gly Thr
            485                 490                 495

Ile Ser Thr Gly Ala Ser Asn Asp Ile Glu Lys Ala Thr Gln Thr Ala
            500                 505                 510

Arg Asn Met Val Thr Ile Tyr Gly Met Thr Asp Lys Phe Asp Met Met
            515                 520                 525

Ala Leu Gln Ser Gln Gly Ser Arg Tyr Leu Asp Gly Thr Pro Ala Lys
            530                 535                 540

Asn Cys Ser Asn Glu Val Glu Tyr Glu Ala Asp Lys Glu Val Leu Arg
545                 550                 555                 560

Ile Ile Lys Glu Ala His Asn Lys Ala Lys Asp Ile Leu Lys Ala Asn
            565                 570                 575

Arg Glu Leu Leu Asp Ser Ile Ala Glu Ile Leu Leu Val Lys Glu Thr
            580                 585                 590

Leu Thr Gly Ser Glu Phe Met Lys Ile Val Lys Glu Ser Ser Ala Trp
            595                 600                 605

Lys Glu Met Asn Glu Ile Gln Met Glu Lys Leu Thr Asp
            610                 615                 620

<210> SEQ ID NO 7
<211> LENGTH: 1866
```

```
<212> TYPE: DNA
<213> ORGANISM: Clostridium acetobutylicum JB200

<400> SEQUENCE: 7
atgtttgata taaagatttt caaagataac aagtataagt atgctatttt ttatacacta      60
ggggcaataa ttttgtcct attggttaat tatgcagcat cctcaataag aactgaagaa     120
ataacatata ataaatttct cgatttatta aatgcaaaaa aagtttcaca ggttaatatt     180
tcagatgaaa agataatgat agtgccaaaa gagaatgctg gctttcataa aaagattcta     240
tatacaggta gaatagaaga tccggattta aaaactgagc ttaagaaatc aggagcagaa     300
ataaagccag agataaaaaa tgatgatcca ataagaatt ttttaatcac atggattttg      360
ccgataatac ttcttgcttt ctttggtaag attttatttg gaaaactgga taaaaagttt     420
ggtaatggag ttatgtcttt tggtaagaat aatgctaaat tatatgcaga aagtgaaaca     480
ggaaaaaccct tgaagatgt tgctggacag gaagaagcaa aagagtctct tgtggaaatt     540
gtagattttc tacataatcc taataaatat gcagaaatag gagctaaact tcctaaggga     600
gcacttttag ttggtccgcc aggtacagga aaaactcttt tagcaaaggc tgtagctgga     660
gaggccaaag taccattttt ttcaatgtca ggttctgatt tgttgaaat gtttgttgga     720
atgggagctg caagggttag agatttattt gagcaagctc aagaaaaggc accttgtata     780
atatttatag atgaaataga cgccataggt aagagtagaa aaatacact tggaggctct      840
aatgatgaga gagagcaaac tttaaatcag ctttttagcag aaatggatgg ttttgattcg     900
tcaaagggag ttgttatttt agttgcaact aatagaccag atttttaga taaggcactt      960
ttaaggcctg aagatttga tagaagagtt atagtagata gacctgattt aaaaggtagg    1020
gaggctatac ttaaagttca tgctaaagat gttaagatgt cagaggatat atctcttgaa    1080
gaaatagcaa aagcaaccctc aggtgctgtt ggagctgatc ttgcaaatat agtaaatgaa    1140
gctgcacttt tagctgtaaa gaatggaagg aataaggttt atcaggaaga tctagataag    1200
gcagttgaat ttataattgc aggaaaagaa aagaaagata agatattgtc agataaagac    1260
aagaagacag ttgcatatca tgaagttggt catgcgttag tagcggctct tttaaaacat    1320
actaatccgg tacataaaat aactattgtg cctacaacta tgggagcatt gggatatact    1380
atgcagcttc cagaagaaga aaaatatctt gtaactaaag atgaaatgat ggatgagata    1440
tctgttctac ttggaggaag gtcctcagag gaagttgttt ttggaactat ttcaacggga    1500
gcatcaaatg atatagaaaa agccacacaa actgctagaa atatggttac aatatatgga    1560
atgactgata agtttgatat gatggcactt cagtctcaag gaagtagata tttagatgga    1620
actcctgcta aaaattgtag caatgaagtt gagtatgaag cagataaaga ggtattaaga    1680
attataaaag aagcacataa taaagcaaag gatatttttaa aggcgaatag agagcttctt    1740
gatagtattg cagaaattct tcttgtgaaa gaaacattaa ctggcagcga atttatgaaa    1800
attgtaaagg agagctcagc atggaaagag atgaacgaaa tacagatgga gaagttaaca    1860
gattaa                                                              1866

<210> SEQ ID NO 8
<211> LENGTH: 605
<212> TYPE: PRT
<213> ORGANISM: Clostridium acetobutylicum JB200

<400> SEQUENCE: 8

Met Glu Lys Ile Thr Arg Asn Asp Ile Arg Asn Ile Ala Ile Ile Ala
1               5                   10                  15
```

```
His Val Asp His Gly Lys Thr Thr Leu Val Asp Ala Leu Leu Arg Gln
         20                  25                  30

Ser His Val Phe Arg Ala Asn Glu Lys Val Glu Arg Val Met Asp
         35                  40                  45

Ser Asn Asp Leu Glu Lys Glu Arg Gly Ile Thr Ile Leu Ser Lys Asn
 50                  55                  60

Thr Ser Leu Met His Asp Gly Ile Lys Ile Asn Ile Val Asp Thr Pro
 65                  70                  75                  80

Gly His Ala Asp Phe Gly Gly Val Glu Arg Val Leu Lys Met Val
                 85                  90                  95

Asp Ser Val Leu Leu Val Asp Ala Phe Glu Gly Pro Met Pro Gln
         100                 105                 110

Thr Lys Phe Val Leu Lys Lys Ala Leu Glu Leu Lys Leu Lys Pro Ile
         115                 120                 125

Val Val Ile Asn Lys Ile Asp Lys Pro Asn Ala Arg Pro Met Glu Val
 130                 135                 140

Val Asp Glu Val Leu Asp Leu Phe Ile Asp Leu Gly Ala Asp Glu Asp
 145                 150                 155                 160

Gln Leu Asp Phe Pro Ile Val Tyr Ala Ser Val Lys Ala Gly Ile Ala
                 165                 170                 175

Lys Leu Asp Val Asp Asp Glu Ser Glu Thr Met Glu Pro Leu Phe Glu
         180                 185                 190

Thr Ile Val Lys Tyr Val Lys Gly Pro Glu Gly Tyr Leu Asp Glu Pro
         195                 200                 205

Leu Gln Met Leu Val Ser Thr Ile Asp Ser Asn Glu Tyr Val Gly Arg
         210                 215                 220

Ile Ala Ile Gly Arg Val Glu Arg Gly Ser Ile Lys Lys Asn Gln Gln
225                 230                 235                 240

Ala Val Leu Ile Arg Arg Asp Gly Ala Lys Glu Asn Val Lys Ile Ser
                 245                 250                 255

Ser Leu Phe Thr Tyr Glu Gly Leu Lys Arg Val Glu Ala Asp Glu Val
         260                 265                 270

Lys Phe Gly Asp Ile Ala Val Val Ser Gly Ile Pro Asp Val Asn Ile
         275                 280                 285

Gly Glu Thr Ile Ala Asp Ala Ser Arg Pro Glu Ala Leu Pro Phe Val
 290                 295                 300

Asp Ile Asp Glu Pro Thr Leu Ser Met Phe Phe Met Val Asn Asp Ser
305                 310                 315                 320

Pro Phe Ala Gly Arg Glu Gly Asp Phe Val Thr Ser Arg His Leu Arg
                 325                 330                 335

Asp Arg Leu Glu Lys Glu Leu Glu Thr Asn Val Ser Leu Lys Val Glu
         340                 345                 350

Glu Thr Asp Ser Ala Asp Lys Phe Lys Val Ser Gly Arg Gly Glu Leu
         355                 360                 365

His Leu Ser Ile Leu Ile Glu Thr Met Arg Arg Glu Gly Phe Glu Phe
         370                 375                 380

Gln Val Ser Lys Pro Thr Val Ile Tyr Lys Glu Glu Asn Gly Lys Lys
385                 390                 395                 400

Leu Glu Pro Ile Glu Glu Leu Thr Ile Asp Val Pro Glu Glu Phe Met
                 405                 410                 415

Gly Val Val Met Glu Lys Leu Gly Pro Arg Lys Ala Glu Leu Val Asn
         420                 425                 430

Met Thr Ser Ala Val Asn Gly Tyr Thr Arg Leu Glu Phe Lys Ile Pro
         435                 440                 445
```

Ser Arg Gly Leu Ile Gly Phe Arg Asn Glu Phe Met Thr Asp Thr Lys
    450                 455                 460
Gly Asn Gly Ile Met Asn Ser Thr Leu Ile Asp Tyr Glu Pro Phe Arg
465                 470                 475                 480
Gly Asp Ile Pro Glu Arg Ser Arg Gly Ser Ile Val Val Phe Glu Thr
                485                 490                 495
Gly Val Ser Val Val Tyr Gly Leu Tyr Ser Ala Gln Glu Arg Gly Arg
            500                 505                 510
Leu Phe Val Gly Ala Gly Val Asp Val Tyr Glu Gly Met Val Val Gly
        515                 520                 525
Glu Cys Ser Arg Ala Glu Asp Ile Glu Val Asn Val Cys Lys Lys Lys
    530                 535                 540
His Leu Ser Asn Thr Arg Ser Ser Gly Ala Asp Asp Ala Leu Lys Leu
545                 550                 555                 560
Val Pro Ile Pro Asp Met Ser Leu Glu Lys Cys Leu Glu Phe Ile Ala
                565                 570                 575
Ser Asp Glu Leu Val Glu Ile Thr Pro Lys Ser Ile Arg Met Arg Lys
            580                 585                 590
Lys Val Leu Asp Thr Asn Leu Arg Lys Lys Arg Lys
        595                 600                 605

<210> SEQ ID NO 9
<211> LENGTH: 1818
<212> TYPE: DNA
<213> ORGANISM: Clostridium acetobutylicum JB200

<400> SEQUENCE: 9
atggaaaaaa ttactagaaa tgatataaga aatattgcta atatagccca cgttgaccat      60
ggtaagacta ctctcgtgga tgctttactt agacaaagtc atgtttttag agcaaatgag     120
aaagttgaag agagagtaat ggattctaat gatctagaaa agaaagagg aataacaata      180
cttcctaaaa atacatcttt aatgcatgat ggaattaaaa ttaacatagt agatactcca     240
ggacatgctg attttggtgg agaggttgag cgtgtactta aatggtagga cagtgttctt     300
cttttagtag atgcttttga gggacctatg cctcagacta aatttgtttt gaaaaaagct     360
ttagagctta aattaaaacc aatagttgta ataaataaaa tagataagcc aaatgctaga     420
cctatggaag ttgtagatga agttttggac ttgttttatag acttaggtgc agatgaagat     480
caacttgact tcccaatagt ttatgcttct gtaaaagctg gtattgctaa gcttgatgta     540
gatgatgaaa gcgaaacaat ggaacctttg ttcgagacta ttgttaaata cgttaaaggt     600
cctgaaggat atcttgatga accacttcaa atgcttgttt ctacaataga ttctaatgaa     660
tatgttggta gaattgcaat aggaagagtt gaaagaggat ctataaagaa gaatcagcag     720
gctgttttaa taagacgtga tggagcaaag gaaaatgtaa aaatttcaag cttatttact     780
tatgaaggtc ttaagagagt tgaagctgat gaagttaagt ttggagatat tgctgtagtt     840
tcaggaatac ctgatgttaa atcggagaa acaattgcag atgcatctag accagaagca     900
ttaccttttg tagatattga tgagcctaca ttaagcatgt tcttcatggt aaatgattct     960
ccttttgcag gtagagaagg cgatttcgtt acatcaaggc atttaagaga cagacttgaa    1020
aaggaattag agacaaacgt aagtttaaaa gttgaagaaa ctgattcagc tgataaattc    1080
aaggtaagtg gaaggaggag acttcatctt tcaatattga tagaaacaat gagaagagaa    1140
ggattcgaat ccaagtatct aaaccaact gtaatataca agaggaaaa tggtaagaag     1200
ttagagccaa ttgaagagct cacaatagac gtaccagaag aatttatggg cgttgtaatg    1260

```
gagaagcttg gacctagaaa ggctgaactt gttaacatga cttcagctgt aaatggttat   1320
acaagattag agttcaaaat accttctaga ggtttaattg gattcagaaa tgagttcatg   1380
acagatacaa agggaaatgg aataatgaac tctacactta tagattatga accatttaga   1440
ggagatattc ctgaaagatc aagaggatct atagttgttt ttgaaacagg agtttcagtt   1500
gtctatggat tgtacagtgc tcaagaaaga ggaagattat ttgttggtgc tggagtagat   1560
gtttacgaag gaatggtagt tggagaatgt tcaagagccg aagatatcga agttaatgtt   1620
tgtaagaaaa agcatctttc aaacactaga tcttctggag ctgatgatgc tttaaaatta   1680
gttccaattc ctgacatgtc tttagagaaa tgtcttgagt ttatagcatc tgatgaattg   1740
gtagaaatca ctccaaagag cattagaatg agaaagaaag tcttagatac aaatttacgt   1800
aagaagaaaa gaaaatag                                                 1818
```

<210> SEQ ID NO 10
<211> LENGTH: 422
<212> TYPE: PRT
<213> ORGANISM: Clostridium acetobutylicum JB200

<400> SEQUENCE: 10

```
Met Lys Lys Pro Met Thr Met Thr Gln Lys Ile Leu Ala Asn His Ala
1               5                   10                  15

Gly Leu Asp Tyr Val Glu Ala Gly Gln Leu Ile Thr Ala Asn Leu Asp
            20                  25                  30

Leu Val Leu Gly Asn Asp Val Thr Thr Pro Val Ala Val Lys Ala Phe
        35                  40                  45

Lys Thr Met Gly Thr Asn Lys Val Phe Asp Lys Lys Val Ala Ile
    50                  55                  60

Val Pro Asp His Phe Thr Pro Asn Lys Asp Ile Lys Ser Ala Glu His
65                  70                  75                  80

Cys Lys Met Ile Arg Gln Phe Ala Lys Ser Lys Glu Ile Glu Asn Tyr
                85                  90                  95

Phe Glu Ile Gly Glu Met Gly Ile Glu His Ala Leu Ile Pro Glu Lys
            100                 105                 110

Gly Leu Ala Val Pro Gly Asp Val Ile Ile Gly Ala Asp Ser His Thr
        115                 120                 125

Cys Thr Tyr Gly Ala Leu Gly Val Phe Ser Thr Gly Val Gly Ser Thr
    130                 135                 140

Asp Met Ala Val Gly Met Ala Thr Gly Lys Ala Trp Phe Lys Val Pro
145                 150                 155                 160

Glu Ala Ile Lys Phe Val Leu Lys Gly Lys Pro Ala Lys Trp Val Ser
                165                 170                 175

Gly Lys Asp Ile Ile Leu His Ile Ile Gly Met Ile Gly Val Asp Gly
            180                 185                 190

Ala Leu Tyr Lys Ser Met Glu Tyr Thr Gly Asp Gly Leu Glu Tyr Leu
        195                 200                 205

Ser Met Asp Asp Arg Phe Thr Ile Ala Asn Met Ala Ile Glu Ala Gly
    210                 215                 220

Ala Lys Asn Gly Ile Phe Pro Val Asp Glu Lys Thr Ile Glu Tyr Met
225                 230                 235                 240

Lys Gly Arg Ser Asp Arg Glu Leu Lys Lys Phe Asp Ala Asp Glu Asp
                245                 250                 255

Ala Glu Tyr Ser Arg Val Ile Gly Ile Asp Leu Ser Thr Leu Lys Pro
            260                 265                 270
```

```
Thr Val Ala Phe Pro His Leu Pro Glu Asn Thr Lys Thr Ile Asp Gln
        275                 280                 285

Val Gly Glu Val Asn Val Asp Gln Val Val Ile Gly Ser Cys Thr Asn
        290                 295                 300

Gly Arg Met Glu Asp Leu Arg Ile Ala Thr Ser Ile Leu Lys Gly Lys
305                 310                 315                 320

Lys Ile Lys Lys Gly Ile Arg Leu Ile Val Phe Pro Gly Thr Gln Asn
                325                 330                 335

Ile Tyr Leu Glu Ala Met Glu Gly Leu Val Arg Thr Phe Ile Glu
                340                 345                 350

Ala Gly Gly Ile Val Ser Thr Pro Thr Cys Gly Pro Cys Leu Gly Gly
        355                 360                 365

His Met Gly Ile Leu Ala Glu Gly Glu Arg Ala Ile Ser Thr Thr Asn
    370                 375                 380

Arg Asn Phe Val Gly Arg Met Gly His Pro Lys Ser Glu Val Tyr Leu
385                 390                 395                 400

Ala Ser Pro Ala Val Ala Ala Ser Ala Ile Ala Gly Lys Ile Val
                405                 410                 415

Ser Pro Glu Glu Val Leu
                420

<210> SEQ ID NO 11
<211> LENGTH: 1269
<212> TYPE: DNA
<213> ORGANISM: Clostridium acetobutylicum JB200

<400> SEQUENCE: 11
atgaaaaaac cgatgactat gacacaaaaa atacttgcga accatgcagg gcttgattat      60
gtagaggcag acaacttat aacagctaac cttgatcttg ttttaggaaa tgatgtaact     120
acaccagtag ctgttaaagc atttaaaact atgggaacta acaaggtgtt tgataagaag     180
aaagtagcta tagtaccaga tcatttcaca cctaacaagg atataaaatc agcggaacac     240
tgtaagatga taagacaatt tgctaaaagt aaagaaatag agaactattt tgaaataggt     300
gaaatgggaa ttgagcatgc acttatccct gagaaaggac ttgctgttcc tggagatgta     360
ataataggag cagattcaca tacctgtacc tacggagcac tcggagtttt ttcaacaggc     420
gtcggaagta ctgatatggc agttggaatg gctacaggta agcttggtt taaggttcca     480 gaggctataa aatttgttct taaagggaag ccagcaaaat gggtgtctgg taaagatata     540
atactccaca taatcggaat gattggtgtt gacgagctt tatataaaatc gatggagtat     600 acaggtgatg gtctagagta tctttcaatg gatgacagat ttacaattgc aaatatggca     660
atagaagcag gagctaagaa tggaatattt cctgtagatg aaaagactat tgaatacatg     720
aagggtagaa gtgatagaga attaagaaa tttgatgcag acgaagatgc tgaatacagc     780
agggttatag aaatagattt aagtacatta aagcctacag ttgcatttcc acatttacct     840
gaaaatacaa aactatagag tcaggttgga gaggttaatg tagatcaagt agtaattggt     900
tcatgtacta tggaagaat ggaagactta agaattgcaa cttcgatctt aaaaggaaag     960
aaaattaaga agggaataag acttatagta ttcccaggaa ctcaaaacat ataccttgaa    1020
gctatggaag aaggactagt tagaacattt atagaagctg gcggaatagt aagtaccca    1080 acttgtggac cttgccttgg aggtcatatg ggaatacttg cagaaggaga aagagctata    1140
tctacaacta tagaaacttt gtgggtaga atgggacatc ctaagagtga agtttactta    1200
gcaagtccag cggtagcagc agcttcagca atagcaggaa aaatagtatc accagaggag    1260
```

```
gttttataa                                                              1269
```

<210> SEQ ID NO 12
<211> LENGTH: 445
<212> TYPE: PRT
<213> ORGANISM: Clostridium acetobutylicum ATCC 55025

<400> SEQUENCE: 12

| Met | Glu | Asn | Phe | Ser | Asp | Lys | Asp | Glu | Leu | Ile | His | Lys | Trp | Asp | Ser |
|---|---|---|---|---|---|---|---|---|---|---|---|---|---|---|---|
| 1 | | | | 5 | | | | | 10 | | | | | 15 | |

| Phe | Ile | Gly | Thr | Val | Glu | Lys | Asn | Pro | Thr | Leu | Arg | Pro | Leu | Thr | Met |
| | | | 20 | | | | | 25 | | | | | 30 | | |

| Glu | Ser | Trp | Lys | Arg | Cys | Lys | Asn | Met | Gly | Val | Asn | Pro | Lys | His | Ile |
| | | 35 | | | | | 40 | | | | | 45 | | | |

| Lys | Leu | Lys | Thr | Leu | Ser | His | Asn | Glu | Leu | Asn | Asp | Lys | Ile | Ser | Asn |
| | 50 | | | | | 55 | | | | | 60 | | | | |

| Asn | Leu | His | Leu | Ile | Lys | Ile | Val | Lys | Pro | Tyr | Phe | Asp | Tyr | Leu | Phe |
| 65 | | | | | 70 | | | | | 75 | | | | | 80 |

| Leu | Arg | Val | Thr | Asn | Ile | Pro | Phe | Leu | Ile | Ala | Leu | Ala | Asp | Ser | Lys |
| | | | | 85 | | | | | 90 | | | | | 95 | |

| Ala | Trp | Ile | Ile | Asn | Ile | Ser | Gly | Asn | Val | Asn | Asp | Phe | Gly | Glu | Lys |
| | | | 100 | | | | | 105 | | | | | 110 | | |

| Lys | Phe | Arg | Phe | Cys | Leu | Gly | Ser | Asn | Cys | Ser | Glu | Lys | Tyr | Ile | Gly |
| | | 115 | | | | | 120 | | | | | 125 | | | |

| Asn | Asn | Gly | Ile | Gly | Thr | Cys | Leu | Thr | Cys | Gly | Lys | Pro | Ile | Ile | Ile |
| | 130 | | | | | 135 | | | | | 140 | | | | |

| Tyr | Gly | Arg | Glu | His | Phe | Val | Asn | Ala | Tyr | Ala | Ser | Phe | Thr | Cys | Ile |
| 145 | | | | | 150 | | | | | 155 | | | | | 160 |

| Gly | Val | Pro | Ile | Lys | Val | Asn | Lys | Lys | Ile | Val | Gly | Ala | Ile | Asp | Val |
| | | | | 165 | | | | | 170 | | | | | 175 | |

| Cys | Ile | Pro | Asn | Lys | Tyr | Ala | His | Pro | Ser | Ile | Phe | Asp | Leu | Thr | Ile |
| | | | 180 | | | | | 185 | | | | | 190 | | |

| Ser | Cys | Val | Glu | Ser | Ile | Gln | Ser | Thr | Leu | Ser | Ile | Ile | Asp | Arg | Ser |
| | | 195 | | | | | 200 | | | | | 205 | | | |

| Ser | Ile | Lys | Asn | Ser | Pro | Asn | Met | Asn | Leu | Ser | Arg | Thr | Ser | Lys | Leu |
| | 210 | | | | | 215 | | | | | 220 | | | | |

| Leu | Ala | Thr | Ala | Val | His | Asp | Leu | Lys | Asn | Pro | Leu | Ser | Val | Ile | Arg |
| 225 | | | | | 230 | | | | | 235 | | | | | 240 |

| Gly | Leu | Gly | Gln | Leu | Gly | Lys | Leu | Thr | Ser | Asp | Lys | Ala | Lys | Ala | Asp |
| | | | | 245 | | | | | 250 | | | | | 255 | |

| Tyr | Tyr | Phe | Asp | Lys | Val | Ile | Lys | Gln | Ala | Asp | Glu | Leu | Asn | Thr | Met |
| | | | 260 | | | | | 265 | | | | | 270 | | |

| Val | Val | Glu | Leu | Leu | Ser | Ile | Phe | Ser | Pro | Pro | Lys | Ile | Lys | Pro | Met |
| | | 275 | | | | | 280 | | | | | 285 | | | |

| Glu | Ile | Ser | Lys | Ile | Ile | Lys | Asp | Val | Ile | Glu | Glu | Phe | Glu | Pro | Gln |
| | 290 | | | | | 295 | | | | | 300 | | | | |

| Cys | Asn | Ser | Lys | Lys | Ile | Ser | Leu | Asn | Ile | Ile | Asn | Ser | Asn | Ser | Ser |
| 305 | | | | | 310 | | | | | 315 | | | | | 320 |

| Tyr | Ala | Asn | Ile | Ser | Glu | Pro | Leu | Phe | Lys | Arg | Ala | Ile | Arg | Asn | Leu |
| | | | | 325 | | | | | 330 | | | | | 335 | |

| Ile | Ser | Asn | Ala | Ile | Gln | Ala | Ile | Asp | Ile | Asp | Gly | Ser | Ile | Glu | Ile |
| | | | 340 | | | | | 345 | | | | | 350 | | |

| Lys | Ile | Lys | Gln | Glu | Asn | Lys | His | Ile | Ile | Leu | Ser | Ile | Thr | Asp | Thr |
| | | 355 | | | | | 360 | | | | | 365 | | | |

| Ala | Gly | Gly | Ile | Pro | Glu | Glu | Leu | Arg | Asp | Asn | Leu | Phe | Glu | Pro | Phe |

```
                  370                 375                 380
Thr Phe Lys Arg Ser Gly Gly Thr Gly Leu Gly Leu Phe Met Val Tyr
385                 390                 395                 400

His Thr Ile Thr Asn Thr His Asn Gly Glu Met Trp Phe His Thr Thr
                    405                 410                 415

Pro Gly Asn Gly Thr Thr Phe Phe Ile Lys Leu Pro Ile Ala Asn Pro
                420                 425                 430

Thr Ser Asp Leu Asp Met Asp Lys Tyr Asn Leu Met Met
                435                 440                 445

<210> SEQ ID NO 13
<211> LENGTH: 509
<212> TYPE: PRT
<213> ORGANISM: Clostridium acetobutylicum ATCC 55025

<400> SEQUENCE: 13

Met Asn Thr Lys Met His Asn Lys Lys Arg Ile Phe Ser Ile Tyr
1               5                   10                  15

Ile Leu Leu Ile Leu Leu Ile Arg Leu Phe Leu Ser Thr Gly Val Arg
                20                  25                  30

Ile Trp Ala Phe Gly Asn Asn Gln Tyr Asp Asp Gly Met Met Ile Lys
            35                  40                  45

Asn Ala Thr Asn Leu Ile Ala Gly Asn Trp Leu Gly Ser Tyr Asp Gln
50                  55                  60

Tyr Ile Phe Ala Lys Gly Val Thr Phe Pro Ile Tyr Leu Glu Leu Leu
65                  70                  75                  80

His Lys Ile Gly Ile Pro Phe Ile Ile Ser Asn Val Leu Met Cys Phe
                85                  90                  95

Ala Ala Ser Leu Thr Phe Ile Ile Val Ile Lys Lys Val Ile Pro Asn
            100                 105                 110

Leu Asn Ala Leu Ala Ile Ile Tyr Thr Ile Leu Met Phe Asn Pro Ile
        115                 120                 125

Ala Thr Ala Ser Trp Thr Phe Gln Arg Val Tyr Arg Asp Ser Leu Tyr
130                 135                 140

Ser Tyr Leu Ile Val Ile Leu Phe Ser Leu Ile Ile Gly Ile Tyr Leu
145                 150                 155                 160

Asn Arg Lys Glu Ser Phe Asn Lys Leu Leu Ser Tyr Ser Ile Val Ala
                165                 170                 175

Gly Phe Phe Leu Ser Ser Val Trp Leu Ala Arg Glu Asp Ser Pro Trp
            180                 185                 190

Val Leu Pro Phe Val Gly Met Ala Leu Ile Val Thr Leu Val Leu Ile
        195                 200                 205

Phe Leu Asp Lys Asn Ser Glu Met Lys Val Arg Met Lys Lys Ala Leu
210                 215                 220

Ala Leu Thr Val Ile Pro Ile Phe Leu Ile Val Ser Ile Leu Val Val
225                 230                 235                 240

Ser Thr Ile Asn Tyr Thr Arg Tyr Gly Val Ala Ile Thr Asn Glu Tyr
                245                 250                 255

Thr Gly Gly Tyr Leu Pro Arg Leu Phe Lys Asp Leu Thr Ile Ile Gln
            260                 265                 270

Pro Asp Glu Trp Met Ala Gln Val Pro Ile Pro Lys Ser Thr Arg Glu
        275                 280                 285

Lys Ala Tyr Lys Val Ser Pro Thr Phe Ser Lys Leu Lys Asn Thr Leu
290                 295                 300

Glu Asn His Ala Phe Val Ala Thr Thr Pro Gly Gly Asn Ala Ser Cys
```

```
            305                 310                 315                 320
Ser Met Leu Ala Trp Ala Val Ile Asp Ser Val Gln Trp Tyr Gly Ile
                    325                 330                 335

Lys Asp Ala Lys Ser Ser Gln Glu Phe Tyr Lys Lys Ser Ser Glu Glu
                340                 345                 350

Ile Glu Ala Ala Ile Lys Ser Gly Lys Leu Lys Thr Arg Gly Gly Tyr
            355                 360                 365

Ile Phe Met Phe Glu Ser Pro Trp Asp Asn Arg Tyr Val Lys Pro Leu
        370                 375                 380

Leu Lys Ser Phe Ile Gln Thr Ile Lys Thr Thr Val His Met Gly Gln
385                 390                 395                 400

Tyr Tyr Asn Met Glu Glu Glu Ser Leu Val Lys Thr Leu Gln Leu Ser
                405                 410                 415

Arg Lys Tyr Asn Asn Thr Ile Val Pro Leu Phe Glu Lys Asn Ile Ala
                420                 425                 430

Ser Ile Gly Thr Lys Glu Gln Val Arg Lys Leu Glu Tyr Ile Thr Asn
            435                 440                 445

Asn Ile Ala Tyr Asn Lys Glu Asp Val Ile Pro Lys Arg Gln Thr Lys
        450                 455                 460

Val Ala Ile Ser Asn Lys Ile Ser Leu Ile Tyr Tyr Glu Leu Asn Pro
465                 470                 475                 480

Tyr Leu Phe Leu Ile Gly Leu Asn Arg Leu Cys Val Tyr Tyr Thr Ala
                485                 490                 495

Leu Phe Thr Lys Tyr Lys Lys Glu Lys Ile Leu Phe Ser
                500                 505

<210> SEQ ID NO 14
<211> LENGTH: 72
<212> TYPE: DNA
<213> ORGANISM: Clostridium acetobutylicum ATCC 55025

<400> SEQUENCE: 14
agcgggtaga gggaatcgaa ccctcgtaac tagcttggaa aggctagcac tctaccattg      60
agttacaccc gc                                                         72
```

What is claimed is:

1. A method of producing butanol, comprising:
   obtaining the *Clostridium acetobutylicum* strain deposited as ATCC PTA-12215; and
   producing butanol by subjecting the *Clostridium acetobutylicum* strain to fermentation with a substrate.

2. The method of claim 1, wherein the fermentation results in a higher concentration of butanol than fermentation with wild type *Clostridium acetobutylicum*.

3. The method of claim 1, wherein the substrate is selected from the group consisting of glucose, fructose, xylose, maltose, sucrose, galactose, and starch.

4. The method of claim 1, wherein the substrate is derived from the group consisting of starchy biomass, lignocellulosic biomass, and sugar-containing biomass.

5. The method of claim 1, further comprising the step of recovering butanol using a gas stripping system.

6. The method of claim 5, wherein the gas stripping system utilizes a stripping gas comprising $CO_2$ and $H_2$.

7. The method of claim 5, wherein the gas stripping system comprises a condenser for condensing vapor into a gas stripping condensate at a predetermined temperature.

8. The method of claim 7, wherein the predetermined temperature is 0° C.

9. The method of claim 7, further comprising the step of purifying the gas stripping condensate by distillation.

10. The method of claim 1, wherein the *Clostridium acetobutylicum* strain is identifiable by a sequence selected from the group consisting of SEQ ID NO:1, SEQ ID NO:3, SEQ ID NO:6, SEQ ID NO:8, and SEQ ID NO:10.

* * * * *